United States Patent
Akaiwa et al.

(10) Patent No.: US 12,390,536 B2
(45) Date of Patent: Aug. 19, 2025

(54) ANTIBODY-DRUG COMPLEX CONTAINING TOLL-LIKE RECEPTOR 7/8 DUAL AGONIST COMPOUND

(71) Applicant: ASTELLAS PHARMA INC., Tokyo (JP)

(72) Inventors: Michinori Akaiwa, Tokyo (JP); Yohei Seki, Tokyo (JP); Yinghua Wang, Tokyo (JP); Javier Ramos Miguelez, Tokyo (JP); Kei Ohnuki, Tokyo (JP); Takashi Kamikubo, Tokyo (JP); Toru Asano, Tokyo (JP); Akio Kamikawa, Tokyo (JP); Takashi Chaen, Tokyo (JP); Rika Hoshi, Tokyo (JP); Shinji Soga, Tokyo (JP); Chulwon Kwon, Tokyo (JP)

(73) Assignee: ASTELLAS PHARMA INC., Tokyo (JP)

( * ) Notice: Subject to any disclaimer, the term of this patent is extended or adjusted under 35 U.S.C. 154(b) by 0 days.

(21) Appl. No.: 18/896,098

(22) Filed: Sep. 25, 2024

(65) Prior Publication Data

US 2025/0025567 A1    Jan. 23, 2025

Related U.S. Application Data

(63) Continuation of application No. PCT/JP2023/039102, filed on Oct. 30, 2023.

(30) Foreign Application Priority Data

Oct. 31, 2022    (JP) .................. 2022-174538

(51) Int. Cl.
    *A61K 47/68*    (2017.01)

(52) U.S. Cl.
    CPC ...... *A61K 47/6803* (2017.08); *A61K 47/6849* (2017.08); *A61K 47/6889* (2017.08)

(58) Field of Classification Search
    None
    See application file for complete search history.

(56) References Cited

U.S. PATENT DOCUMENTS

2011/0059469 A1    3/2011    Aburatani et al.

FOREIGN PATENT DOCUMENTS

| JP | 2014-516956 A | 7/2014 |
| JP | 2017-514839 A | 6/2017 |

(Continued)

OTHER PUBLICATIONS

International Search Report issued in PCT/JP2023/039102 on Jan. 23, 2024, 5 pages.

*Primary Examiner* — Karl J Puttlitz
(74) *Attorney, Agent, or Firm* — Oblon, McClelland, Maier & Neustadt, L.L.P.

(57) ABSTRACT

An antibody-drug conjugate of formula (I) or salt thereof of formula I:

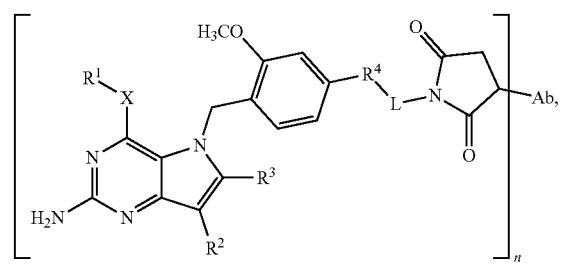

may have Ab as an anti-CLDN6 antibody or an antigen-binding fragment thereof. The antibody-drug conjugate of formula (I) may be (a) an antibody-drug conjugate comprising Ab bound to 1-{3-[(3S)-4-[(4-{[2-amino-4-(pentylamino)-5H-pyrrolo[3,2-d]pyrimidin-5-yl]methyl}-3-methoxyphenyl)methyl]-3-(fluoromethyl)piperazin-1-yl]-3-

(Continued)

NUGC-3 oxopropyl}-1H-pyrrole-2,5-dione, (b) an antibody-drug conjugate comprising Ab bound to {(2S)-1-[(4-{[2-amino-7-chloro-4-(pentylamino)-5H-pyrrolo[3,2-d]pyrimidin-5-yl]methyl}-3-methoxyphenyl)methyl]pyrrolidin-2-yl}methyl[2-(2,5-dioxo-2,5-dihydro-1H-pyrrol-1-yl)ethyl] carbamate, (c) an antibody-drug conjugate comprising Ab bound to N-[(4-{[2-amino-4-(pentylamino)-5H-pyrrolo[3,2-d]pyrimidin-5-yl]methyl}-3-methoxyphenyl)methyl]-N-cyclopropyl-3-(2,5-dioxo-2,5-dihydro-1H-pyrrol-1-yl)propenamide, or (d) an antibody-drug conjugate comprising Ab bound to 1-{3-[(3R)-4-[(4-{[2-amino-4-(pentylamino)-5H-pyrrolo[3,2-d]pyrimidin-5-yl]methyl}-3-methoxyphenyl)methyl]-3-(fluoromethyl)piperazin-1-yl]-3-oxopropyl}-1H-pyrrole-2,5-dione.

22 Claims, 4 Drawing Sheets

Specification includes a Sequence Listing.

(56) References Cited

FOREIGN PATENT DOCUMENTS

| JP | 2018-534297 A | 11/2018 |
| JP | 2020-531468 A | 11/2020 |
| JP | 2022-536490 A | 8/2022 |
| WO | WO 2009/087978 A1 | 7/2009 |
| WO | WO 2011/057788 A1 | 5/2011 |
| WO | WO 2012/156018 A1 | 11/2012 |
| WO | WO 2014/012479 A1 | 1/2014 |
| WO | WO 2015/168279 A1 | 11/2015 |
| WO | WO 2017/072662 A1 | 5/2017 |
| WO | WO 2018/198091 A1 | 11/2018 |
| WO | WO 2020/056008 A1 | 3/2020 |
| WO | WO 2020/252043 A1 | 12/2020 |
| WO | WO 2021/058027 A1 | 4/2021 |
| WO | WO 2021/067644 A1 | 4/2021 |

ANTIBODY-DRUG COMPLEX CONTAINING TOLL-LIKE RECEPTOR 7/8 DUAL AGONIST COMPOUND

REFERENCE TO A SEQUENCE LISTING

In accordance with 37 CFR §§ 1.831-1.835 and 37 CFR § 1.77(b)(5), the specification makes reference to a Sequence Listing submitted electronically as a .xml file named "FA1535-23184_Sequence_Listing." This .xml file was generated on August, 2024, and is 13,300 bytes in size. The entire contents of the Sequence Listing are hereby incorporated by reference.

CROSS-REFERENCE TO RELATED APPLICATIONS

The present invention is a bypass continuation of international application PCT/JP2023/039102, filed on Oct. 30, 2023, and claims the benefit of the filing date of Japanese Appl. No. 2022-174538, filed on Oct. 31, 2022, the content of each of which is incorporated by reference.

TECHNICAL FIELD

The present invention relates to an antibody-drug conjugate containing a compound having the action of a toll-like receptor 7 and 8 dual agonist (hereinafter the agonist will be sometimes referred to as a TLR7/8 dual agonist, and the compound as a drug) or a salt thereof, and relates a TLR7/8 dual agonist compound or a salt thereof. The present invention also relates to an anti-CLDN6 antibody for use in an antibody-drug conjugate or a salt thereof.

BACKGROUND ART

TLRs bind to a pathogen-associated molecular pattern of bacteria, fungi, protozoans and viruses to prevent intrusion of them, that is, serve as the front line of defense. TLR7 and 8 belonging to the TLR family are pattern recognition receptors mainly expressed in, e.g., dendritic cells, macrophages, monocytes and B cells. Activation of TLR7 and 8 is known to increase antigen-uptake/maturation by dendritic cells and enhance T-cell stimulation ability.

PTL 1 discloses a compound that can activate TLR7 and/or TLR8 represented by TM-Ln-AM (wherein TM is a targeting moiety, L is a linker, and n is an integer selected from 0 and 1, AM is an activating moiety that can activate dendritic cells, NK cells, tumor cells or a combination of these), for example, compounds containing trastuzumab and resiquimod, which are known to bind to a human epidermal growth factor receptor 2 (hereinafter also referred to as Her2).

For reference, the structure of resiquimod is shown below.

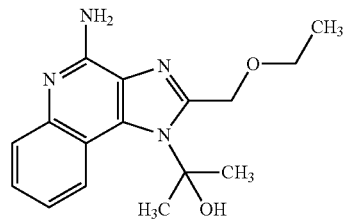 [SMILES: CCOCc1nc2c(N)nc3ccccc3c2n1C(C)(C)O]

In PTLs 2 and 3, a Her2 antibody-drug conjugate containing a TLR7 agonist is reported.

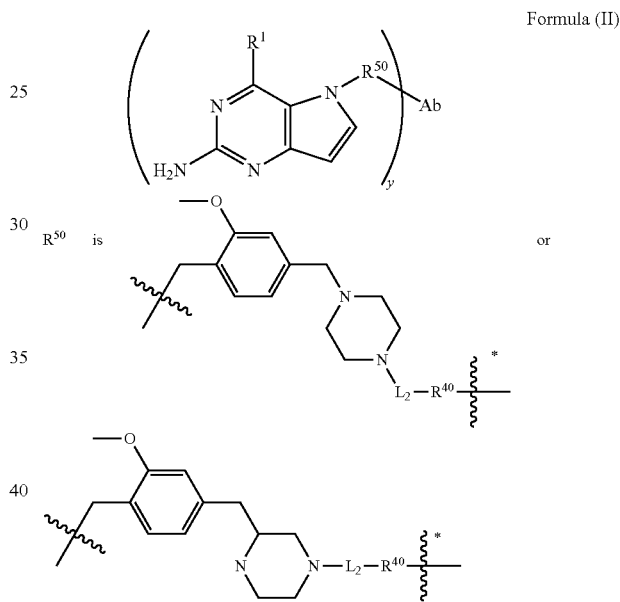

(For reference symbols in the formula, see PTLs 2 and 3).

In PTLs 4 and 5, e.g., a FOLR1 antibody-drug conjugate containing a TLR7 agonist is reported.

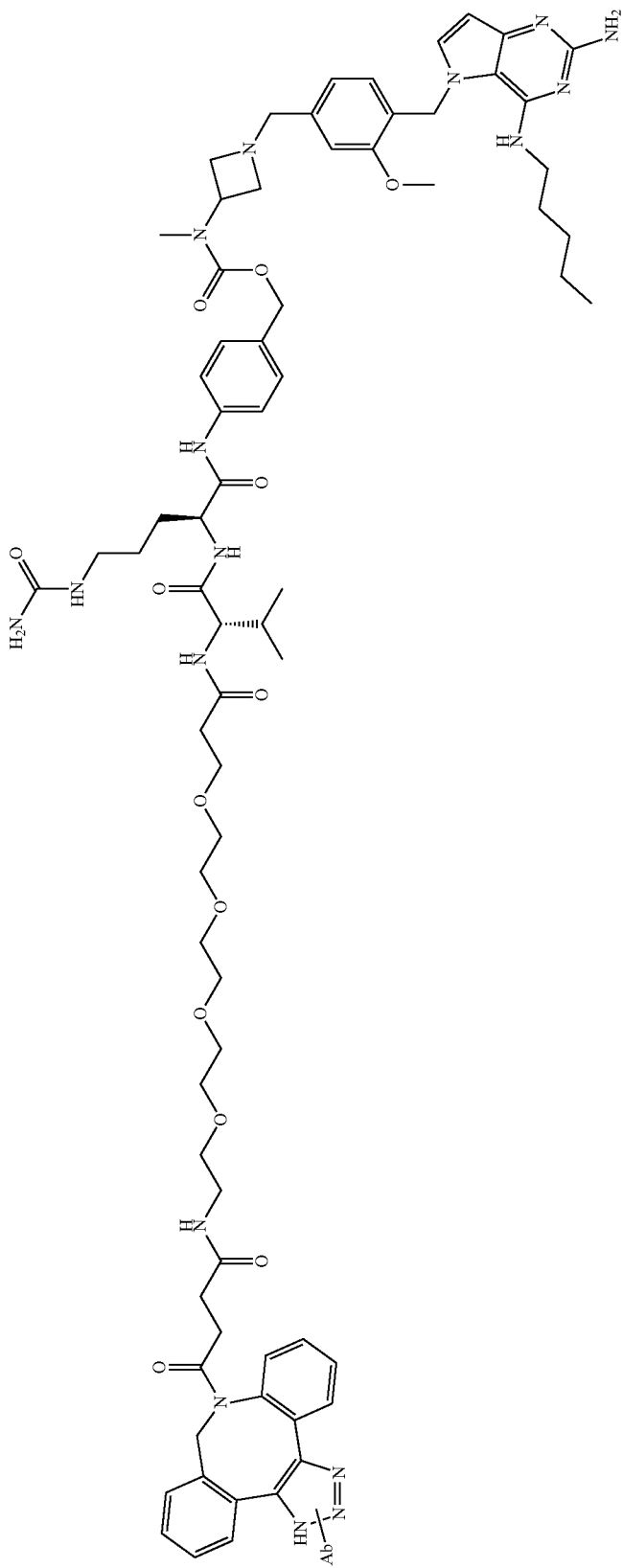

-continued
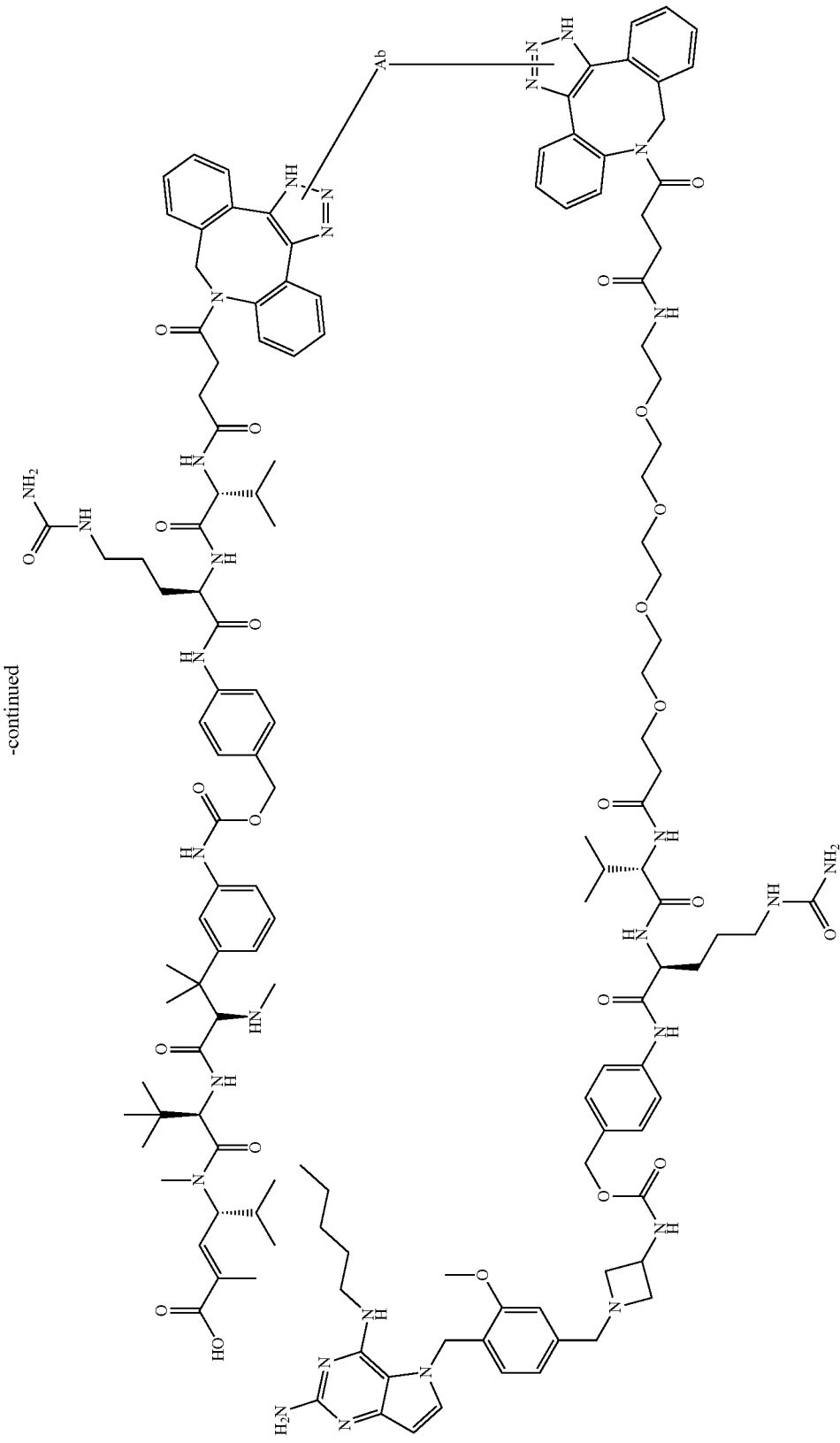

(For reference symbols in the formula, see PTLs 4 and 5).

In PTL 6, a TLR7 agonist compound is reported.

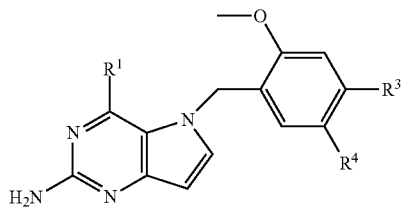

(For reference symbols in the formula, see PTL 6.

$R^3$ represents H, -L$_2$C(=O)OR$^7$, —C(=O)OLR$^{12}$, —C(=O)OL$_2$R$^{12}$, -L$_2$C(=O)OL$_2$R$^{12}$, -L$_4$C(=O)OL$_5$OH, -L$_4$R$^{12}$, (snip), L$_4$ is —(CH$_2$)m-, (snip); R$^{12}$ is a) —N(R$^{11}$)$_2$, b) an unsubstituted 5- or 6-membered heterocycloalkyl having 1 or 2 heteroatoms independently selected from N and O, c) a 5-6 membered heterocycloalkyl having 1 to 2 heteroatoms independently selected from N and O substituted with =O, d) a 5-6 membered heterocycloalkyl having 1 to 2 heteroatoms independently selected from N and O substituted with substituted with a C1 to C3 alkyl or —C(=O)OR$^7$, or e) an unsubstituted phenyl; and each m is independently selected from 1, 2, 3 and 4).

In PTL 4, a TLR7 agonist compound is also reported.

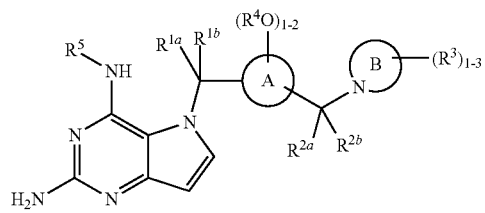

(For reference symbols in the formula, see PTL 4.

$R^3$ each independently represent —N(R$^{3a}$)$_2$, —OR$^{3b}$, —C(R$^{3c}$)$_2$NH$_2$, a C$_{1-6}$ alkyl, a heterocycloalkyl, a heteroaryl, a partially saturated heteroaryl or two R$^3$ bind to the same carbon atom and form a spiro-heterocycloalkyl together with the carbon atom, wherein (in R$^3$) the heterocycloalkyl, spiroheterocycloalkyl, heteroaryl and spiroheterocycloalkyl contain 1, 2, 3 or 4 heteroatoms selected from N, S and O and are optionally substituted with one or two C$_{1-3}$ alkyls).

Claudin 6 (hereinafter also referred to as CLDN6), which is a protein of the Claudin family, is a four-transmembrane protein consisting of 220 amino acid residues and an oncofetal gene expressed in embryoid body involved in mouse and human stem cells and epithelial cell-fate. CLDN6 is expressed at extremely low levels in normal tissues but overexpressed in tumors including childhood brain tumor and germ cell tumor, and cancers including gastric adenocarcinoma and ovarian cancer. Thus, it has been suggested that CLDN6 is a target for treating cancer (International Journal of Molecular Sciences, 2021, vol. 22, p. 13416).

As an anti-CLDN6 antibody, e.g., GT512muMAB 64A (PTL 7) and AE3-20 (PTL 8) have been reported. An antibody-drug conjugate containing a TLR7 and/or TLR8 agonist compound targeting CLDN6 and serving as a cancer therapeutic drug has not yet been reported.

CITATION LIST

Patent Literature

PTL 1: International Publication No. WO 2014/012479
PTL 2: International Publication No. WO 2017/072662
PTL 3: International Publication No. WO 2018/198091
PTL 4: International Publication No. WO 2020/252043
PTL 5: International Publication No. WO 2020/252015
PTL 6: International Publication No. WO 2015/168279
PTL 7: International Publication No. WO 2011/057788
PTL 8: International Publication No. WO 2009/087978

SUMMARY OF INVENTION

Technical Problem

An object of the present invention is to create a compound or a salt thereof having a TLR7/8 dual agonist action, develop an antibody-drug conjugate containing a TLR7/8 dual agonist compound, and provide a pharmaceutical composition for preventing or treating various cancers such as ovarian cancer, testicular cancer, cervical cancer and lung cancer. Further, another object of the present invention is also to provide an anti-CLDN6 antibody for use in an antibody-drug conjugate or a salt thereof.

Solution to Problem

The present inventors conducted intensive studies on an antibody-drug conjugate of formula (I). As a result, they found that a drug represented by formula (II) of the present invention has a TLR7/8 dual agonist action. They also found that the antibody for use in the antibody-drug conjugate of formula (I) has a binding activity to a target (human CLDN6); and that the antibody-drug conjugate of formula (I) induces production of TNF-α and INF-γ and exerts an in-vivo antitumor effect. Based on the findings, they arrived at the achievement of the present invention.

More specifically, the present invention relates to the following [1] to [3], and a pharmaceutical composition comprising excipients.

[1] An antibody-drug conjugate represented by formula (I):

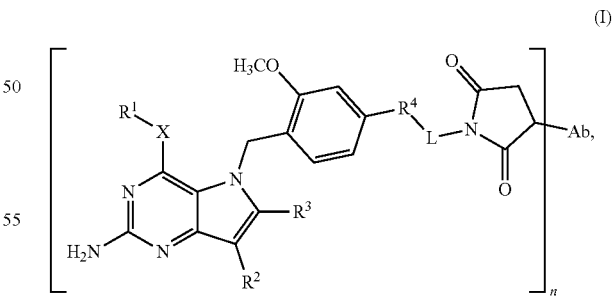

wherein
Ab represents an antibody or an antigen-binding fragment thereof,
X is S or NH,
$R^1$ is a lower alkyl or —CH$_2$-isoxazoldiyl-CH$_3$,
wherein if $R^1$ is —CH$_2$-isoxazoldiyl-CH$_3$, then X is S,
$R^2$ is halogen or H,
$R^3$ is CH$_3$ or H, and $R^4$ is a group represented by formula (a), formula (b) or formula (c):

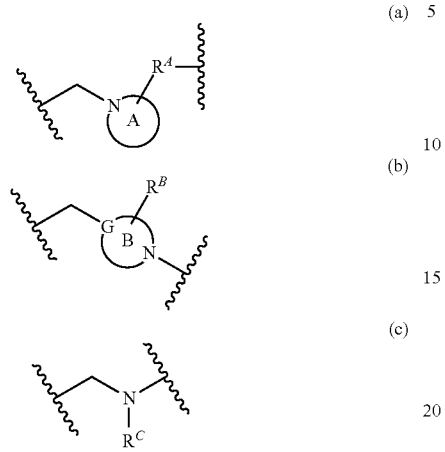

ring A is a 4- to 6-membered cyclic amine comprising a plurality of C and single N,
ring B is a 4- to 6-membered cyclic amine comprising a plurality of C, single N and single G,
G represents N or CH,
$R^A$ is —CH$_2$O—, —C(CH$_3$)$_2$O—, —O— or —CH$_2$NH—,
wherein if $R^A$ is —O— or —CH$_2$NH—, then X is S; $R^2$ is halogen; or $R^3$ is CH$_3$;
$R^B$ is a haloalkyl, CH$_2$OH, C(CH$_3$)$_2$OH, OH, CH$_2$NH$_2$ or H,
wherein if $R^B$ is OH, CH$_2$NH$_2$ or H, then G is CH; X is S; $R^2$ is halogen; or $R^3$ is CH$_3$;
$R^C$ is a C$_{3-6}$ cycloalkyl or a —CH$_2$—C$_{3-6}$ cycloalkyl,
L is -lower alkylene-, —C(=O) lower alkylene-, —C(=O)NH lower alkylene-, —C(=O) lower alkylene-(OCH$_2$CH$_2$)$_m$—NH—C(=O) lower alkylene-, —(CH$_2$CH$_2$O)$_m$—C(=O) lower alkylene-, or —C(=O)-cyclohexandiyl-lower alkylene-,
m represents an integer of 1 to 10, and
n represents 1 to 16;
or a salt thereof.

[2] An antibody-drug conjugate or a salt thereof, comprising a compound represented by formula (II):

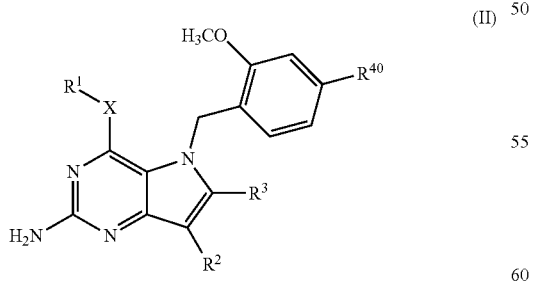

wherein
X is S or NH,
$R^1$ is a lower alkyl or —CH$_2$-isoxazoldiyl-CH$_3$,
wherein if $R^1$ is —CH$_2$-isoxazoldiyl-CH$_3$, then X is S,
$R^2$ is halogen or H,
$R^3$ is CH$_3$ or H, $R^{40}$ is a group represented by formula (a1), formula (b1) or formula (c1):

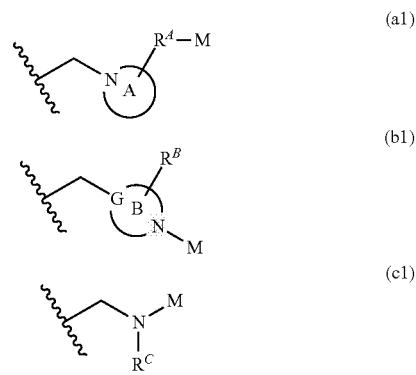

wherein
ring A is a 4- to 6-membered cyclic amine comprising a plurality of C and a single N atom,
ring B is a 4- to 6-membered cyclic amine comprising a plurality of C, single N and single G,
G is N or CH,
$R^A$ is —CH$_2$O—, —C(CH$_3$)$_2$O—, —O—, or —CH$_2$NH—,
wherein if $R^A$ is —O— or —CH$_2$NH—, then X is S; $R^2$ is halogen; or $R^3$ is CH$_3$;
$R^B$ is a haloalkyl, CH$_2$OH, C(CH$_3$)$_2$OH, OH, CH$_2$NH$_2$, or H,
wherein if $R^B$ is OH, CH$_2$NH$_2$ or H, then G is CH; X is S; $R^2$ is halogen; or $R^3$ is CH$_3$;
$R^C$ is a C$_{3-6}$ cycloalkyl or —CH$_2$—C$_{3-6}$ cycloalkyl, and
M is H or a group represented by formula (d):

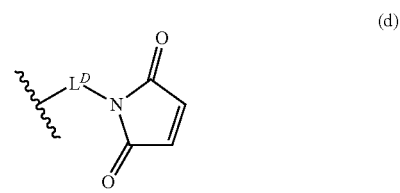

wherein
$L^D$ is -lower alkylene-, —C(=O) lower alkylene-, —C(=O)NH lower alkylene-, —C(=O) lower alkylene-(OCH$_2$CH$_2$)$_m$—NH—C(=O) lower alkylene-, —(CH$_2$CH$_2$O)$_m$—C(=O) lower alkylene-, or —C(=O)-cyclohexandiyl-lower alkylene-, and
m is an integer of 1 to 10; and
M represents H,
or a salt thereof, and
wherein a linker is bound at a position M.

[3] An anti-CLDN6 antibody or an antigen-binding fragment thereof comprising a heavy chain variable region consisting of the amino acid sequence of amino acid Nos. 1 to 117 of SEQ ID NO: 2 and a light chain variable region consisting of the amino acid Nos. 1 to 108 of SEQ ID NO: 4; or an anti-CLDN6 antibody or an antigen-binding fragment thereof comprising or a heavy chain variable region consisting of the amino acid sequence of amino acid Nos. 1 to 117 of SEQ ID NO: 6 and a light chain variable region consisting of the amino acid Nos. 1 to 108 of SEQ ID NO: 8.

Furthermore, the present invention is not limited to the embodiments [1] to [3] above, but also includes embodiments in which the contents described in the detailed invention of the specification are appropriately combined. As an embodiment, the present invention relates to a compound or a salt thereof, wherein M of the group represented by formula (a1), formula (b1), or formula (c1) in $R^{41}$ is H in a compound of formula (II) or a salt thereof described in above [2]. Moreover, as an embodiment, the present invention relates to an antibody-drug conjugate or a salt thereof, wherein an antibody is bound via a linker to the M position of the group represented by formula (a1), formula (b1), or formula (c1) in $R^{41}$ in a compound of formula (II) or a salt thereof described in above [2]. The binding group to be bound to the antibody in the linker is not limited to the maleimide group included in the group represented by formula (d) described in [2] above, and various binding groups described below can be used as appropriate. The linker is not limited to the $L^P$ included in the group represented by formula (d) described in [2] above, and various non-cleavable linkers and various cleavable linkers described below can be used as appropriate.

The present invention relates to an antibody-drug conjugate of formula (I) or a salt thereof, and a pharmaceutical composition containing an antibody-drug conjugate of formula (I) or a salt thereof, and one or more pharmaceutically acceptable excipients, particularly a pharmaceutical composition for preventing and/or treating cancer. The pharmaceutical composition includes a prophylactic and/or therapeutic agent for cancer containing an antibody-drug conjugate of formula (I) or a salt thereof.

The present invention relates to use of an antibody-drug conjugate of formula (I) or a salt thereof for producing a pharmaceutical composition for preventing and/or treating cancer; use of an antibody-drug conjugate of formula (I) or a salt thereof for preventing and/or treating cancer, an antibody-drug conjugate of formula (I) or a salt thereof for use in preventing and/or treating cancer; and a method for preventing and/or treating cancer, including administering an effective amount of an antibody-drug conjugate of formula (I) or a salt thereof to a subject.

The present invention relates to a compound of formula (II) or a salt thereof, and a pharmaceutical composition containing a compound of formula (II) or a salt thereof, and one or more pharmaceutically acceptable excipients, particularly, a pharmaceutical composition for preventing and/or treating cancer. The pharmaceutical composition includes a prophylactic and/or therapeutic agent for cancer containing a compound of formula (II) or a salt thereof.

The present invention relates to use of a compound represented by formula (II) or a salt thereof for producing a pharmaceutical composition for preventing and/or treating cancer; use of a compound represented by formula (II) or a salt thereof for preventing and/or treating cancer, a compound represented by formula (II) or a salt thereof for use in preventing and/or treating cancer; and a method for preventing and/or treating cancer, including administering an effective amount of a compound represented by formula (II) or a salt thereof to a subject.

The present invention relates to a pharmaceutical composition containing an antibody-drug conjugate or a salt thereof containing a compound of formula (II) or a salt thereof and one or more pharmaceutically acceptable excipients; and particularly, to a pharmaceutical composition for preventing and/or treating cancer. The pharmaceutical composition includes a prophylactic and/or therapeutic agent for cancer containing an antibody-drug conjugate or a salt thereof containing a compound of formula (II) or a salt thereof.

The present invention relates to use of an antibody-drug conjugate or a salt thereof containing a compound of formula (II) or a salt thereof for producing a pharmaceutical composition for preventing and/or treating cancer; use of an antibody-drug conjugate or a salt thereof containing a compound of formula (II) or a salt thereof for preventing and/or treating cancer; an antibody-drug conjugate or a salt thereof containing a compound of formula (II) or a salt thereof for use in preventing and/or treating cancer; and a method for preventing and/or treating cancer, including administering an effective amount of an antibody-drug conjugate or a salt thereof containing a compound of formula (II) or a salt thereof to a subject.

Note that, the "subject" refers to a human or a non-human animal required for its prevention or treatment and is a human required for its prevention or treatment, as an embodiment.

In the present invention, the type of cancer is not particularly limited and may be either solid cancer or blood cancer. Examples of cancer include blood cancers such as peritoneal disseminated cancers, stomach cancer, lung cancer, acute lymphoblastic leukemia, acute myeloid leukemia, Hodgkin lymphoma, non-Hodgkin lymphoma, B cell lymphoma, multiple myeloma and T cell lymphoma; solid cancers such as myelodysplastic syndrome, adenocarcinoma, squamous cell carcinoma, adenosquamous cell carcinoma, undifferentiated cancer, large-cell carcinoma, non-small cell lung cancer, small-cell lung cancer, mesothelioma, skin cancer, skin T cell lymphoma, breast cancer, prostate cancer, bladder cancer, vaginal cancer, neck cancer, head and neck cancer, uterine cancer, cervical cancer, liver cancer, gallbladder cancer, cholangiocarcinoma, kidney cancer, pancreatic cancer, colon cancer, colon cancer, rectal cancer, small bowel cancer, stomach cancer, esophageal cancer, testicular cancer, ovarian cancer and brain tumor; cancers of tissues such as bone tissue, cartilage tissue, fat tissue, muscle tissue, blood vessel tissue and hematopoiesis tissue; sarcomas such as chondrosarcoma, Ewing's sarcoma, malignant hemangioendothelioma, malignant schwannoma, osteosarcoma and soft tissue sarcoma; and blastomas such as, glioblastoma, glioblastoma multiforme, hepatoblastoma, medulloblastoma, nephroblastoma, neuroblastoma, pancreatoblastoma, pleuropulmonary blastoma, and retinoblastoma. As an embodiment, ovarian cancer, testicular cancer, cervical cancer, or lung cancer, can be mentioned. As an embodiment, ovarian cancer expressing CLDN6, testicular cancer expressing CLDN6, cervical cancer expressing CLDN6, or lung cancer expressing CLDN6, can be mentioned.

The specification incorporates the contents disclosed by Japanese Patent Application No. 2022-174538, which is the basis of the priority of the present application.

Advantageous Effects of Invention

A compound of formula (II) or a salt thereof has a TLR7/8 dual agonist action, and a compound of formula (II) or a salt thereof or an antibody-drug conjugate (I) or a salt thereof containing a TLR7/8 dual agonist compound has an effect on production of TNF-α or INF-γ and binds to a tumor-associated antigen expressed on a tumor surface to kill cancer cells to exert an in-vivo antitumor effect. Because of this, these compounds or salts thereof can be used as a prophylactic and/or therapeutic agent for cancer.

The anti-CLDN6 antibody of the present invention has binding activity to human CLDN6 and can be used in an antibody-drug conjugate or a salt thereof for use in a prophylactic and/or therapeutic agent for cancer.

DESCRIPTION OF EMBODIMENTS

Figure 1:
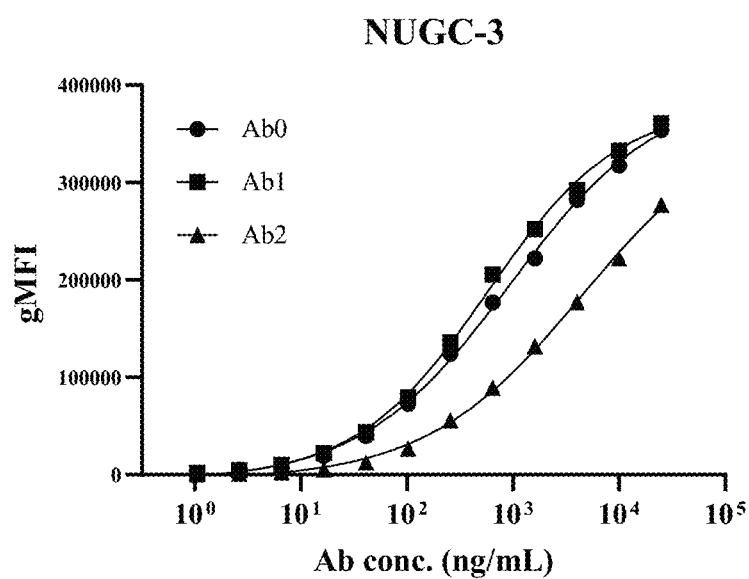
FIG. 1 shows the results on the binding activities of antibodies Ab0, Ab1 and Ab2 to human CLDN6 expressing gastric cancer cell line NUGC-3 evaluated by flow cytometry. The vertical axis depicts geometric mean fluorescence intensity and the horizontal axis depicts antibody concentration (ng/mL).

Now, the present invention will be more specifically described.

In the specification, the terms set forth below have the following meanings unless otherwise specified. The following definitions are made for the purpose of clearly specifying the terms but should not be construed as limiting the terms. The terms not specifically defined herein are used in a sense generally accepted by those skilled in the art. Unless otherwise specified, if reference symbols used in a chemical formula are used in other chemical formulas herein, it should be understood that like reference symbols have the like meanings.

The "lower alkyl" refers to a linear or branched alkyl having 1 to 6 (hereinafter simply referred to as $C_{1-6}$) carbon atoms, such as methyl, ethyl, n-propyl, isopropyl, n-butyl, isobutyl, sec-butyl, tert-butyl, n-pentyl, and n-hexyl. As an embodiment, the lower alkyl is a $C_{1-6}$ alkyl. As an embodiment, the lower alkyl is a $C_{1-5}$ alkyl. As an embodiment, the lower alkyl is methyl. As an embodiment, the lower alkyl is n-pentyl.

The "lower alkylene" refers to a linear or branched $C_{1-6}$ alkylene, such as methylene, ethylene, trimethylene, tetramethylene, pentamethylene, hexamethylene, propylene, methylmethylene, dimethylmethylene, ethyl ethylene, 1,2-dimethyl ethylene, and 1,1,2,2-tetramethyl ethylene. As an embodiment, the lower alkylene is a $C_{1-4}$ alkylene. As an embodiment, the lower alkylene is ethylene (—$CH_2CH_2$—).

The "halogen" refers to F, Cl, Br or I.

The "haloalkyl" refers to a lower alkyl, in which the alkyl is substituted with at least one halogen. As an embodiment, the haloalkyl is a $C_{1-6}$ alkyl substituted with at least one halogen. As an embodiment, the haloalkyl is a lower alkyl substituted with one to five halogens. As an embodiment, the haloalkyl is a lower alkyl substituted with one to five F. As an embodiment, the haloalkyl is a lower alkyl substituted with one to three F. As an embodiment, the haloalkyl is monofluoromethyl.

The "$C_{3-6}$ cycloalkyl" refers to a $C_{3-6}$ saturated cyclic hydrocarbon group such as cyclopropyl, cyclobutyl, cyclopentyl, and cyclohexyl. As an embodiment, the $C_{3-6}$ cycloalkyl is a $C_{3-4}$ cycloalkyl. As an embodiment, the $C_{3-6}$ cycloalkyl is cyclobutyl. As an embodiment, the $C_{3-6}$ cycloalkyl is cyclopropyl.

The "cyclic amine" refers to a non-aromatic cyclic amine having at least one nitrogen atom (N) and having a ring consisting of carbon atoms (C), such as aziridine, azetidine, pyrrolidine, piperidine, piperazine, azepane and diazepane. Examples of a divalent group thereof include aziridindiyl, azetidindiyl, pyrrolidindiyl, piperidindiyl, piperazindiyl, azepandiyl and diazepandiyl. Examples of a monovalent group thereof include aziridinyl, azetidinyl, pyrrolidinyl, piperidyl, piperazinyl, azepanyl and diazepanyl. An embodiment thereof is a 4- to 6-membered cyclic amine comprising a plurality of C and single N. An embodiment thereof is a 4- to 6-membered cyclic amine comprising a plurality of C, single N and single G, and G is N or CH. An embodiment thereof is a 5-membered cyclic amine comprising four C and single N. An embodiment thereof is a 6-membered cyclic amine comprising two C, single N, two C and single G, and G is N or CH. An embodiment thereof is a 6-membered cyclic amine comprising two C, single N, two C and single G, and G is N. An embodiment thereof is a 6-membered cyclic amine comprising two C, single N, two C and single G, and G is CH.

The "4- to 6-membered cyclic amine" refers to a cyclic amine having a 4- to 6-membered ring such as azetidine, pyrrolidine, piperidine, and piperazine. Examples of a divalent group thereof include azetidindiyl, pyrrolidindiyl, piperidindiyl, and piperazindiyl. Example of a monovalent group thereof include azetidinyl, pyrrolidinyl, piperidyl, and piperazinyl. As an embodiment, the 4- to 6-membered cyclic amine is 6-membered cyclic amine. As an embodiment, the 4- to 6-membered cyclic amine is 5-membered cyclic amine. As an embodiment, the 4- to 6-membered cyclic amine is piperidindiyl or piperazindiyl. As an embodiment, the 4- to 6-membered cyclic amine is pyrrolidindiyl or piperazindiyl. As an embodiment, the 4- to 6-membered cyclic amine is piperidindiyl. As an embodiment, the 4- to 6-membered cyclic amine is pyrrolidindiyl. As an embodiment, the 4- to 6-membered cyclic amine is piperazindiyl. As an embodiment, the 4- to 6-membered cyclic amine is a 4- to 6-membered cyclic amine comprising a plurality of carbon atoms and a single nitrogen atom. As an embodiment, the 4- to 6-membered cyclic amine is a 4- to 6-membered cyclic amine comprising a plurality of carbon atoms, a single nitrogen atom and single G wherein G represents CH or N. As an embodiment, the 4- to 6-membered cyclic amine is a 5-membered cyclic amine comprising four C and single N. As an embodiment, the 4- to 6-membered cyclic amine is a 6-membered cyclic amine comprising five C and single N. As an embodiment, the 4- to 6-membered cyclic amine is a 6-membered cyclic amine comprising four C, single N and single G wherein G is CH or N. As an embodiment, the 4- to 6-membered cyclic amine is a 6-membered cyclic amine comprising four C, single G and single G, wherein G is N. As an embodiment, the 4- to 6-membered cyclic amine is a 6-membered cyclic amine comprising four C, single N and single G, wherein G is CH. As an embodiment, the 4- to 6-membered cyclic amine is a 6-membered cyclic amine comprising four C, single N and single G wherein G is CH or N. As an embodiment, the 4- to 6-membered cyclic amine is a 6-membered cyclic amine comprising two C, single N, two C and single G wherein G is CH or N. As an embodiment, the 4- to 6-membered cyclic amine is a 6-membered cyclic amine comprising two C, single N, two C, and single G wherein G is N. As an embodiment, the 4- to 6-membered cyclic amine is a 6-membered cyclic amine comprising two C, single N, two C, and single G wherein G is CH.

The "antibody-drug conjugate" refers to a conjugate formed by binding an antibody and at least one drug via a linker. The drug can be delivered to cells or tissues targeted by the antibody. As an embodiment, the antibody-drug conjugate is a conjugate formed by binding an antibody and a drug via a non-cleavable linker. In the specification, the "antibody-drug conjugate containing a compound" refers to an antibody-drug conjugate formed by binding an antibody and a compound via a linker. An embodiment thereof is an antibody-drug conjugate having a linker and an embodiment thereof is an antibody-drug conjugate having no linker.

The "linker" refers to a chemical group via which an antibody and a drug are bound, and is capable of forming at least two covalent bonds. There are non-cleavable linkers and cleavable linkers. Examples of the linker for use in an antibody-drug conjugate include an alkylene, polyethylene glycol (PEG) and a peptide. For the purpose of binding linkers to each other or using linkers in combination, e.g., an amide group, an ether group or a carbamate group is used. Examples of the binding group to be bound to the antibody in the linker include a maleimide group, a pyridyldithio group, an isocyanate group and the like.

The "non-cleavable linker" refers to a linker that cannot be decomposed either in acidic conditions within a lysosome or with a specific protease within a cell. Examples of the linker include -lower alkylene-, —C(=O) lower alkylene-, —C(=O)NH lower alkylene-, —C(=O) lower alkylene-(OCH$_2$CH$_2$)$_m$—NH—C(=O) lower alkylene-, —(CH$_2$CH$_2$O)m-C(=O) lower alkylene-, and —C(=O)-cyclohexandiyl-CH$_2$—, wherein "m" represents an integer of 1 to 10, and it includes any consistent combination of those embodiments. As an embodiment, the non-cleavable linker is —CH$_2$CH$_2$—, —C(=O)CH$_2$CH$_2$—, —C(=O)NHCH$_2$CH$_2$—, —C(=O)CH$_2$CH$_2$—(OCH$_2$CH$_2$)$_m$—NH—C(=O)CH$_2$CH$_2$—, —(CH$_2$CH$_2$O)$_m$—C(=O)CH$_2$CH$_2$—, or —C(=O)-cyclohexandiyl-CH$_2$—. As an embodiment, the non-cleavable linker is —CH$_2$CH$_2$, —C(=O)CH$_2$CH$_2$—, or —C(=O)NHCH$_2$CH$_2$—. As an embodiment, the non-cleavable linker is —C(=O)CH$_2$CH$_2$—, or —C(=O)NHCH$_2$CH$_2$—. As an embodiment, the non-cleavable linker is —C(=O)CH$_2$CH$_2$—. As an embodiment, if the non-cleavable linker is —C(=O)NHCH$_2$CH$_2$—, an oxygen atom (O) of a compound or a salt thereof is bound to —C(=O) of the linker. As an embodiment, "m" represents an integer of 1 to 8 or 4 to 8. As an embodiment, "m" represents an integer of 4 or 8.

The "cleavable linker" refers to a linker that may be selectively cleaved in acidic conditions within a lysosome or with an endogenous enzyme within a cell, such as a specific protease, a nuclease, and a peptidase. Examples of the cleavable linker include a hydrazone bond, an S—S bond, a peptide bond, an ester bond, a phosphate ester bond, one or both ester bonds of a phosphodiester bond and a carbamate bond. For example, Val-Cit (valine citrulline), Val-Ala, Ala-Ala, Ala-Ala-Ala, Gly-Gly-Phe-Gly, Val-Cit-PABC (valine citrulline-p-benzyl alcohol), Val-Ala-PABC, or a consistent combination of these embodiments (Bioconjugate Chemistry 2002, vol. 13, p. 855-869; Protein & Cell, 2018, vol. 9, p. 33-46.)

The "drug-linker conjugate" refers to a compound prepared by binding a drug and a linker through a reaction, or a salt thereof. As an embodiment, the "drug-linker conjugate" is a compound or a salt thereof, in which the compound of the subject invention and a linker are covalently bonded. An antibody-drug conjugate can be produced by binding a drug-linker conjugate to an antibody or antibody-binding fragment thereof. The linker of the drug-linker conjugate is covalently bound to the antibody. The antibody-drug conjugate binds at least one drug-linker conjugate to an antibody or antibody-binding fragment thereof. As an embodiment, at least one drug (such as anticancer drug or label, etc.) linker conjugate can be further bound to the antibody portion of the antibody-drug conjugate. Examples of anticancer drugs include tubulin polymerization inhibitors such as monomethyl auristatin E (MMAE) and monomethyl auristatin F (MMAF), and mitosis inhibitor mertansine (DM1). Examples of labels include radioisotopes (RI-labeled antibodies) and the like.

The "TLR7/8 dual agonist" refers to an agonist that acts both as a TLR7 agonist and a TLR8 agonist. An embodiment thereof is a compound or a salt thereof having an agonist action to TLR7, which is stronger than that shown by EC$_{50}$ value of 150 nM (more specifically EC$_{50}$ value is smaller than 150 nM) in reporter assay and an agonist action to TLR8, which is stronger than that shown by EC$_{50}$ value of 15 μM (more specifically EC$_{50}$ value is smaller than 15 μM). An embodiment thereof is a compound or a salt thereof having an agonist action to TLR7, which is stronger than that shown by EC$_{50}$ value of 1 μM (more specifically EC$_{50}$ value is smaller than 1 μM) in reporter assay and an agonist action to TLR8, which is stronger than that shown by EC$_{50}$ value of 15 μM (more specifically EC$_{50}$ value is smaller than 15 μM). The "TLR7/8 dual agonist compound" refers to a compound or a salt thereof serving as a TLR7/8 dual agonist.

The "TLR7/8 dual inhibitor" refers to an inhibitor serving as a TLR7 inhibitor as well as a TLR8 inhibitor. For example, the "TLR7/8 dual inhibitor" includes Enpatoran and the like.

The antibody moiety of the "antibody-drug conjugate" is an antibody binding to a predetermined antigen or an antigen-binding fragment.

Antibodies have 5 classes: IgG, IgM, IgA, IgD and IgE. The basic structure of these antibody molecules is common in all of the classes and is composed of heavy chains having a molecular weight of 50,000 to 70,000 and light chains having a molecular weight of 20,000 to 30,000. A heavy chain consists of a polypeptide chain comprising usually about 440 amino acids and has a characteristic structure, which varies depending on the class. The structures corresponding to IgG, IgM, IgA, IgD, and IgE are called Igγ, Igμ, Igα, Igδ, and Igε, respectively. IgG further has 4 subclasses: IgG1, IgG2, IgG3, and IgG4. The heavy chains corresponding to the subclasses are called Igγ1, Igγ2, Igγ3, and Igγ4, respectively. A light chain consists of a polypeptide chain comprising usually about 220 amino acids. Two types of light chains: λ type and κ type, are known. They are called Igλ and Igκ, respectively. The basic peptide structure of an antibody molecule is composed of two identical heavy chains and two identical light chains, which are connected via disulfide bonds (S—S binding) and non-covalent bonds, and has a molecular weight of 150,000 to 190,000. Two types of light chains can be paired with either one of the heavy chains. Individual antibody molecules are each composed of two identical light chains and two identical heavy chains without exception.

In an antibody, the number of intrachain S—S bonds in a heavy chain is 4 (5 in Igμ and Igε) and 2 in a light chain. A single loop is formed for every unit of 100 to 110 amino acid residues. The three-dimensional structures of the loops are analogous and called as a structure unit or a domain. The domains positioned at the N terminals of both the heavy chain and the light chain have amino acid sequences, which are not constant between antibodies even if they are produced from the same class (subclass) of allogeneic animals, are called variable regions. The domains are called a heavy chain variable region (VH) and a light chain variable region (VL), respectively. The amino acid sequences closer to the C-terminal side than the variable regions are almost constant between the classes or subclasses, and called constant regions (individual domains are represented by CH1, CH2, CH3 and CL).

In an antibody, an antigen-determining site comprises VH and VL and binding specificity is determined by the amino acid sequence of the site. In contrast, biological activity such as binding to a complement and various Fc receptor-expressing cells reflects differences in structures of the constant regions of individual Ig classes. The variability of the variable regions of the light chain and heavy chain is limitedly observed in three small hypervariable regions in both chains. These hypervariable regions are called complementarity-determining regions (CDRs, referred to as CDR1, CDR2, CDR3 from the N terminal side). The remaining parts of the variable region are called framework regions (FR), which are relatively constant.

The "antigen-binding fragment" refers to a fragment comprising VH and VL of an antibody and having binding activity to an antigen. Typical antigen-binding fragments are single-chain variable region fragments (scFv), Fab, Fab' and F(ab')$_2$. The scFv is a monovalent antibody fragment comprising VH and VL connected by a peptidelinker. The Fab is a monovalent antibody fragment comprising a light chain, VH and CH1 domains, and part of a hinge region. The Fab' is a monovalent antibody fragment comprising a light chain, VH and CH1 domains, and part of a hinge region. The moiety of the hinge region contains a cysteine residue that was used to constitute a S—S bond between heavy chains. The F(ab')2 fragment is a divalent antibody fragment formed by connecting two Fab' fragments via a S—S bond between heavy chains in the hinge region. As an embodiment, the antigen-binding fragment to be used in the present invention is scFv, Fab, Fab' or F(ab')2.

The "post-translational modification" refers to modification chemically and biologically made after completion of mRNA translation when an antibody is expressed in a cell. Examples of chemical modification include chemical binding to an amino acid skeleton such as chemical binding to a carbohydrate chain via N-link or O-link. Examples of biological modification include a post-translational modification (for example, N-linked or O-linked glycosylation, N-terminal or C-terminal processing, deamidation, isomerization of aspartic acid, oxidation of methionine) and addition of a methionine residue to the N-terminal, which is achieved by expressing a gene in a prokaryotic host cell. It is known in the technical field that such a post-translational modification does not affect the activity of an antibody (Anal Biochem., 2006, Vol. 348, p. 24-39).

The "anti-TAA antibody" refers to an antibody that binds to a tumor-associated antigen (TAA) expressed on the surface of tumor cells. The anti-TAA antibody is an antibody that can reach a target tumor cell, or an antigen-binding fragment thereof. Examples of the anti-TAA antibody include, but are not limited to, an anti-A33 antibody, an anti-B7-H3 antibody, an anti-CanAg antibody, an anti-CD20 antibody, an anti-CD22 antibody, an anti-CD30 antibody, an anti-CD33 antibody, an anti-CD56 antibody, an anti-CD70 antibody, an anti-CEA, an anti-CLDN6 antibody, an anti-EphA2 antibody, an anti-G250 antibody, an anti-MUC1 antibody, an anti-GPNMB antibody, an anti-Integrin antibody, an antibody PSMA antibody, an anti-Tenascin-C antibody, an anti-TROP-2 antibody, and an anti-TSPAN8 antibody.

The "anti-CLDN6 antibody" refers to an antibody that binds to CLDN6 or an antigen-binding fragment thereof. As an embodiment, the anti-CLDN6 antibody is an anti-CLDN6 antibody or an antigen-binding fragment thereof selected from the following group consisting of (Ab-A) to (Ab-D):

(Ab-A) An anti-CLDN6 antibody or an antigen-binding fragment thereof comprising a heavy chain variable region comprising CDR1 consisting of amino acid sequence of amino acid Nos. 31 to 35 of SEQ ID NO: 2, CDR2 consisting of the amino acid sequence of amino acid Nos. 50 to 65 of SEQ ID NO: 2, and CDR3 consisting of the amino acid sequence of amino acid Nos. 95 to 102 of SEQ ID NO: 2; and a light chain variable region comprising CDR1 consisting of the amino acid sequence of amino acid Nos. 24 to 34 of SEQ ID NO: 4, CDR2 consisting of the amino acid sequence of amino acid Nos. 50 to 56 of SEQ ID NO: 4, and CDR3 consisting of the amino acid sequence of amino acid Nos. 89 to 97 of SEQ ID NO: 4;

(Ab-B) An anti-CLDN6 antibody or an antigen-binding fragment thereof comprising a heavy chain variable region comprising CDR1 consisting of the amino acid sequence of amino acid Nos. 31 to 35 of SEQ ID NO: 6, CDR2 consisting of the amino acid sequence of amino acid Nos. 50 to 65 of SEQ ID NO: 6, and CDR3 consisting of the amino acid sequence of amino acid Nos. 95 to 102 of SEQ ID NO: 6; and a light chain variable region comprising CDR1 consisting of the amino acid sequence of amino acid Nos. 24 to 34 of SEQ ID NO: 8, CDR2 consisting of the amino acid sequence of amino acid Nos. 50 to 56 of SEQ ID NO: 8, and CDR3 consisting of the amino acid sequence of amino acid Nos. 89 to 97 of SEQ ID NO: 8;

(Ab-C) An anti-CLDN6 antibody or an antigen-binding fragment thereof comprising a heavy chain variable region consisting of the amino acid sequence of amino acid Nos. 1 to 117 of SEQ ID NO: 2 and a light chain variable region consisting of the amino acid sequence of the amino acid Nos. 1 to 108 of SEQ ID NO: 4; and (Ab-D) An anti-CLDN6 antibody or an antigen-binding fragment thereof comprising a heavy chain variable region consisting of the amino acid sequence of amino acid Nos. 1 to 117 of SEQ ID NO: 6 and a light chain variable region consisting of the amino acid sequence of the amino acid Nos. 1 to 108 of SEQ ID NO: 8.

As an embodiment, the anti-CLDN6 antibody may further contain a heavy chain constant region and a light chain constant region. As the constant region, a constant region of any subclass antibody (for example, constant region of a heavy chain such as Igγ1, Igγ2, Igγ3 or Igγ4 and a light chain such as Igκ or Igκ) can be selected. The heavy chain constant region may be a human Igγ1 constant region and the light chain constant region may be a human Igκ constant region.

As an embodiment, the anti-CLDN6 antibody may be Ab1 or Ab2.

The "Ab1" refers to an anti-CLDN6 antibody comprising a heavy chain consisting of the amino acid sequence of SEQ ID NO: 2 and a light chain consisting of the amino acid sequence of SEQ ID NO: 4.

The "Ab2" refers to an anti-CLDN6 antibody comprising a heavy chain consisting of the amino acid sequence of SEQ ID NO: 6 and a light chain consisting of the amino acid sequence of SEQ ID NO: 8.

As an embodiment, the anti-CLDN6 antibody is an anti-CLDN6 antibody having post-translational modification or an antigen-binding fragment thereof. As an embodiment, the anti-CLDN6 antibody is an anti-CLDN6 antibody comprising a heavy chain consisting of the amino acid sequence of SEQ ID NO: 2 and having post-translational modification and a light chain consisting of the amino acid sequence of SEQ ID NO: 4, or the anti-CLDN6 antibody is an anti-CLDN6 antibody comprising a heavy chain consisting of the amino acid sequence of SEQ ID NO: 6 and having post-translational modification and a light chain consisting of the amino acid sequence of SEQ ID NO: 8. As an embodiment, the anti-CLDN6 antibody is Ab1 or Ab2 antibody having post-translational modification.

The binding activity of an antibody to a tumor cell can be confirmed by a method for measuring binding activity commonly known in the technical field. Examples of the method for measuring binding activity include Enzyme-Linked Immunosorbent Assay (ELISA) known in the technical field. When ELISA is used, for example, CLDN6 is immobilized onto an ELISA plate. Then, a test antibody is added and allowed to react with CLDN6, and thereafter, a secondary antibody such as an anti-IgG antibody labeled with an enzyme such as horseradish peroxidase (HRP), is allowed to react. After completion of the reaction, the plate was washed and the activity is measured by use of a reagent for detecting the activity (for example, for detection of a HRP label, TMB Microwell Peroxidase Substrate (company: Kirkegaard & Perry Laboratories 50-76-03)) to identify binding of the secondary antibody. In this manner, whether the test antibody binds to CLDN6 can be checked.

Embodiment of the Present Invention [1]

Embodiments of an antibody-drug conjugate of formula (I) or a salt thereof according to the present invention will be shown below. All embodiments can be used in combination. Even if combinations are not specifically set forth, one or two or more embodiments can be used in combination with an embodiment.

An embodiment is the antibody-drug conjugate or a salt thereof, wherein formula (I) is formula (IA):

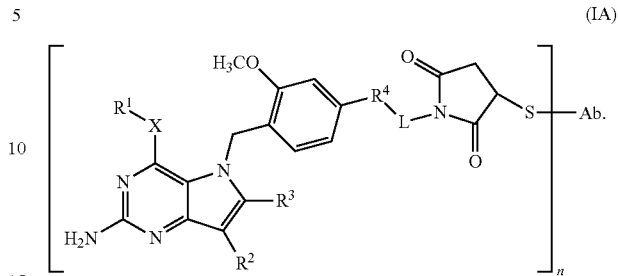

An embodiment is the antibody-drug conjugate or a salt thereof represented by formula (IA) in which antibody Ab in formula (I) binds via SH.

(2) An embodiment is the antibody-drug conjugate of formula (I) or a salt thereof, wherein Ab is an antitumor-associated antigen (TAA) antibody or an antigen-binding fragment thereof. An embodiment is the antibody-drug conjugate of formula (I) or a salt thereof, wherein Ab is an anti-TAA antibody selected from the group consisting of an anti-A33 antibody, an anti-B7-H3 antibody, an anti-CanAg antibody, an anti-CD20 antibody, an anti-CD22 antibody, an anti-CD30 antibody, an anti-CD33 antibody, an anti-CD56 antibody, an anti-CD70 antibody, an anti-CEA antibody, an anti-CLDN6 antibody, an anti-EphA2 antibody, an anti-G250 antibody, an anti-MUC1 antibody, an anti-GPNMB antibody, an anti-Integrin antibody, an antibody PSMA antibody, an anti-Tenascin-C antibody, an anti-TROP-2 antibody and anti-TSPAN8 antibody, or an antigen-binding fragment thereof. An embodiment is the antibody-drug conjugate of formula (I) or a salt thereof, wherein Ab is an anti-CLDN6 antibody or an antigen-binding fragment thereof. An embodiment is the antibody-drug conjugate of formula (I) or a salt thereof, wherein Ab is an anti-CLDN6 antibody selected from the group consisting of the following (Ab-A) to (Ab-D) or an antigen-binding fragment thereof: (Ab-A) An anti-CLDN6 antibody or an antigen-binding fragment thereof comprising a heavy chain variable region comprising CDR1 consisting of amino acid sequence of amino acid Nos. 31 to 35 of SEQ ID NO: 2, CDR2 consisting of the amino acid sequence of amino acid Nos. 50 to 65 of SEQ ID NO: 2, and CDR3 consisting of the amino acid sequence of amino acid Nos. 95 to 102 of SEQ ID NO: 2; and a light chain variable region comprising CDR1 consisting of the amino acid sequence of amino acid Nos. 24 to 34 of SEQ ID NO: 4, CDR2 consisting of the amino acid sequence of amino acid Nos. 50 to 56 of SEQ ID NO: 4, and CDR3 consisting of the amino acid sequence of amino acid Nos. 89 to 97 of SEQ ID NO: 4; (Ab-B) An anti-CLDN6 antibody or an antigen-binding fragment thereof comprising a heavy chain variable region comprising CDR1 consisting of the amino acid sequence of amino acid Nos. 31 to 35 of SEQ ID NO: 6, CDR2 consisting of the amino acid sequence of amino acid Nos. 50 to 65 of SEQ ID NO: 6, and CDR3 consisting of the amino acid sequence of amino acid Nos. 95 to 102 of SEQ ID NO: 6; and a light chain variable region comprising CDR1 consisting of the amino acid sequence of amino acid Nos. 24 to 34 of SEQ ID NO: 8, CDR2 consisting of the amino acid sequence of amino acid Nos. 50 to 56 of SEQ ID NO: 8, and CDR3 consisting of the amino acid sequence of amino acid Nos. 89 to 97 of SEQ ID NO: 8; (Ab-C) An anti-CLDN6 antibody or an antigen-binding fragment thereof comprising a heavy chain variable region consisting of the amino acid sequence of amino acid Nos. 1 to 117 of SEQ ID NO: 2 and a light chain variable region consisting of the amino acid sequence of the amino acid Nos. 1 to 108 of SEQ ID NO: 4; and (Ab-D) An anti-CLDN6 antibody or an antigen-binding fragment thereof comprising a heavy chain variable region consisting of the amino acid sequence of amino acid Nos. 1 to 117 of SEQ ID NO: 6 and a light chain variable region consisting of the amino acid sequence of amino acid Nos. 1 to 108 of SEQ ID NO: 8. An embodiment is the antibody-drug conjugate of formula (I) or a salt thereof, wherein Ab is the anti-CLDN6 antibody or an antigen-binding fragment thereof according to (Ab-A). An embodiment is the antibody-drug conjugate of formula (I) or a salt thereof, wherein Ab is the anti-CLDN6 antibody or an antigen-binding fragment thereof according to (Ab-B). An embodiment is the antibody-drug conjugate of formula (I) or a salt thereof, wherein Ab is the anti-CLDN6 antibody or an antigen-binding fragment thereof according to (Ab-C). An embodiment is the antibody-drug conjugate of formula (I) or a salt thereof, wherein Ab is the anti-CLDN6 antibody or an antigen-binding fragment thereof according to (Ab-D). An embodiment is the antibody-drug conjugate of formula (I) or a salt thereof, wherein Ab is an anti-CLDN6 antibody or an antigen-binding fragment thereof selected from the group consisting of Ab-A and Ab-B. An embodiment is the antibody-drug conjugate of formula (I) or a salt thereof, wherein Ab is an anti-CLDN6 antibody or an antigen-binding fragment thereof selected from the group consisting of Ab-C and Ab-D. An embodiment is the antibody-drug conjugate of formula (I) or a salt thereof, wherein Ab is selected from Ab1 and Ab2: (Ab1) an anti-CLDN6 antibody comprising a heavy chain consisting of the amino acid sequence of SEQ ID NO: 2 and a light chain consisting of the amino acid sequence of SEQ ID NO: 4; and (Ab2) an anti-CLDN6 antibody comprising a heavy chain consisting of the amino acid sequence of SEQ ID NO: 6 and a light chain consisting of the amino acid sequence of SEQ ID NO: 8. The antibody-drug conjugate of formula (I) or a salt thereof, wherein Ab is anti-CLDN6 antibody Ab1. The antibody-drug conjugate of formula (I) or a salt thereof, wherein Ab is anti-CLDN6 antibody Ab2. An embodiment is the antibody-drug conjugate of formula (I) or a salt thereof, wherein Ab is anti-CLDN6 antibody Ab1 or Ab2 having post-translational modification. An embodiment is the antibody-drug conjugate of formula (I) or a salt thereof, wherein Ab is an anti-CLDN6 antibody comprising a heavy chain consisting of the amino acid sequence of SEQ ID NO: 2 and having post-translational modification and a light chain consisting of the amino acid sequence of SEQ ID NO: 4, or a heavy chain consisting of the amino acid sequence of SEQ ID NO: 6 and having post-translational modification and a light chain consisting of the amino acid sequence of SEQ ID NO: 8.

(3) An embodiment is the antibody-drug conjugate of formula (I) or a salt thereof, wherein X is S. An embodiment is the antibody-drug conjugate of formula (I) or a salt thereof, wherein X is NH.

(4) An embodiment is the antibody-drug conjugate of formula (I) or a salt thereof, wherein $R^1$ is a lower alkyl. An embodiment is the antibody-drug conjugate of formula (I) or a salt thereof, wherein $R^1$ is normal pentyl. An embodiment is the antibody-drug conjugate of formula (I) or a salt thereof, wherein $R^1$ is —$CH_2$-isoxazoldiyl-$CH_3$ and X is S. An embodiment is the antibody-drug conjugate of formula (I) or a salt thereof, wherein $R^1$ is —$CH_2$-(5-methylisoxazol-3-yl) and X is S.

(5) An embodiment is the antibody-drug conjugate of formula (I) or a salt thereof, wherein $R^2$ is a halogen. An embodiment is the antibody-drug conjugate of formula (I) or a salt thereof, wherein $R^2$ is Br, Cl or H. An embodiment is the antibody-drug conjugate of formula (I) or a salt thereof, wherein $R^2$ is Cl or H. An embodiment is the antibody-drug conjugate of formula (I) or a salt thereof, wherein $R^2$ is H.

(6) An embodiment is the antibody-drug conjugate of formula (I) or a salt thereof, wherein $R^3$ is $CH_3$. An embodiment is the antibody-drug conjugate of formula (I) or a salt thereof, wherein $R^3$ is H.

(7) An embodiment is the antibody-drug conjugate of formula (I):

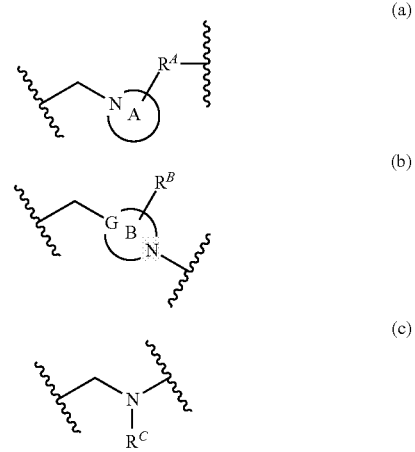

wherein $R^4$ is a group represented by formula (a), formula (b) or formula (c); or a salt thereof.

An embodiment is the antibody-drug conjugate of formula (I) or a salt thereof, wherein $R^4$ is a group represented by formula (a) or formula (b). An embodiment is the antibody-drug conjugate of formula (I) or a salt thereof, wherein $R^4$ is a group represented by formula (b) or formula (c). An embodiment is the antibody-drug conjugate of formula (I) or a salt thereof, wherein $R^4$ is a group represented by formula (c) or formula (a). An embodiment is the antibody-drug conjugate of formula (I) or a salt thereof, wherein $R^4$ is a group represented by formula (a). An embodiment is the antibody-drug conjugate of formula (I) or a salt thereof, wherein $R^4$ is a group represented by formula (b). An embodiment is the antibody-drug conjugate of formula (I) or a salt thereof, wherein $R^4$ is a group represented by formula (c).

(8) An embodiment is the antibody-drug conjugate of formula (I) or a salt thereof, wherein ring A is a 5-membered cyclic amine comprising four C and single N. An embodiment is the antibody-drug conjugate of formula (I) or a salt thereof, wherein ring A is a 6-membered cyclic amine comprising five C and single N. An embodiment is the antibody-drug conjugate of formula (I) or a salt thereof, wherein ring A is pyrrolidine. An embodiment is the antibody-drug conjugate of formula (I) or a salt thereof, wherein ring A is piperazine.

(9) An embodiment is the antibody-drug conjugate of formula (I) or a salt thereof, wherein ring B is a 6-membered cyclic amine comprising four C, single N and single G. An embodiment is the antibody-drug conjugate of formula (I) or a salt thereof, wherein ring B is a 6-membered cyclic amine comprising two C, single N, two C and single G. An embodiment is the antibody-drug conjugate of formula (I) or a salt thereof, wherein ring B is piperazine.

(10) An embodiment is the antibody-drug conjugate of formula (I) or a salt thereof, wherein G is N. An embodiment is the antibody-drug conjugate of formula (I) or a salt thereof, wherein G is CH.

(11) An embodiment is the antibody-drug conjugate of formula (I) or a salt thereof, wherein $R^A$ is —CH$_2$O— or —C(CH$_3$)$_2$O—. An embodiment is the antibody-drug conjugate of formula (I) or a salt thereof, wherein $R^A$ is —CH$_2$O—.

(12) An embodiment is the antibody-drug conjugate of formula (I) or a salt thereof, wherein $R^B$ is a haloalkyl, CH$_2$OH or C(CH$_3$)$_2$OH. An embodiment is the antibody-drug conjugate of formula (I) or a salt thereof, wherein $R^B$ is a haloalkyl or H, wherein if $R^B$ is H, G is N. An embodiment is the antibody-drug conjugate of formula (I) or a salt thereof, wherein $R^B$ is a haloalkyl. An embodiment is the antibody-drug conjugate of formula (I) or a salt thereof, wherein $R^B$ is fluoromethyl. An embodiment is the antibody-drug conjugate of formula (I) or a salt thereof, wherein $R^B$ is monofluoromethyl.

(13) An embodiment is the antibody-drug conjugate of formula (I) or a salt thereof, wherein $R^C$ is a C$_{3-6}$ cycloalkyl. An embodiment is the antibody-drug conjugate of formula (I) or a salt thereof, wherein $R^C$ is a —CH$_2$—C$_{3-6}$ cycloalkyl. An embodiment is the antibody-drug conjugate of formula (I) or a salt thereof, wherein $R^C$ is cyclopropyl. An embodiment is the antibody-drug conjugate of formula (I) or a salt thereof, wherein $R^C$ is —CH$_2$-cyclobutyl.

(14) An embodiment is the antibody-drug conjugate of formula (I) or a salt thereof, wherein L is -lower alkylene-, —C(=O) lower alkylene-, —C(=O)NH lower alkylene- or —C(=O) lower alkylene-(OCH$_2$CH$_2$)$_m$—NH—C(=O) lower alkylene-. An embodiment is the antibody-drug conjugate of formula (I) or a salt thereof, wherein L is -lower alkylene-, —C(=O) lower alkylene- or —C(=O)NH lower alkylene-. An embodiment is the antibody-drug conjugate of formula (I) or a salt thereof, wherein L represents —C(=O) lower alkylene- or —C(=O)NH lower alkylene-. An embodiment is the antibody-drug conjugate of formula (I) or a salt thereof, wherein L is a non-cleavable linker. An embodiment is the antibody-drug conjugate of formula (I) or a salt thereof, wherein L is —C(=O) lower alkylene-. An embodiment is the antibody-drug conjugate of formula (I) or a salt thereof, wherein L is —C(=O)CH$_2$CH$_2$— or —C(=O)NHCH$_2$CH$_2$—. An embodiment is the antibody-drug conjugate of formula (I) or a salt thereof, wherein L is —C(=O)CH$_2$CH$_2$—. An embodiment is the antibody-drug conjugate of formula (I) or a salt thereof, wherein L is —C(=O)NHCH$_2$CH$_2$—. The antibody-drug conjugate of formula (I) or a salt thereof according to the embodiment of (14), wherein if L contains —C(=O)NH lower alkylene- (herein, as a subordinate concept, for example —C(=O)NHCH$_2$CH$_2$— is also included), the —C(=O)NH lower alkylene- is bound to $R^A$ in the formula (a) of $R^4$ and $R^A$ is —CH$_2$O— or —C(CH$_3$)$_2$O—. The antibody-drug conjugate of formula (I) or a salt thereof according to the embodiment of (14), wherein if L contains a —C(=O)NH lower alkylene- (herein, as a subordinate concept, for example —C(=O)NHCH$_2$CH$_2$— is also included), the —C(=O)NH lower alkylene- is bound to $R^A$ in the formula (a) of $R^4$ and $R^A$ is —CH$_2$O—.

(15) An embodiment is the antibody-drug conjugate of formula (I) or a salt thereof, wherein m is an integer of 4 to 8. An embodiment is the antibody-drug conjugate of formula (I) or a salt thereof, wherein m is an integer of 4 or 8.

(16) An embodiment is the antibody-drug conjugate of formula (I) or a salt thereof, wherein n is 1 to 16. An embodiment is the antibody-drug conjugate of formula (I) or a salt thereof, wherein n is 2 to 5. An embodiment is the antibody-drug conjugate of formula (I) or a salt thereof, wherein n is 1 to 8.

(17) The antibody-drug conjugate of formula (I) or a salt thereof, which is a compatible combination of two or more of the embodiments according to the above (1) to (16). Examples of the compatible combination of two or more of the embodiments according to the above (1) to (16) include embodiments (1) and (16) of an antibody-drug conjugate or a salt thereof; the embodiment of the antibody according to the above (2) of an antibody-drug conjugate or a salt thereof wherein the antibody is selected; the embodiments of the drug according to the above (3) to (13) of an antibody-drug conjugate or a salt thereof wherein the drug is selected; and the embodiments of the linker according to the above (14) and (15) of an antibody-drug conjugate or a salt thereof wherein the linker is selected.

Examples of the combination according to (17) follow.

[1] The antibody-drug conjugate of formula (I) or a salt thereof, wherein Ab is any one of anti-TAA antibodies such as an anti-A33 antibody, an anti-B7-H3 antibody, an anti-CanAg antibody, an anti-CD20 antibody, an anti-CD22 antibody, an anti-CD30 antibody, an anti-CD33 antibody, an anti-CD56 antibody, an anti-CD70 antibody, an anti-CEA antibody, an anti-CLDN6 antibody, an anti-EphA2 antibody, an anti-G250 antibody, an anti-MUC1 antibody, an anti-GPNMB antibody, an anti-Integrin antibody, an antibody PSMA antibody, an anti-Tenascin-C antibody, an anti-TROP-2 antibody and an anti-TSPAN8 antibody, or an antigen-binding fragment thereof; X is S or NH; $R^1$ is a lower alkyl or —CH$_2$-isoxazoldiyl-CH$_3$, wherein if $R^1$ is —CH$_2$-isoxazoldiyl-CH$_3$, X is S; $R^2$ is halogen or H; $R^3$ is CH$_3$ or H; and $R^4$ is a group represented by formula (a), formula (b) or formula (c):

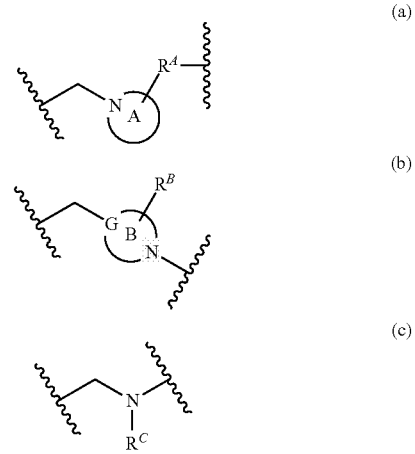

wherein ring A is a 4- to 6-membered cyclic amine comprising a plurality of C and a single N; ring B is a 4- to 6-membered cyclic amine comprising a plurality of C, single N and single G; G is N or CH; $R^A$ is —CH$_2$O—, —C(CH$_3$)$_2$O—, —O— or —CH$_2$NH—, wherein if $R^A$ is —O— or —CH$_2$NH—, then X is S; $R^2$ is halogen; or $R^3$ is CH$_3$; $R^B$ is a haloalkyl, CH$_2$OH, C(CH$_3$)$_2$OH,OH, CH$_2$NH$_2$ or H, wherein if $R^B$ is OH, CH$_2$NH$_2$ or H, then G is CH; X is S; $R^2$ is halogen; or $R^3$ is CH$_3$; $R^C$ is C$_{3-6}$ cycloalkyl, or —CH$_2$—C$_{3-6}$ cycloalkyl; L is -lower alkylene-, —C(=O) lower alkylene-, —C(=O)NH lower alkylene-, —C(=O) lower alkylene-(OCH$_2$CH$_2$)$_m$—NH—C(=O) lower alkylene-, —(CH$_2$CH$_2$O)$_m$—C(=O) lower alkylene-, or —C(=O)-cyclohexandiyl-lower alkylene-; and m is an integer of 1 to 10, n is 1 to 16.

[1a] An antibody-drug conjugate of formula (I) and a salt thereof, wherein Ab is an anti-CLDN6 antibody selected from the following Ab1 and Ab2: (Ab1) an anti-CLDN6 antibody comprising a heavy chain consisting of the amino acid sequence of SEQ ID NO: 2 and a light chain consisting of the amino acid sequence of SEQ ID NO: 4; and (Ab2) an anti-CLDN6 antibody comprising a heavy chain consisting of the amino acid sequence of SEQ ID NO: 6 and a light chain consisting of the amino acid sequence of SEQ ID NO: 8; X is NH; R$^1$ is a lower alkyl; R$^2$ is H; R$^3$ is H; R$^4$ is represented by formula (a), formula (b) or formula (c); ring A is a 5-membered cyclic amine comprising four C and single N; ring B is a 6-membered cyclic amine comprising two C, single N, two C and single G; G is N; R$^A$ is —CH$_2$O—; R$^B$ is a haloalkyl; R$^c$ is a C$_{3-6}$ cycloalkyl; and L is —C(=O)CH$_2$CH$_2$— or —C(=O)NHCH$_2$CH$_2$—.

[2] An antibody-drug conjugate of formula (I) or a salt thereof, wherein ring A is a 5-membered cyclic amine comprising four C and single N; ring B is a 6-membered cyclic amine comprising two C, single N, two C and single G wherein G is N.

[3] The antibody-drug conjugate of formula (I) or a salt thereof according to [2], wherein R$^A$ is —CH$_2$O— or —C(CH$_3$)$_2$O—, R$^B$ is a haloalkyl, CH$_2$OH or C(CH$_3$)$_2$OH.

[4] The antibody-drug conjugate of formula (I) or a salt thereof according to [3], wherein X is NH; R$^1$ is a lower alkyl; and R$^3$ is H.

[5] The antibody-drug conjugate of formula (I) or a salt thereof according to [4], wherein L is -lower alkylene-, —C(=O) lower alkylene-, —C(=O)NH lower alkylene-, or —C(=O) lower alkylene-(OCH$_2$CH$_2$)$_m$—NH—C(=O) lower alkylene-; and m is an integer of 4 to 8.

[6] The antibody-drug conjugate of formula (I) or a salt thereof according to [5], wherein L is -lower alkylene-, —C(=O) lower alkylene- or —C(=O)NH lower alkylene-.

[7] The antibody-drug conjugate of formula (I) or a salt thereof, wherein X is NH; R$^1$ is a lower alkyl; R$^2$ is a halogen; R$^3$ is H; R$^4$ is represented by formula (a); ring A is a 5-membered cyclic amine comprising four C and single N; R$^A$ is —CH$_2$O—; and L is —C(=O)NHCH$_2$CH$_2$—.

[8] The antibody-drug conjugate of formula (I) or a salt thereof, wherein X is NH; R$^1$ is a lower alkyl; R$^2$ is H; R$^3$ is H; R$^4$ is represented by formula (b); ring B is a 6-membered cyclic amine comprising two C, single N, two C and single G where G is N; R$^B$ is a haloalkyl; and L is —C(=O)CH$_2$CH$_2$—.

[9] The antibody-drug conjugate of formula (I) or a salt thereof, wherein X is NH; R$^1$ is a lower alkyl; R$^2$ is H; R$^3$ is H; R$^4$ is represented by formula (c); R$^c$ is a C$_{3-6}$ cycloalkyl; and L is —C(=O)CH$_2$CH$_2$—.

[10] An antibody-drug conjugate is an antibody-drug conjugate of formula (I) or a salt thereof according to [1], selected from the group consisting of an antibody-drug conjugate comprising Ab bound to 1-{3-[(3S)-4-[(4-{[2-amino-4-(pentylamino)-5H-pyrrolo[3,2-d]pyrimidin-5-yl]methyl}-3-methoxyphenyl)methyl]-3-(fluoromethyl)piperazin-1-yl]-3-oxopropyl}-1H-pyrrole-2,5-dione, an antibody-drug conjugate comprising Ab bound to {(2S)-1-[(4-{[2-amino-7-chloro-4-(pentylamino)-5H-pyrrolo[3,2-d]pyrimidin-5-yl]methyl}-3-methoxyphenyl)methyl]pyrrolidin-2-yl}methyl[2-(2,5-dioxo-2,5-dihydro-1H-pyrrol-1-yl)ethyl]carbamate, an antibody-drug conjugate comprising Ab bound to N-[(4-{[2-amino-4-(pentylamino)-5H-pyrrolo[3,2-d]pyrimidin-5-yl]methyl}-3-methoxyphenyl)methyl]-N-cyclopropyl-3-(2,5-dioxo-2,5-dihydro-1H-pyrrol-1-yl)propenamide, and an antibody-drug conjugate comprising Ab bound to 1-{3-[(3R)-4-[(4-{[2-amino-4-(pentylamino)-5H-pyrrolo[3,2-d]pyrimidin-5-yl]methyl}-3-methoxyphenyl)methyl]-3-(fluoromethyl)piperazin-1-yl]-3-oxopropyl}-1H-pyrrole-2,5-dione.

[11] The antibody-drug conjugate of formula (I) or a salt thereof according to [2] to [10], wherein Ab is any one of anti-TAA antibodies such as an anti-A33 antibody, an anti-B7-H3 antibody, an anti-CanAg antibody, an anti-CD20 antibody, an anti-CD22 antibody, an anti-CD30 antibody, an anti-CD33 antibody, an anti-CD56 antibody, an anti-CD70 antibody, an anti-CEA antibody, an anti-CLDN6 antibody, an anti-EphA2 antibody, an anti-G250 antibody, an anti-MUC1 antibody, an anti-GPNMB antibody, an anti-Integrin antibody, an antibody PSMA antibody, an anti-Tenascin-C antibody, an anti-TROP-2 antibody and an anti-TSPAN8 antibody, or an antigen-binding fragment thereof.

[12] The antibody-drug conjugate or a salt thereof according to [11], wherein Ab is an anti-CLDN6 antibody.

[13] The antibody-drug conjugate or a salt thereof according to [12], wherein Ab is an anti-CLDN6 antibody or an antigen-binding fragment thereof selected from the group consisting of Ab-A and Ab-B: Ab-A is an anti-CLDN6 antibody or an antigen-binding fragment thereof comprising a heavy chain variable region comprising CDR1 consisting of amino acid sequence of amino acid Nos. 31 to 35 of SEQ ID NO: 2, CDR2 consisting of the amino acid sequence of amino acid Nos. 50 to 65 of SEQ ID NO: 2, and CDR3 consisting of the amino acid sequence of amino acid Nos. 95 to 102 of SEQ ID NO: 2; and a light chain variable region comprising CDR1 consisting of the amino acid sequence of amino acid Nos. 24 to 34 of SEQ ID NO: 4, CDR2 consisting of the amino acid sequence of amino acid Nos. 50 to 56 of SEQ ID NO: 4, and CDR3 consisting of the amino acid sequence of amino acid Nos. 89 to 97 of SEQ ID NO: 4; and Ab-B is an anti-CLDN6 antibody or an antigen-binding fragment thereof comprising a heavy chain variable region comprising CDR1 consisting of the amino acid sequence of amino acid Nos. 31 to 35 of SEQ ID NO: 6, CDR2 consisting of the amino acid sequence of amino acid Nos. 50 to 65 of SEQ ID NO: 6, and CDR3 consisting of the amino acid sequence of amino acid Nos. 95 to 102 of SEQ ID NO: 6; and a light chain variable region comprising CDR1 consisting of the amino acid sequence of amino acid Nos. 24 to 34 of SEQ ID NO: 8, CDR2 consisting of the amino acid sequence of amino acid Nos. 50 to 56 of SEQ ID NO: 8, and CDR3 consisting of the amino acid sequence of amino acid Nos. 89 to 97 of SEQ ID NO: 8.

[14] The antibody-drug conjugate or a salt thereof according to [12], wherein Ab is an anti-CLDN6 antibody or an antigen-binding fragment thereof selected from the group consisting of Ab-C and Ab-D: Ab-C is an anti-CLDN6 antibody or an antigen-binding fragment thereof comprising a heavy chain variable region consisting of the amino acid sequence of amino acid Nos. 1 to 117 of SEQ ID NO: 2 and a light chain variable region consisting of the amino acid sequence of the amino acid Nos. 1 to 108 of SEQ ID NO: 4; and Ab-D is an anti-CLDN6 antibody or an antigen-binding fragment thereof comprising a heavy chain variable region consisting of the amino acid sequence of amino acid Nos. 1 to 117 of SEQ ID NO: 6 and a light chain variable region consisting of the amino acid sequence of amino acid Nos. 1 to 108 of SEQ ID NO: 8.

[15] The antibody-drug conjugate or a salt thereof according to [12], wherein Ab is an anti-CLDN6 antibody or an antigen-binding fragment thereof selected from the group consisting of Ab1 and Ab2: Ab1 is an anti-CLDN6 antibody comprising a heavy chain consisting of the amino acid sequence of SEQ ID NO: 2 and a light chain consisting of the amino acid sequence of SEQ ID NO: 4; and Ab2 is an anti-CLDN6 antibody comprising a heavy chain consisting of the amino acid sequence of SEQ ID NO: 6 and a light chain consisting of the amino acid sequence of SEQ ID NO: 8.

[16] The antibody-drug conjugate or a salt thereof represented by formula (I), wherein Ab is anti-CLDN6 antibody Ab1; X is NH; $R^1$ is a lower alkyl; $R^2$ is halogen; and $R^3$ is H, $R^4$ is represented by formula (a); ring A is a 5-membered cyclic amine comprising four C and single N; $R^A$ is —$CH_2$—O—; and L is —C(=O)$NHCH_2CH_2$—.

[17] The antibody-drug conjugate or a salt thereof represented by formula (I), wherein Ab is anti-CLDN6 antibody Ab1; X is NH; $R^1$ is a lower alkyl; $R^2$ is H; $R^3$ is H; $R^4$ is represented by formula (b); ring B is a 6-membered cyclic amine comprising two C, single N, two C and single G; G is N; $R^B$ is a haloalkyl; and L is —C(=O)$CH_2CH_2$—.

[18] The antibody-drug conjugate or a salt thereof represented by formula (I), wherein Ab is anti-CLDN6 antibody Ab1; X is NH; $R^1$ is a lower alkyl; $R^2$ is H; $R^3$ is H; $R^4$ is represented by formula (c); $R^C$ is a $C_{3-6}$ cycloalkyl; and L is —C(=O)$CH_2CH_2$— or —C(=O)$NHCH_2CH_2$—.

Examples of specific embodiments of the antibody-drug conjugate or a salt thereof included in the present invention include
an antibody-drug conjugate or a salt thereof comprising Ab1 bound to 1-{3-[(3S)-4-[(4-{[2-amino-4-(pentylamino)-5H-pyrrolo[3,2-d]pyrimidin-5-yl]methyl}-3-methoxyphenyl)methyl]-3-(fluoromethyl)piperazin-1-yl]-3-oxopropyl}-1H-pyrrole-2,5-dione,
an antibody-drug conjugate or a salt thereof comprising Ab2 bound to 1-{3-[(3S)-4-[(4-{[2-amino-4-(pentylamino)-5H-pyrrolo[3,2-d]pyrimidin-5-yl]methyl}-3-methoxyphenyl)methyl]-3-(fluoromethyl)piperazin-1-yl]-3-oxopropyl}-1H-pyrrole-2,5-dione,
an antibody-drug conjugate or a salt thereof comprising Ab1 bound to {(2S)-1-[(4-{[2-amino-7-chloro-4-(pentylamino)-5H-pyrrolo[3,2-d]pyrimidin-5-yl]methyl}-3-methoxyphenyl)methyl]pyrrolidin-2-yl}methyl[2-(2,5-dioxo-2,5-dihydro-1H-pyrrol-1-yl)ethyl]carbamate.
an antibody-drug conjugate or a salt thereof comprising Ab1 bound to N-[(4-{[2-amino-4-(pentylamino)-5H-pyrrolo[3,2-d]pyrimidin-5-yl]methyl}-3-methoxyphenyl)methyl]-N-cyclopropyl-3-(2,5-dioxo-2,5-dihydro-1H-pyrrol-1-yl)propenamide, and
an antibody-drug conjugate or a salt thereof comprising Ab1 bound to 1-{3-[(3R)-4-[(4-{[2-amino-4-(pentylamino)-5H-pyrrolo[3,2-d]pyrimidin-5-yl]methyl}-3-methoxyphenyl)methyl]-3-(fluoromethyl)piperazin-1-yl]-3-oxopropyl}-1H-pyrrole-2,5-dione.

Examples of the antibody-drug conjugate of formula (I) or a salt thereof included in the present invention include

TABLE 1

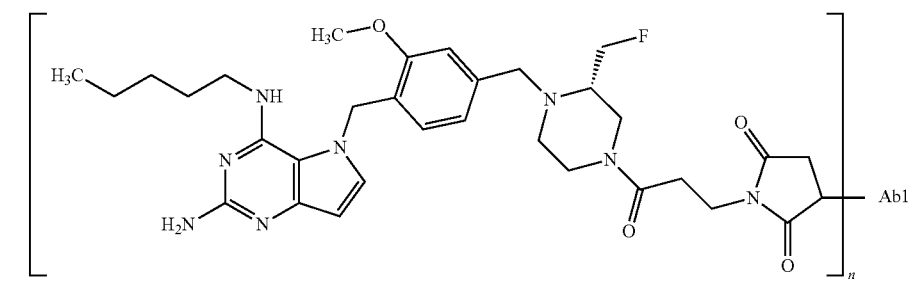

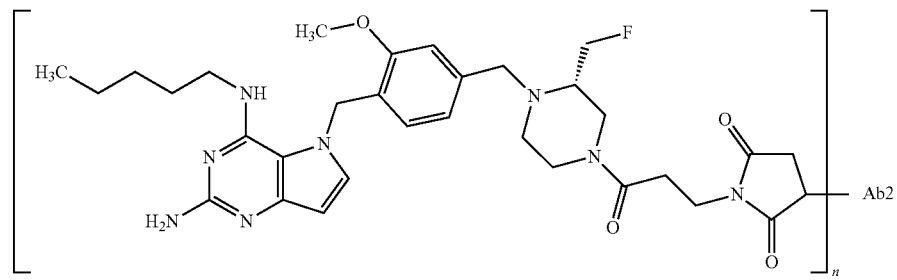

TABLE 1-continued

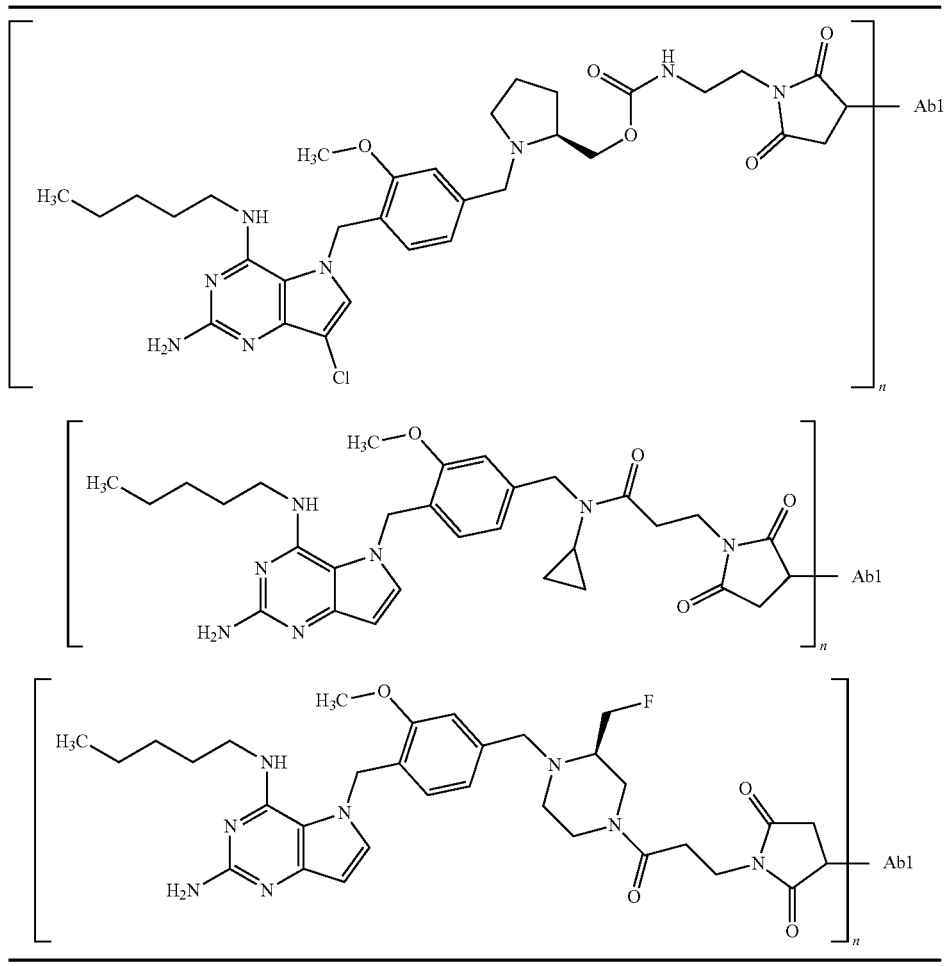

Ab1 is an antibody comprising a heavy chain consisting of the amino acid sequence of SEQ ID NO: 2 and a light chain consisting of the amino acid sequence of SEQ ID NO: 4, Ab2 is an antibody comprising a heavy chain consisting of the amino acid sequence of SEQ ID NO: 6 and a light chain consisting of the amino acid sequence of SEQ ID NO: 8, and n is 1 to 16. As an embodiment, n is 2 to 5.

Embodiment of the Present Invention [2]

Embodiments of a compound of formula (II) of the present invention or a salt thereof will be shown (described) below.

(C1) An embodiment is the compound of formula (II) or a salt thereof, wherein X is S. An embodiment is the compound of formula (II), wherein X is NH.

(C2) An embodiment is the compound of formula (II) or a salt thereof, wherein $R^1$ is a lower alkyl or —CH$_2$-isoxazoldiyl-CH$_3$, wherein if $R^1$ is —CH$_2$-isoxazoldiyl-CH$_3$, X is S. An embodiment is the compound of formula (II) or a salt thereof, wherein $R^1$ is a lower alkyl. An embodiment is the compound of formula (II) or a salt thereof, wherein $R^1$ is a normal pentyl. An embodiment is the compound of formula (II) or a salt thereof wherein $R^1$ is —CH$_2$— isoxazoldiyl-CH$_3$ and X is S. An embodiment is the antibody-drug conjugate of formula (I) or a salt thereof, wherein $R^1$ is —CH$_2$-(5-methylisoxazol-3-yl) and X is S.

(C3) An embodiment is the compound of formula (II) or a salt thereof, wherein $R^2$ is a halogen. An embodiment is the compound of formula (II) or a salt thereof wherein $R^2$ is Br or H. An embodiment is the compound of formula (II) or a salt thereof, wherein $R^2$ is Cl or H. An embodiment is the compound of formula (II) or a salt thereof, wherein $R^2$ is H.

(C4) An embodiment is the compound of formula (II) or a salt thereof, wherein $R^3$ is CH$_3$. An embodiment is the compound of formula (II) or a salt thereof, wherein $R^3$ is H.

(C5) An embodiment is the compound of formula (II) or a salt thereof, wherein $R^{40}$ is a group represented by formula (a1), formula (b1) or formula (c1):

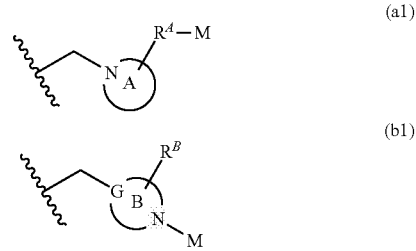

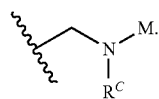

(c1)

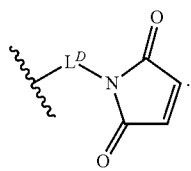

(d)

An embodiment is the compound of formula (II) or a salt thereof, wherein $R^{40}$ is a group represented by formula (a1) or formula (b1). An embodiment is the compound of formula (II) or a salt thereof, wherein $R^{40}$ is a group represented by formula (a1). An embodiment is the compound of formula (II) or a salt thereof, wherein $R^{40}$ is a group represented by formula (b1). An embodiment is the compound of formula (II) or a salt thereof, wherein $R^{40}$ is a group represented by formula (c1).

(C6) An embodiment is the compound of formula (II) or a salt thereof, wherein ring A is a 5-membered cyclic amine comprising four C and single N. An embodiment is the compound of formula (II) or a salt thereof, wherein ring A is pyrrolidine. An embodiment is the compound of formula (II) or a salt thereof, wherein ring A is a 6-membered cyclic amine comprising five C and single N.

(C7) An embodiment is the compound of formula (II) or a salt thereof, wherein ring B is a 6-membered cyclic amine comprising four C, single N and single G, and G is N. An embodiment is the compound of formula (II) or a salt thereof, wherein ring B is a 6-membered cyclic amine comprising two C, single N, two C, and single G. An embodiment is the compound of formula (II) or a salt thereof, wherein ring B is a 6-membered cyclic amine comprising two C, single N, two C, and single G and G is N or CH. An embodiment is the compound of formula (II) or a salt thereof, wherein ring B is a 6-membered cyclic amine comprising two C, single N, two C, and single G and G is N. An embodiment is the compound of formula (II) or a salt thereof, wherein ring B is piperazine.

(C8) An embodiment is the compound of formula (II) or a salt thereof, wherein G is N. An embodiment is the compound of formula (II) or a salt thereof, wherein G is CH.

(C9) An embodiment is the compound of formula (II) or a salt thereof, wherein $R^A$ is —$CH_2O$— or —$C(CH_3)_2O$—. An embodiment is the compound of formula (II) or a salt thereof, wherein $R^A$ is —$CH_2O$—.

(C10) An embodiment is the compound of formula (II) or a salt thereof, wherein $R^B$ is a haloalkyl, $CH_2OH$ or $C(CH_3)_2OH$. An embodiment is the compound of formula (II) or a salt thereof, wherein $R^B$ is a haloalkyl or H, wherein if $R^B$ is H, G is CH. An embodiment is the compound of formula (II) or a salt thereof, wherein $R^B$ is a haloalkyl. An embodiment is the compound of formula (II) or a salt thereof, wherein $R^B$ is monofluoromethyl.

(C11) An embodiment is the compound of formula (II) or a salt thereof, wherein $R^C$ is a $C_{3-6}$ cycloalkyl. An embodiment is the compound of formula (II) or a salt thereof, wherein $R^C$ is a —$CH_2$—$C_{3-6}$ cycloalkyl. An embodiment is the compound of formula (II) or a salt thereof, wherein $R^C$ is —$CH_2$-cyclopropyl. An embodiment is the compound of formula (II) or a salt thereof, wherein $R^C$ is —$CH_2$-cyclobutyl.

(C12) An embodiment is the compound of formula (II) or a salt thereof, wherein M is H. An embodiment is the compound of formula (II) or a salt thereof, wherein M is a group represented by formula (d):

(C13) An embodiment is the compound of formula (II) or a salt thereof, wherein $L^D$ is lower alkylene-, —C(=O) lower alkylene-, —C(=O)NH lower alkylene- or C(=O) lower alkylene-$(OCH_2CH_2)_m$—NH—C(=O)lower alkylene-. An embodiment is the compound of formula (II) or a salt thereof, wherein $L^D$ is -lower alkylene-, —C(=O) lower alkylene- or —C(=O)NH lower alkylene-. An embodiment is the compound of formula (II) or a salt thereof, wherein $L^D$ is —C(=O) lower alkylene- or —C(=O)NH lower alkylene-. An embodiment is the compound of formula (II) or a salt thereof, wherein $L^D$ is —C(=O) lower alkylene-. An embodiment is the compound of formula (II) or a salt thereof, wherein $L^D$ is a non-cleavable linker. An embodiment is the compound of formula (II) or a salt thereof, wherein $L^D$ is —C(=O)NH lower alkylene-. An embodiment is the compound of formula (II) or a salt thereof, wherein $L^D$ is —C(=O)$CH_2CH_2$—. An embodiment is the compound of formula (II) or a salt thereof according to the embodiment of (C13), wherein if $L^D$ is —C(=O)NH lower alkylene-(herein, for example, —C(=O)$NHCH_2CH_2$— is included as a subordinate concept), the —C(=O)NH lower alkylene- is bound to $R^A$ in formula (a1) representing $R^{40}$, wherein $R^A$ is —$CH_2O$— or —$C(CH_3)_2O$—. An embodiment is the compound of formula (II) or a salt thereof according to the embodiment of (C13), wherein if $L^D$ is —C(=O)NH lower alkylene- (herein, for example, —C(=O)$NHCH_2CH_2$— is included as a subordinate concept), the —C(=O)NH lower alkylene- is bound to $R^A$ in formula (a1) represented by $R^{41}$ wherein $R^A$ is —$CH_2O$—.

(C14) An embodiment is the compound of formula (II) or a salt thereof, wherein m is an integer of 4 to 8. An embodiment is the compound of formula (II) or a salt thereof, wherein m is an integer of 4 or 8.

(C15) The compound of formula (II) or a salt thereof for producing an antibody-drug conjugate of formula (I) or a salt thereof.

(C16) The compound of formula (II) or a salt thereof, which is a compatible combination of two or more of the groups according to the above (C1) to (C15).

Examples of the combination according to (C16) include compounds as follows.

[C1] A compound of formula (II) or a salt thereof, wherein X represents S or NH; $R^1$ is a lower alkyl or —$CH_2$-isoxazoldiyl-$CH_3$, wherein if $R^1$ is —$CH_2$-isoxazoldiyl-$CH_3$, X is S; $R^2$ is halogen or H; $R^3$ is $CH_3$ or H; $R^{40}$ is a group represented by formula (a1), formula (b1) or formula (c1); ring A is a 5-membered cyclic amine comprising four C and single N; ring B is a 6-membered cyclic amine comprising four C, single N and single G; G is N or CH; $R^A$ is —$CH_2O$—, —$C(CH_3)_2O$—, —O— or —$CH_2NH$—, wherein if $R^A$ is —O— or —$CH_2NH$—, then X is S; $R^2$ is halogen; or $R^3$ is $CH_3$; $R^B$ is haloalkyl, $CH_2OH$, $C(CH_3)_2OH$,OH, $CH_2NH_2$ or H, wherein if $R^B$ is OH, $CH_2NH_2$ or H, then G is CH; X is S; $R^2$ is halogen; or $R^3$ is $CH_3$; $R^C$ is $C_{3\text{-}6}$ cycloalkyl or —$CH_2$—$C_{3-6}$ cycloalkyl, M is H, or a group represented by formula (d), $L^D$ is -lower alkylene-, —C(=O) lower alkylene-, —C(=O)NH lower alkylene-, —C(=O) lower alkylene-(OCH$_2$CH$_2$)$_m$—NH—C(=O) lower alkylene-, —(CH$_2$CH$_2$O)$_m$—C(=O) lower alkylene-, or —C(=O)-cyclohexandiyl-lower alkylene-, m is an integer of 1 to 10.

[C1a] The compound of formula (II) or a salt thereof, wherein ring A is a 5-membered cyclic amine comprising four C and single N; and a ring B is a 6-membered cyclic amine comprising two C, single N, two C and single G wherein G is N.

[C2] The compound of formula (II) or a salt thereof according to [C1] or [C1a], wherein $R^A$ is —CH$_2$O— or —C(CH$_3$)$_2$O—; and $R^B$ is a haloalkyl, CH$_2$OH or C(CH$_3$)$_2$OH.

[C3] The compound of formula (II) or a salt thereof according to [C2], wherein $L^D$ is -lower alkylene-, —C(=O) lower alkylene-, —C(=O)NH lower alkylene- or —C(=O) lower alkylene-(OCH$_2$CH$_2$)$_m$—NH—C(=O) lower alkylene-, and m is an integer of 4 to 8.

[C4] The compound of formula (II) or a salt thereof according to [C2], wherein $L^D$ is —C(=O) lower alkylene- or —C(=O)NH lower alkylene-, or a salt thereof.

[C5] The compound of formula (II) or a salt thereof according to [C3] or [C4], wherein X is NH; $R^1$ is a lower alkyl; $R^2$ is halogen or H; and $R^3$ is H.

[C6] A compound of formula (II) or a salt thereof, wherein X is NH, $R^1$ is a lower alkyl, $R^2$ is Cl or H, $R^3$ is H, $R^{41}$ is formula (a1), formula (b1) or formula (c1), ring A is a 5-membered cyclic amine comprising four C and single N, ring B is a 6-membered cyclic amine comprising four C, single N and single G, G is N, $R^A$ is —CH$_2$O—, $R^B$ is a haloalkyl, $R^c$ is a C$_{3-6}$ cycloalkyl, M is a group represented by formula (d) and $L^D$ is —C(=O)CH$_2$CH$_2$—.

[C6a] The compound of formula (II) or a salt thereof according to [C5], wherein X is NH; $R^1$ is a lower alkyl; $R^2$ is Cl or H; $R^3$ is H; $R^{40}$ is represented by formula (a1), formula (b1), or formula (c1); ring A is a 5-membered cyclic amine comprising four C and single N; ring B is a 6-membered cyclic amine comprising two C, single N, two C and single G and G is N; $R^A$ is —CH$_2$—O—; $R^B$ is a haloalkyl; $R^c$ is a C$_{3-6}$ cycloalkyl; M is a group represented by formula (d); and $L^D$ is —C(=O)CH$_2$CH$_2$—.

[C7] The compound of formula (II) or a salt thereof according to [C6a], wherein X is NH; $R^1$ is a lower alkyl; $R^2$ is H; $R^3$ is H; $R^{40}$ is represented by formula (b1); ring B is a 6-membered cyclic amine comprising two C, single N, two C and single G wherein G is N; $R^B$ is a haloalkyl; and $L^D$ is —C(=O)CH$_2$CH$_2$—.

[C8] A compound of formula (II) or a salt thereof, wherein X is NH, $R^1$ is a lower alkyl, $R^2$ is halogen, $R^3$ is H, $R^{40}$ is formula (a1), ring A is a 5-membered cyclic amine comprising four C and single N, $R^A$ is —CH$_2$O—, and $L^D$ is —C(=O)NHCH$_2$CH$_2$—.

[C9] A compound of formula (II) or a salt thereof, wherein X is NH, $R^1$ is a lower alkyl, $R^2$ is H, $R^3$ is H, $R^{41}$ is formula (c), $R^c$ is a C$_{3-6}$ cycloalkyl, and $L^D$ is —C(=O)CH$_2$CH$_2$—.

[C10] A compound of formula (II) or a salt thereof, wherein X is NH, $R^1$ is a lower alkyl, $R^2$ is Cl or H, $R^3$ is H, $R^{41}$ is formula (a1), formula (b1) or formula (c1), ring A is a 5-membered cyclic amine comprising four C and single N, ring B is a 6-membered cyclic amine comprising four C, single N and single G, G is N, $R^A$ is —CH$_2$O—, $R^B$ is a haloalkyl, $R^c$ is a C$_{3-6}$ cycloalkyl, M is a group represented by formula (d), $L^D$ is —C(=O)CH$_2$CH$_2$— or —C(=O)NHCH$_2$CH$_2$—, wherein if $L^D$ is —C(=O)NHCH$_2$—CH$_2$— the C(=O)NHCH$_2$CH$_2$— is bound to $R^A$ in formula (a1) representing $R^{4'}$ and $R^A$ is —CH$_2$O—.

Examples of the compound or a salt thereof according to the present invention include:

5-[(4-{[(2S)-2-(fluoromethyl)piperazin-1-yl]methyl}-2-methoxyphenyl)methyl]-N$^4$-pentyl-5H-pyrrolo[3,2-d]pyrimidine-2,4-diamine or a salt thereof, 5-[(4-{[(3R)-3-(fluoromethyl)piperazin-1-yl]methyl}-2-methoxyphenyl)methyl]-N$^4$-pentyl-5H-pyrrolo[3,2-d]pyrimidine-2,4-diamine or a salt thereof, 5-({4-[(cyclopropylamino)methyl]-2-methoxyphenyl}methyl)-N$^4$-pentyl-5H-pyrrolo[3,2-d]pyrimidine-2,4-diamine or a salt thereof, {(2S)-1-[(4-{[2-amino-7-chloro-4-(pentylamino)-5H-pyrrolo[3,2-d]pyrimidin-5-yl]methyl}-3-methoxyphenyl)methyl]pyrrolidin-2-yl}methanol or a salt thereof, 5-({2-methoxy-4-[(piperidin-4-yl)methyl]phenyl}methyl)-N$^4$-pentyl-5H-pyrrolo[3,2-d]pyrimidine-2,4-diamine or a salt thereof, 5-[(4-{[(2R)-2-(fluoromethyl)piperazin-1-yl]methyl}-2-methoxyphenyl)methyl]-N$^4$-pentyl-5H-pyrrolo[3,2-d]pyrimidine-2,4-diamine or a salt thereof, 5-[(4-{[(cyclobutylmethyl)amino]methyl}-2-methoxyphenyl)methyl]-N$^4$-pentyl-5H-pyrrolo[3,2-d]pyrimidine-2,4-diamine or a salt thereof, 1-{3-[(3S)-4-[(4-{[2-amino-4-(pentylamino)-5H-pyrrolo[3,2-d]pyrimidin-5-yl]methyl}-3-methoxyphenyl)methyl]-3-(fluoromethyl)piperazin-1-yl]-3-oxopropyl}-1H-pyrrole-2,5-dione or a salt thereof, {(2S)-1-[(4-{[2-amino-7-chloro-4-(Pentylamino)-5H-pyrrolo[3,2-d]pyrimidin-5-yl]methyl}-3-methoxyphenyl)methyl]pyrrolidin-2-yl}methyl[2-(2,5-dioxo-2,5-dihydro-1H-pyrrol-1-yl)ethyl]carbamate or a salt thereof, N-[(4-{[2-amino-4-(pentylamino)-5H-pyrrolo[3,2-d]pyrimidin-5-yl]methyl}-3-methoxyphenyl)methyl]-N-cyclopropyl-3-(2,5-dioxo-2,5-dihydro-1H-pyrrol-1-yl)propenamide or a salt thereof, 1-{3-[(3R)-4-[(4-{[2-amino-4-(pentylamino)-5H-pyrrolo[3,2-d]pyrimidin-5-yl]methyl}-3-methoxyphenyl)methyl]-3-(fluoromethyl)piperazin-1-yl]-3-oxopropyl}-1H-pyrrole-2,5-dione or a salt thereof.

Examples of the compound or a salt thereof according to the present invention include:

5-[(4-{[(2S)-2-(fluoromethyl)piperazin-1-yl]methyl}-2-methoxyphenyl)methyl]-N$^4$-pentyl-5H-pyrrolo[3,2-d]pyrimidine-2,4-diamine, 5-[(4-{[(3R)-3-(fluoromethyl)piperazin-1-yl]methyl}-2-methoxyphenyl)methyl]-N$^4$-pentyl-5H-pyrrolo[3,2-d]pyrimidine-2,4-diamine trifluoroacetate, 5-({4-[(cyclopropylamino)methyl]-2-methoxyphenyl}methyl)-N$^4$-pentyl-5H-pyrrolo[3,2-d]pyrimidine-2,4-diamine, {(2S)-1-[(4-{[2-amino-7-chloro-4-(pentylamino)-5H-pyrrolo[3,2-d]pyrimidin-5-yl]methyl}-3-methoxyphenyl)methyl]pyrrolidin-2-yl}methanol, 5-({2-methoxy-4-[(piperidin-4-yl)methyl]phenyl}methyl)-N$^4$-pentyl-5H-pyrrolo[3,2-d]pyrimidine-2,4-diamine, 5-[(4-{[(2R)-2-(fluoromethyl)piperazin-1-yl]methyl}-2-methoxyphenyl)methyl]-N$^4$-pentyl-5H-pyrrolo[3,2-d]pyrimidine-2,4-diamine, 5-[(4-{[(cyclobutylmethyl)amino]methyl}-2-methoxyphenyl)methyl]-N$^4$-pentyl-5H-pyrrolo[3,2-d]pyrimidine-2,4-diamine, 1-{3-[(3S)-4-[(4-{[2-amino-4-(pentylamino)-5H-pyrrolo[3,2-d]pyrimidin-5-yl]methyl}-3-methoxyphenyl)methyl]-3-(fluoromethyl)piperazin-1-yl]-3-oxopropyl}-1H-pyrrole-2,5-dione trifluoroacetate, {(2S)-1-[(4-{[2-amino-7-chloro-4-(Pentylamino)-5H-pyrrolo[3,2-d]pyrimidin-5-yl]methyl}-3-methoxyphenyl)

methyl]pyrrolidin-2-yl}methyl[2-(2,5-dioxo-2,5-di-hydro-1H-pyrrol-1-yl)ethyl]carbamate,
N-[(4-{[2-amino-4-(pentylamino)-5H-pyrrolo[3,2-d]pyrimidin-5-yl]methyl}-3-methoxyphenyl)methyl]-N-cyclopropyl-3-(2,5-dioxo-2,5-dihydro-1H-pyrrol-1-yl)propanamide trifluoroacetate, and
1-{3-[(3R)-4-[(4-{[2-amino-4-(pentylamino)-5H-pyrrolo[3,2-d]pyrimidin-5-yl]methyl}-3-methoxyphenyl)methyl]-3-(fluoromethyl)piperazin-1-yl]-3-oxopropyl}-1H-pyrrole-2,5-dione trifluoroacetate.

Examples of the compound of formula (II) or a salt thereof according to (C16), wherein M is H included in the present invention include:
5-[(4-{[(2S)-2-(fluoromethyl)piperazin-1-yl]methyl}-2-methoxyphenyl)methyl]-N$^4$-pentyl-5H-pyrrolo[3,2-d]pyrimidine-2,4-diamine,
5-[(4-{[(3R)-3-(fluoromethyl)piperazin-1-yl]methyl}-2-methoxyphenyl)methyl]-N$^4$-pentyl-5H-pyrrolo[3,2-d]pyrimidine-2,4-diamine trifluoroacetate,
5-({4-[(cyclopropylamino)methyl]-2-methoxyphenyl}methyl)-N$^4$-pentyl-5H-pyrrolo[3,2-d]pyrimidine-2,4-diamine,
(2S)-1-[(4-{[2-amino-7-chloro-4-(pentylamino)-5H-pyrrolo[3,2-d]pyrimidin-5-yl]methyl}-3-methoxyphenyl)methyl]pyrrolidin-2-yl}methanol,
5-({2-methoxy-4-[(piperidin-4-yl)methyl]phenyl}methyl)-N$^4$-pentyl-5H-pyrrolo[3,2-d]pyrimidine-2,4-diamine,
5-[(4-{[(2R)-2-(fluoromethyl)piperazin-1-yl]methyl}-2-methoxyphenyl)methyl]-N$^4$-pentyl-5H-pyrrolo[3,2-d]pyrimidine-2,4-diamine, and
5-[(4-{[(cyclobutylmethyl)amino]methyl}-2-methoxyphenyl)methyl]-N$^4$-pentyl-5H-pyrrolo[3,2-d]pyrimidine-2,4-diamine.

Embodiments of the compound of formula (II) or a salt thereof of the present invention is described below.

(C17) A compound or a salt thereof, wherein M of the group represented by formula (a1), formula (b1), or formula (c1) in $R^{41}$ is H in a compound of formula (II) or a salt thereof.

(C18) A antibody-drug conjugate or a salt thereof, wherein an antibody is bound via a linker to the M position of the group represented by formula (a1), formula (b1), or formula (c1) in $R^{40}$ in a compound of formula (II) or a salt thereof.

(C19) An antibody-drug conjugate or a salt thereof according to (C18), wherein the antibody is an anti-TAA antibody or an antigen-binding fragment thereof.

(C20) An antibody-drug conjugate or a salt thereof according to (C18), wherein the antibody is an anti-CLDN6 antibody or an antigen-binding fragment thereof.

An antibody-drug conjugate of formula (I) or a salt thereof can provide an antibody-drug conjugate by using a compound of formula (II) or a salt thereof, an optional anti-TAA antibody and an optional non-cleavable linker in combination.

An antibody-drug conjugate of formula (I) or a salt thereof and a compound of formula (II) or a salt thereof may have tautomers and geometric isomers depending on the type of substituent. An antibody-drug conjugate of formula (I) or a salt thereof is sometimes represented in only one isomeric form, in the specification. However, the present invention includes other isomeric forms. Isolated isomers or a mixture of isomers are also included.

An antibody-drug conjugate of formula (I) or a salt thereof and a compound of formula (II) or a salt thereof sometimes have a chiral center or axial chirality. Based on this, enantiomers (optical isomers) can be present. An antibody-drug conjugate of formula (I) or a salt thereof includes any one of isolated individual (R)-form, (S)-form enantiomers and a mixture of these (including a racemic mixture or a non-racemic mixture). In an embodiment, an enantiomer is "stereochemically pure". The "stereochemically pure" refers to a degree of purity to the extent that those skilled in the art recognize as being substantially stereochemically pure. As an embodiment, an enantiomer is a compound having a stereochemical purity of, for example, 90% ee (enantiomeric excess) or more, 95% ee or more, 98% ee or more, or 99% ee or more.

The salts of an antibody-drug conjugate of formula (I) and a compound of formula (II) refer to pharmaceutically acceptable salts of an antibody-drug conjugate of formula (I). Sometimes, acid addition salts may be formed depending on the type of substituent. Examples of the acid addition salts include acid addition salts with inorganic acids such as hydrochloric acid, hydrobromic acid, hydroiodic acid, sulfuric acid, nitric acid and phosphoric acid; and organic acids formic acid, acetic acid, propionic acid, oxalic acid, malonic acid, succinic acid, fumaric acid, maleic acid, lactic acid, malic acid, mandelic acid, tartaric acid, dibenzoyl tartaric acid, ditoluoyl tartaric acid, citric acid, methanesulfonic acid, ethane-sulfonic acid, benzenesulfonic acid, p-toluene-sulfonic acid, aspartic acid, and glutamic acid.

The present invention further includes hydrates, solvates, and crystal polymorphic substances of an antibody-drug conjugate of formula (I) and a salt thereof or a salt thereof, and a compound of formula (II) or a salt thereof.

The present invention also includes all of the antibody-drug conjugates of formula (I) or salts thereof, and the compounds of formula (II) or salts thereof labeled with one or more pharmaceutically acceptable radioactive or non-radioactive isotopes. Examples of suitable isotopes to be used as the isotope label for the compound of the present invention include hydrogen (e.g., $^2$H and $^3$H), carbon (e.g., $^{11}$C, $^{13}$C and $^{14}$C), nitrogen (e.g., $^{13}$N and $^{15}$N), oxygen (e.g., $^{15}$O, $^{17}$O and $^{18}$O), fluorine (e.g., $^{18}$F), chlorine (e.g., $^{36}$Cl), iodine (e.g., $^{123}$I and $^{125}$I), phosphorus (e.g., $^{32}$P) and sulfur (e.g., $^{35}$S) isotopes. The compounds, drugs and/or substrates labeled with an isotope according to the invention of the present application can be used for studies such as tissue distribution (study). For example, radioisotopes such as tritium ($^3$H) and carbon-14 ($^{14}$C) are easy to label and easily detected, and thus, used for this purpose. Replacement for a heavy isotope such as hydrogen deuterium ($^2$H) improves metabolic stability, and is sometimes beneficial from a therapeutic point of view (for example, in vivo half-life increases, required dose decreases and drug interactions decrease).

Positron emitting isotopes (e.g., $^{11}$C, $^{18}$F, $^{15}$O and $^{13}$N) can be used in positron emission tomography (PET) tests for determining substrate receptor occupancy. Compounds labeled with an isotope according to the present invention can be usually prepared in accordance with a technique commonly known to those skilled in the art, or by using an appropriate isotope-labeled reagent in place of a non-labeled reagent, by the same process and the like as in Examples or Production Examples.

Embodiment of the Present Invention [3]

An embodiment of an antibody according to [3] in the present invention will be shown (described) below.

(AB1) An anti-CLDN6 antibody or an antigen-binding fragment thereof comprising a heavy chain variable region consisting of the amino acid sequence of amino acid Nos. 1 to 117 of SEQ ID NO: 2 and a light chain variable region consisting of the amino acid Nos. 1 to 108 of SEQ ID NO: 4; or an anti-CLDN6 antibody or an antigen-binding fragment thereof comprising a heavy chain variable region consisting of the amino acid sequence of amino acid Nos. 1 to 117 of SEQ ID NO: 6 and a light chain variable region consisting of the amino acid Nos. 1 o 108 of SEQ ID NO: 8.

(AB2) An anti-CLDN6 antibody comprising a heavy chain consisting of the amino acid sequence of SEQ ID NO: 2 and a light chain consisting of the amino acid sequence of SEQ ID NO: 4, or an anti-CLDN6 antibody comprising a heavy chain consisting of the amino acid sequence of SEQ ID NO: 6, and a light chain consisting of an amino acid of SEQ ID NO: 8.

(AB3) An anti-CLDN6 antibody according to (AB2) having post-translational modification.

(AB4) An anti-CLDN6 antibody comprising a heavy chain consisting of the amino acid sequence of SEQ ID NO: 2 having post-translational modification and a light chain consisting of the amino acid sequence of SEQ ID NO: 4, or an anti-CLDN6 antibody comprising a heavy chain consisting of the amino acid sequence of SEQ ID NO: 6 and having post-translational modification and a light chain consisting of an amino acid of SEQ ID NO: 8.

(AB5) An antibody-drug conjugate containing an anti-CLDN6 antibody according to any one of (AB1) to (AB4) or an antigen-binding fragment thereof.

In the antibody-drug conjugate according to (AB5) containing an anti-CLDN6 antibody of the present invention, a drug known in the technical field other than a TLR7/8 dual agonist compound of the present invention and a linker can be used.

(Process)

An antibody-drug conjugate of formula (I) and a salt thereof and a compound of formula (II) or a salt thereof can be produced by applying (employing) various synthetic methods known in the technical field based on the basic structures of the conjugate and compound or types of substituents. In synthesis, depending on the type of functional group, it is sometimes effective to replace the functional group with an appropriate protecting group (that can be easily converted into the functional group) during a step of forming an intermediate from a starting material, in view of processing technology. Examples of the protecting group include those disclosed in, "Greene's Protective Groups in Organic Synthesis written by Wuts (P. G. M.) and Greene (T. W. Greene) (4th edition, 2006)". The protecting group may be appropriately selected depending on individual reaction conditions. In the method using a protecting group, a reaction is carried out by introducing the protecting group, and then, the protecting group is removed to obtain a desired compound.

Now, typical methods for producing an antibody-drug conjugate of formula (I) or a salt thereof and a compound of formula (II) or a salt thereof will be described below. Each production method can be carried out with reference to the documents attached hereto. Note that, the production methods of the present invention are not limited to the following examples.

(First Process for Antibody-Drug Conjugate)

An antibody-drug conjugate included in the present invention can be produced by the following process.

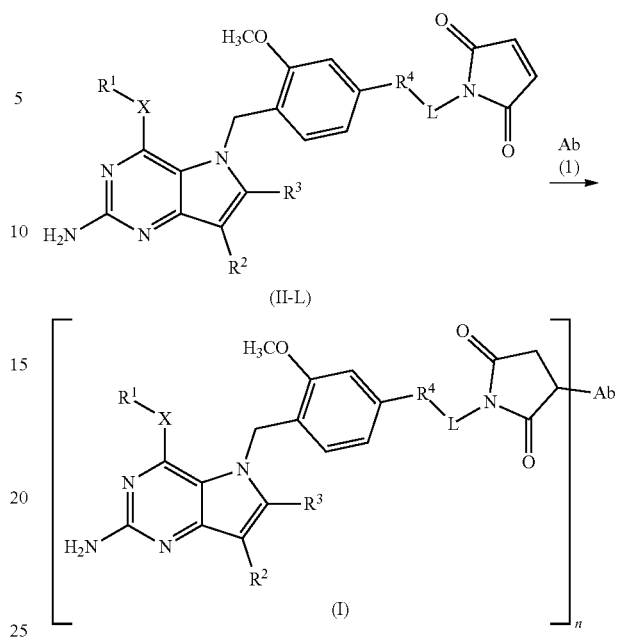

wherein Ab is an antibody or an antigen-binding fragment thereof.

The antigen-drug conjugate (I) of the present invention can be produced by the Michael addition reaction of an antibody or an antigen-binding fragment thereof (1) and a compound (II-L) of the present invention. More specifically, the antibody-drug conjugate (I) of the present invention can be produced by reducing disulfide bonds between L chains and H chains and/or hinge region of the antibody or an antigen-binding fragment thereof (1) and adding the thiol moiety generated to compound (II-L) in accordance with the Michael addition (reaction). Usually, an antibody is incubated in a neutral to acidic buffer in the presence of a reducing agent at 20 to 37° C. for 1 to 24 hours, and then, compound (II-L) is added to the buffer and the incubation continues. As the solution (buffer), a solution containing a phosphate buffer is used. As the phosphate buffer, for example, disodium hydrogen phosphate (buffer) is used. For example, a PBS6.2/EDTA solution is used. As the reducing agent, for example, TCEP is used.

(First Process for Drug-Linker Conjugate)

A drug-linker conjugate can be produced in accordance with the following process. A drug-linker conjugate (i.e., a compound represented by formula (II), wherein M is a group represented by formula (d)) is used for producing an antibody-drug conjugate of formula (I).

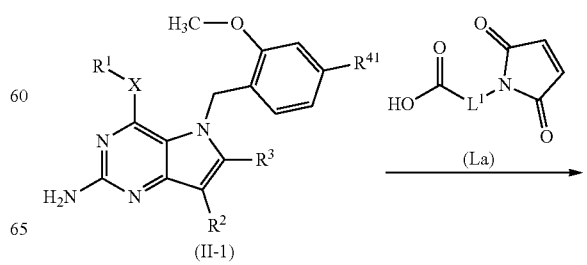

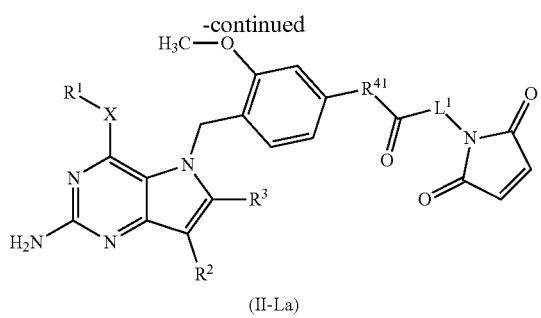

(II-La)

wherein
$R^{41}$ is a group represented by $R^{41}$ wherein M is H; $R^{41\prime}$ is a divalent group represented by $R^{40}$ wherein H of M is replaced; and —(C=O)-$L^1$ represents —C(=O) lower alkylene-, —C(=O)NH lower alkylene-, —C(=O) lower alkylene-(OCH$_2$CH$_2$)$_m$—NH—C(=O) lower alkylene-, or —C(=O)-cyclohexandiyl-lower alkylene- in $L^D$. The same applies to the followings.

Compound (II—La) of the present invention is compound (II) of the present invention, wherein L is —C(=O)$L^1$. compound (II—La) of the present invention can be produced by an amidation reaction of compound (II-1) and compound (La).

In the amidation reaction, compound (II-1) of the present invention and compound (La) are used in equal amounts or either one of them is used excessively. A mixture of these compounds is stirred in an inert solvent in the presence of a condensing agent under cooling to heating (as an embodiment, −20° C. to 60° C.) usually for 0.1 hour to 5 days. Examples of the solvent include an aromatic hydrocarbon such as benzene, toluene or xylene; a halogenated hydrocarbon such as dichloromethane, 1,2-dichlooethane or chloroform; an ether such as diethyl ether, THF, 1,4-dioxane or dimethoxyethane; DMF, DMSO, EtOAc, MeCN and water, and a mixture of these. Examples of the condensing agent include, but are not limited to, HATU, 1-(3-dimethylaminopropyl)-3-ethylcarbodiimide, dicyclohexylcarbodiimide, 1,1'-carbonyldiimidazole, diphenylphosphate azide and phosphorus oxychloride. It is sometimes favorable for the reaction to use an additive (for example, 1-hydroxybenzotriazole). It is sometimes beneficial that a reaction is performed in the presence of an organic base such as triethylamine, DIPEA or N-methylmorpholine or an inorganic base such as potassium carbonate, sodium carbonate or potassium hydroxide, in order for the reaction to smoothly proceed.

A method of converting a carboxylic acid (La) into a reactive derivative and reacting the reactive derivative with an amine of compound (II-1), can be used. Examples of the reactive derivative of a carboxylic acid include an acid halide, which is obtained by a reaction with a halogenating agent such as phosphorus oxychloride and thionyl chloride; a mixed acid anhydride, which is obtained by a reaction with, e.g., isobutyl chloroformate; and an active ester obtained by condensation with, e.g., 1-hydroxybenzotriazole. The reactions of a reactive derivative and compound (II-1) can be carried out in an inert solvent, such as a halogenated hydrocarbon, an aromatic hydrocarbon and an ether, under cooling to heating, preferably, −20° C. to 60° C.

[Documents] "Organic Functional Group Preparations" written by S. R. Sandler and W. Karo, Second edition, Vol. 1, Academic Press Inc., 1991. "Experimental Chemistry Course edited by the Chemical Society of Japan (5th edition)", Vol. 16 (2005) (Maruzen Co., Ltd.).

(Second Process for Drug-Linker Conjugate)

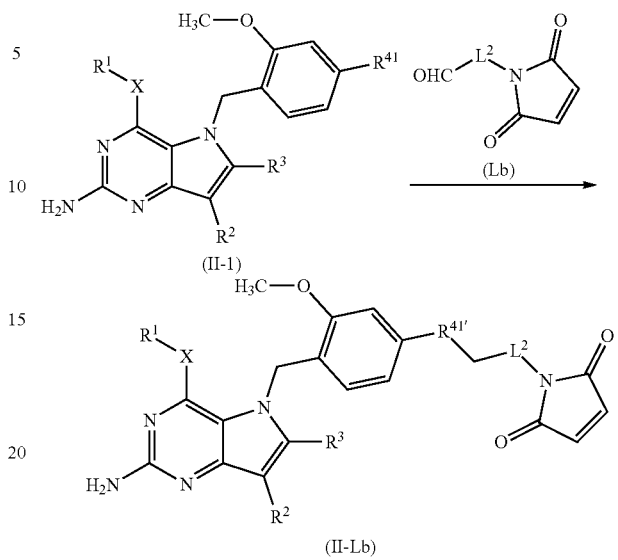

wherein $L^2$ represents a lower alkylene obtained by removing —CH$_2$— from a group represented by L. The same applies to the followings.

Compound (II-Lb) of the present invention is compound (II) of the present invention, wherein L is represented by —CH$_2$-$L^2$. compound (II-Lb) of the present invention can be produced by a reductive amination reaction of compound (II-1) and compound (Lb).

In the reaction, compound (II-1) of the present invention and compound (Lb) are used in equal amounts or either one of them is used excessively. A mixture of these compounds is stirred in an inert solvent in the presence of a condensing agent at −45° C. to under reflux, preferably 0° C. to room temperature, usually for 0.1 hour to 5 days. Examples of the solvent include, but are not particularly limited to, an alcohol such as methanol and ethanol; an ether such as diethyl ether, THF, 1,4-dioxane and dimethoxyethane; and a mixture of these. Examples of the reducing agent include sodium cyanoborohydride, sodium triacetoxyborohydride and sodium borohydride. It is sometimes preferable to perform a reaction in the presence of a dehydrating agent such as molecular sieves or an acid such as acetic acid, hydrochloric acid, and titanium (IV) isopropoxide complex. Depending on the reaction, an imine is produced by condensation of compound (II-1) and compound (Lb) and can be isolated as a stable intermediate. In this case, compound (II-Lb) can be produced by a reduction reaction of the imine intermediate. In place of the treatment with a reducing agent, a reduction catalyst (for example, palladium carbon or Raney nickel) can be used for a reaction performed in a solvent, such as methanol, ethanol and EtOAc, in the presence or absence of an acid such as acetic acid and hydrochloric acid. In this case, the reaction is preferably performed at normal pressure to 50 atm. in a hydrogen atmosphere under cooling to heating.

[Documents] "Comprehensive Organic Functional Group Transformations II", written by A. R. Katritzky and R. J. K. Taylor Vol. 2, Elsevier Pergamon, 2005. "Experimental Chemistry Course edited by the Chemical Society of Japan (5th edition)", Vol. 14 (2005) (Maruzen Co., Ltd.).

(Third Process for Drug-Linker Conjugate)

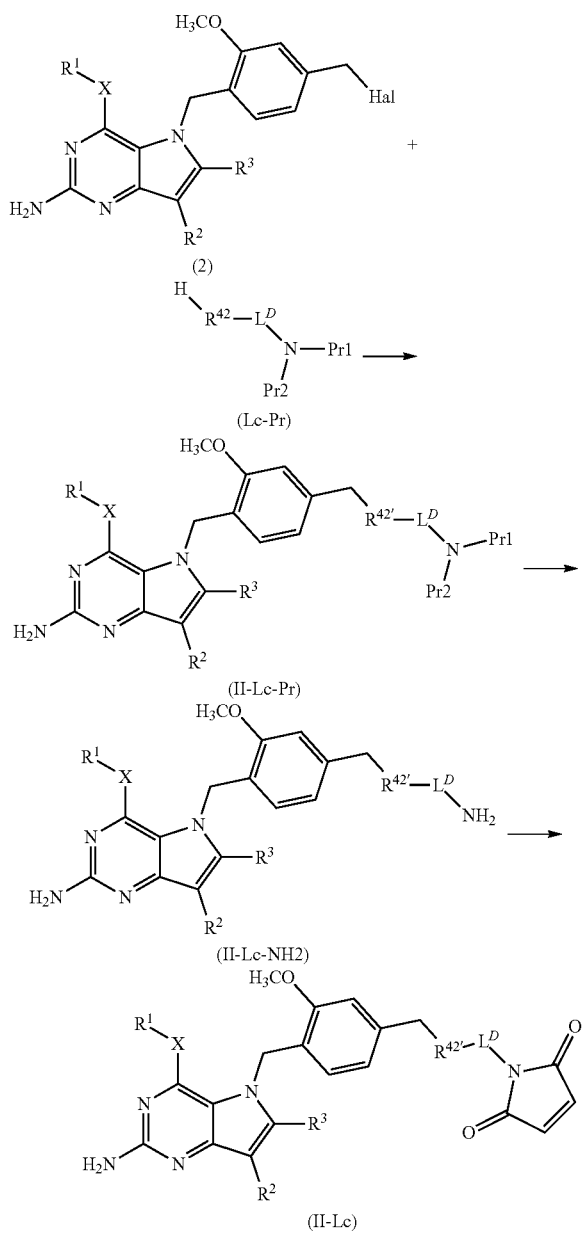

wherein $R^{42}$ is a group obtained by removing —$CH_2$— from the group represented by formula (a1), formula (b1) or formula (c1) in $R^{40}$; and M indicates a bond; in ring B, G is N. $R^{42'}$ represents a divalent group obtained by removing H from NH in $R^{42}$; Hal represents a leaving group. Pr1 is a protecting group; Pr2 is H, or Pr1 and Pr2 join together to serve as a protecting group. The same applies to the following.

Compound (II-Lc) of the present invention can be produced by a cyclization reaction of compound (II-Lc-NH2), which is obtained by deprotecting compound (II-Lc-Pr) produced by reacting compound (2) and compound (Lc-Pr). Herein, examples of the leaving group include a halogen atom, a methanesulfonyloxy group and a p-toluenesulfonyloxy group. Examples of the protecting group Pr1 include tert-butoxycarbonyl. Examples of the protecting group formed by joining Pr1 and Pr2 together include phthalimide. In the reaction for obtaining compound (II-Lc-Pr), compound (2) and compound (Lc-Pr) are used in equal amounts or either one of them is used excessively. A mixture of these compounds is stirred in an inert solvent or without using a solvent under cooling to heat reflux, preferably 0° C. to 80° C., usually for 0.1 hour to 5 days. Examples of the solvent include aromatic hydrocarbons such as benzene, toluene and xylene; ethers such as diethyl ether, THF, 1,4-dioxane and dimethoxyethane; halogenated hydrocarbons such as dichloromethane, 1,2-dichloroethane and chloroform; DMF, DMSO, EtOAc, MeCN and a mixture of these. It is sometimes beneficial that a reaction is performed in the presence of an organic base such as triethylamine, DIPEA or N-methylmorpholine or an inorganic base such as cesium carbonate, potassium carbonate, sodium carbonate or potassium hydroxide, in order for the reaction to smoothly proceed.

[Documents] "Organic Functional Group Preparations" written by S. R. Sandler and W. Karo, Second edition, Vol. 1, Academic Press Inc., 1991. "Experimental Chemistry Course edited by the Chemical Society of Japan (5th edition)", Vol. 14 (2005) (Maruzen Co., Ltd.).

Deprotection of compound (II-Lc-Pr) for obtaining compound (II-Lc-NH2) can be carried out in the conditions commonly employed.

Compound (II-Lc) can be produced from compound (II-Lc-NH2) by adding N-methoxycarbonylmaleimide to compound (II-Lc-NH2) in a solvent in the presence of a base and stirring the mixture obtained at room temperature, for 0.5 to 4 hours. Examples of the solvent include aromatic hydrocarbons such as benzene, toluene and xylene; ethers such as diethyl ether, THF, 1,4-dioxane and dimethoxyethane; and DMF. Examples of the base that is used include a sodium hydrogen carbonate aqueous solution.

(First Process for Drug)

A drug (more specifically, a compound represented by formula (II), wherein M is H) can be produced by the following process.

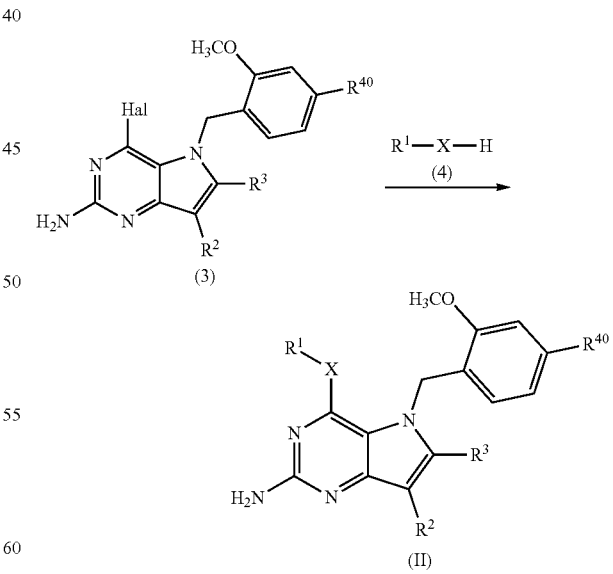

Compound (II) of the present invention can be produced by a reaction of compound (3) and compound (4). In the reaction, compound (3) and compound (4) are used in equal amounts or either one of them is used excessively. The mixture of these is stirred in an inert solvent or without using a solvent, under cooling to under heat reflux under irradiation of microwave at 0° C. to 100° C. usually for 0.1 hour to 5 days. Examples of the solvent include aromatic hydrocarbons such as benzene, toluene and xylene; ethers such as diethyl ether, THF, 1,4-dioxane and dimethoxyethane; DMF, DMSO, EtOAc, MeCN and a mixture of these. It is sometimes beneficial that a reaction is performed in the presence of an organic base, such as triethylamine, DIPEA or N-methylmorpholine, or an inorganic base, such as potassium carbonate, sodium carbonate or potassium hydroxide, in order for the reaction to smoothly proceed.

[Documents] "Organic Functional Group Preparations" written by S. R. Sandler and W. Karo, Second edition, Vol. 1, Academic Press Inc., 1991. "Experimental Chemistry Course edited by the Chemical Society of Japan (5th edition)", Vol. 14 (2005) (Maruzen Co., Ltd.).

Note that, in the above step, a reaction may be carried out by using not $R^{40}$ but $R^{40}$ having a protecting group bound thereto and finally removing the protecting group.

(Second Process for Drug)

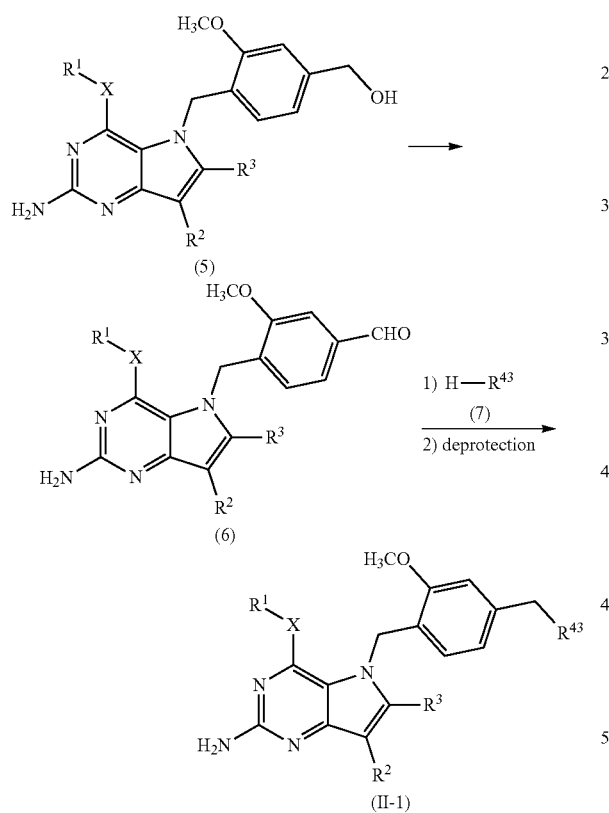

wherein, $R^{43}$ is a group obtained by removing —$CH_2$— from the group represented by formula (a1), formula (b1) or formula (c1) in $R^{40}$; G is N; and M represents a protecting group or H.

Compound (II-1) of the present invention can be produced by oxidizing compound (5) to obtain compound (6) and subjecting compound (6) and compound (7) to a reductive amination reaction.

In the oxidation reaction of compound (5), compound (5) is treated with an equal or excessive amount of an oxidant in an inert solvent, under cooling to heating, preferably at −20° C. to 80° C. usually for 0.1 hour to 3 days. Examples of the solvent that is used herein include, but are not particularly limited to, ethers such as diethyl ether, THF, 1,4-dioxane and dimethoxyethane; halogenated hydrocarbons such as dichloromethane, 1,2-dichloroethane and chloroform; aromatic hydrocarbons such as benzene, toluene and xylene; DMF, DMSO, EtOAc, water, and a mixture of these. Examples of the oxidant that is suitably used include hydrogen peroxide, cumene hydroperoxide, peracetic acid, perbenzoic acid, m-chloroperbenzoic acid, oxone, active manganese dioxide, chromic acid, potassium permanganate and sodium periodate. In the reaction, DMSO oxidation such as Swern oxidation or oxidation using a Dess-Martin reagent is suitably used.

[Document] "Comprehensive Organic Synthesis" written by B. M. Trost, Vol. 7, 1991; "Oxidation in Organic Chemistry (ACS Monograph: 186)" written by M. Hudlicky, A C S, 1990; "Experimental Chemistry Course edited by the Chemical Society of Japan (5th edition)", Vol. 17 (2005) (Maruzen Co., Ltd.).

Compound (II-1) of the present invention can be produced from compound (6) and compound (7) by a reductive amination reaction in the same manner as in the method (disclosed in Second process for drug-linker conjugate) for producing compound (II-Lb) of the present invention from compound (II-1) and compound (Lb).

Note that, in the above step, $R^{43}$ of H—$R^{43}$ of compound (7) may have a protecting group. In this case, compound (II-1) of the present invention can be produced by removing the protecting group in the final step. The deprotection can be carried out in the conditions commonly employed.

(Third Process for Drug)

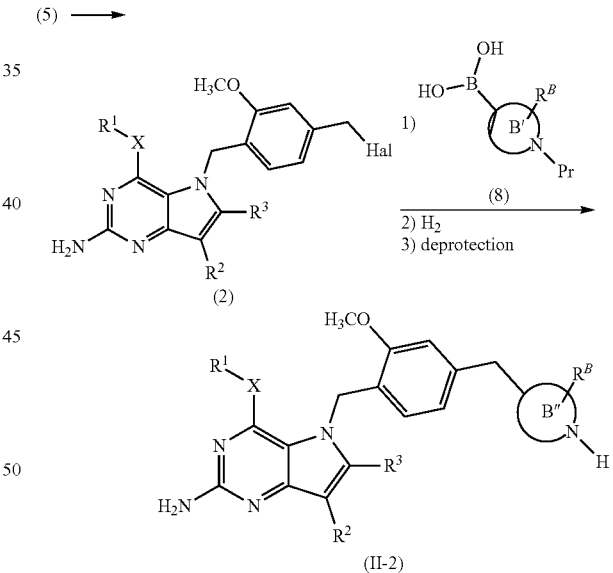

wherein ring B' is a 4- to 6-membered cyclic amine comprising a plurality of C, single N and single G wherein G is C and having a single unsaturated bond. Ring B" is a saturated ring obtained by reducing a single unsaturated bond of ring B' wherein G is CH. The same applies to the following.

Compound (II-2) of the present invention can be obtained by subjecting compound (2) obtained from compound (5) and compound (8) to the Suzuki-Miyaura coupling reaction to obtain a compound and then subjecting the compound obtained to the following hydrogenation reaction and a deprotection reaction.

Compound (2) can be obtained from compound (5) by halogenation. The halogenation reaction can be carried out in the conditions commonly employed for halogenation, more specifically, by adding a halogenating agent in a solution (solvent) such as dichloromethane under ice-cooling and stirring the mixture at room temperature for 1 to 4 hours. Aa the halogenating agent, e.g., thionyl chloride is used.

In the Suzuki-Miyaura coupling reaction of compound (2) and compound (8), a boronic acid $(B(OH)_2)$ group of compound (8) may be a boronate ester group, a boronic acid pinacol ester group, a triol borate base or trifluoroborate base. In the reaction, compound (2) and compound (8) are used in equal amounts or either one of them is used excessively. A mixture of these is stirred in an inert solvent in the presence of a base and a palladium catalyst at room temperature to heat reflux, preferably, 20° C. to 140° C. usually for 0.1 hour to 5 days. Examples of the solvent include halogenated hydrocarbons such as dichloromethane, 1,2-dichloroethane and chloroform; aromatic hydrocarbons such as benzene, toluene and xylene; ethers such as diethyl ether, THF, 1,4-dioxane and dimethoxyethane; alcohols such as MeOH, EtOH, isopropyl alcohol, butanol and amyl alcohol, DMF, DMSO, MeCN, 1,3-dimethylimidazolidin-2-one, water and a mixture of these. Examples of the base include inorganic bases such as tri-potassium phosphate, sodium carbonate, potassium carbonate, sodium hydroxide and barium hydroxide. Examples of the palladium catalyst include tetrakis (triphenylphosphine)palladium, bis(triphenylphosphine)palladium (II) dichloride, [1,1'-bis(diphenylphosphino)ferrocene]palladium (II) dichloride dichloromethane adduct, (1E,4E)-1,5-diphenyl penta-1,4-dien-3-one/palladium (3:2), (2-dicyclohexylphosphino-2',6'-diisopropoxy-1,1'-biphenyl)[2-(2'-amino-1,1'-biphenyl)] palladium(II) methanesulfonate and palladium(II) acetate. It is sometimes beneficial that a reaction is carried out in the presence of a ligand such as dicyclohexyl(2',6'-dimethoxybiphenyl-2-yl)phosphine, dicyclohexyl(2',6'-diisopropoxy-[1,1'-biphenyl]-2-yl)phosphine and 1,1'-bis (diphenylphosphino)ferrocene in order to the reaction to smoothly proceed. It is also sometimes beneficial that the mixture is heated by microwave irradiation in order to the reaction to smoothly proceed.

[Document] J. Am. Chem. Soc., 2005, 127, p. 4685-4696; Org. Lett. 2011, 13, p. 3948-3951; and Org. Lett. 2012, 14, p. 1278-1281.

The hydrogenation reaction of a compound obtained in step 1) of compound (2) is carried out by stirring the compound in an inert solvent in a hydrogen (gas) atmosphere in the presence of a metal catalyst usually for one hour to 5 days. This reaction is usually carried out under cooling to heating, preferably at room temperature. Examples of the solvent include, but are not particularly limited to, alcohols such as methanol, ethanol and 2-propanol; ethers such as diethyl ether, THF, 1,4-dioxane and dimethoxyethane; water, EtOAc, DMF, DMSO and a mixture of these. Examples of the metal catalyst that is suitably used include palladium catalysts such as palladium carbon, palladium black and palladium hydroxide; platinum catalysts such as a platinum plate and platinum oxide; nickel catalysts such as reduced nickel and Raney nickel; rhodium catalysts such tetrakis triphenylphosphine chlororhodium; and iron catalysts such as reduced iron. In place of the hydrogen gas, formic acid or ammonium formate can be used as a hydrogen source in an equal or excessive amount to the compound.

[Document] "Reductions in Organic Chemistry written by M. Hudlicky, 2nd ed. (ACS Monograph: 188)", ACS, 1996. "Experimental Chemistry Course edited by the Chemical Society of Japan (5th edition)", Vol. 19 (2005) (Maruzen Co., Ltd.)

Compound (II-2) of the present invention can be produced by removing a protecting group, Pr. The protecting group Pr for amine can be removed in the conditions usually employed for deprotection.

(Synthesis 1 for Starting Material)

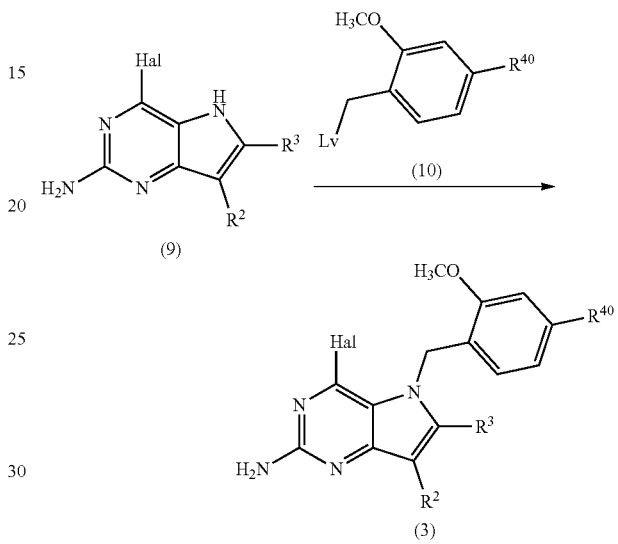

wherein Lv represents a leaving group.

Compound (3) can be produced from compound (9) and compound (10). Examples of the leaving group include a halogen atom, a methanesulfonyloxy group and a p-toluenesulfonyloxy group. The same condition as used in the alkylation reaction for producing compound (II-Lc-Pr) from compound (2) set forth in (Third process for drug-linker conjugate) and compound (Lc-Pr), can be used.

(Synthesis 2 for Starting Material)

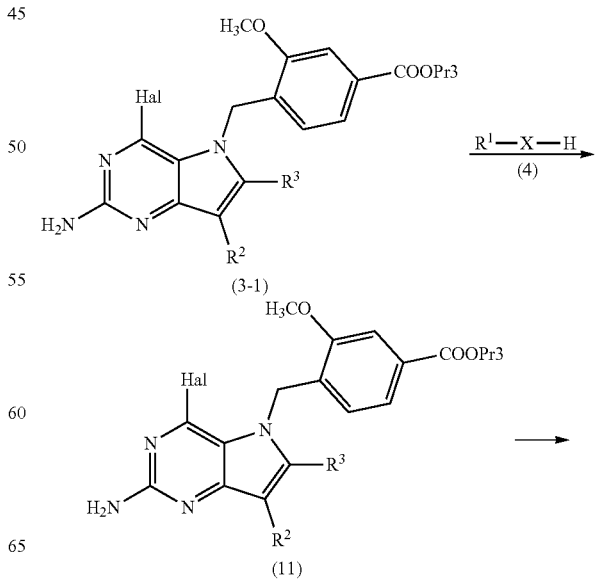

-continued

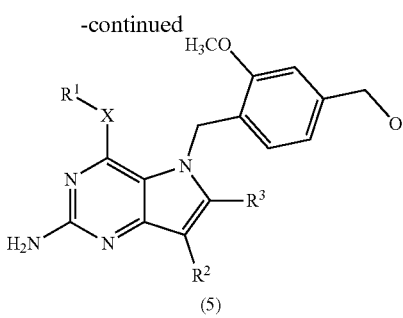

(5)

wherein Pr3 represents a protecting group.

Compound (5) can be produced by a reduction reaction of compound (11), which is produced from compound (3-1) and compound (4).

Compound (3-1) can be produced in the same manner as in Synthesis 1 for starting material. In this case, a compound (10) where $R^{41}$ is COOPr3 is used. For the substitution reaction of compound (11) of the present invention from compound (3-1) and compound (4), the same condition as that (set forth in "First process for drug") in producing compound (II) from compound (3) and compound (4), can be used. For the reduction reaction of compound (11) to compound (5), usually the reaction condition for reducing an ester to an alcohol can be used. Compound (11) is treated with an equal or excessive amount of a reducing agent in an inert solvent under cooling to heating, preferably at −20° C. to 80° C. usually for 0.1 hour to 3 days. Examples of the solvent that is used herein include, but are not particularly limited to, ethers such as diethyl ether, THF, 1,4-dioxane and dimethoxyethane; alcohols such as methanol, ethanol and 2-propanol; aromatic hydrocarbons such as benzene, toluene and xylene; DMF, DMSO, EtOAc and a mixture of these. Examples of the reducing agent that is suitably used include hydride reducing agents such as LAH, sodium borohydride and diisobutylaluminum hydride; metal reducing agents such as sodium, zinc, and iron; and reducing agents disclosed in the following documents.

[Documents], "Oxidation and Reduction in Organic Synthesis (Oxford Chemistry Primers 6)" written by T. J. Donohoe, Oxford Science Publications, 2000. "Experimental Chemistry Course edited by the Chemical Society of Japan (5th edition)", Vol. 14 (2005) (Maruzen Co., Ltd.).

(Synthesis 3 for Starting Material)

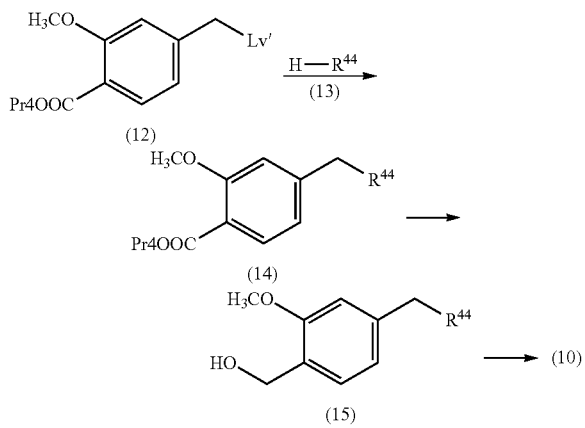

wherein Pr4 represents a protecting group; Lv' represents a leaving group; $R^{44}$ is a group obtained by removing —$CH_2$— from the group represented by formula (a1), formula (b1) or formula (c1) in $R^{40}$; and G is N.

Compound (10) can be produced by reducing compound (14), which is produced from compound (12) and compound (13) and replacing the hydroxy group with a leaving group. Examples of the leaving group herein include a halogen atom, a methanesulfonyloxy group and a p-toluenesulfonyloxy group.

Compound (14) can be produced in the same manner as in Synthesis 1 for starting material. Compound (15) can be produced in the same manner as in the production from compound (11) to compound (5) in Synthesis 1 for starting material.

An antibody-drug conjugate of formula (I) or a salt thereof and a compound of formula (II) or a salt thereof are isolated as a free compound, a salt thereof, a hydrate, a solvate, or a crystal polymorphic substance and purified. An antibody-drug conjugate of formula (I) or a salt thereof and a compound of formula (II) or a salt thereof can be produced by a salt formation reaction routinely carried out. Isolation/purification is carried out by an operation commonly used, such as extraction, fractional crystallization and fractional chromatographic methods (e.g., silica gel chromatography, gel filtration, affinity chromatography).

Various isomers can be each produced by selecting an appropriate starting compound or isolated by using the difference in physicochemical properties between isomers. For example, an optical isomer is obtained by a general optical resolution of a racemate (for example, fractional crystallization producing a diastereomeric salt with an optically active base or acid, chromatography using a chiral column), or can be produced from an appropriate optically active starting compound.

The pharmacological activities of an antibody-drug conjugate of formula (I) or a salt thereof, a compound of formula (II) or a salt thereof, and anti-CLDN6 antibody for use in an antibody-drug conjugate of formula (I) were checked by the following tests.

(Brevity Codes)

Ex: Example (ExL1A1, ExL1A2, ExL5A1, and ExL7A1 represent antibody-drug conjugates of Examples. Note that ExL1-Isotype, ExL5-Isotype, and ExL7-Isotype, which are ended with "-Isotype", are antibody-drug conjugates according to Comparative Examples); AbM: antibody comprising a heavy chain, aCLDN6-VH—$CH_1$—$CH_2$—$CH_3$ and a light chain, aCLDN6-VL-CL, disclosed in International Publication No. WO2022/058298; Ab1: antibody comprising a heavy chain consisting of the amino acid sequence of SEQ ID NO: 2 and a light chain consisting of the amino acid sequence of SEQ ID NO: 4; Ab2: antibody comprising a heavy chain consisting of the amino acid sequence of SEQ ID NO: 6 and a light chain consisting of the amino acid sequence of SEQ ID NO: 8.

Experimental Example 1: TLR7/8 Reporter Assay (1. Acquisition of Cell Line)

HEK293 cells (ATCC, #CRL-1573) were co-transfected with an expression vector having a nucleotide sequence encoding a TLR (human TLR7, human TLR8 or mouse TLR7) protein and a Nanoluc PEST luciferase reporter vector having an NFκB response element sequence (Genbank: JQ513377 bases 33 to 84) integrated therein. Thereafter, the transfected cells were cultured in DMEM (Sigma-Aldrich, #D5796-500 mL) containing Geneticin (Gibco,

10131-027) at a final concentration of 800 μg/mL, Hygromycin B (Invitrogen, #10687010) at a final concentration of 500 μg/mL, penicillin streptomycin (Gibco, #15070-063) at a final concentration of 1% and a 10% fetal bovine serum (FBS) (HyClone, #SH30084.03) to obtain a stable cell line for expression.

(2. In-Vitro Screening of Low Molecule)

To reporter cells obtained above, DMEM containing 10% FBS was added to prepare a suspension of 1×10⁵ cells/mL. The suspension was added to the wells of a 384-well white plate coated with collagen I (hereinafter referred to as "384-well plate", Corning, #356703) at a rate of 20 μL per well. The cells were cultured in the conditions of 37° C. and 5% $CO_2$, overnight (18 hours) and allowed to adhere to the plate. A test sample was dissolved in DMSO. The solution was diluted by adding DMEM medium containing 10% FBS to the solution such that the concentration becomes 5-fold as high as a final concentration. The diluted DMEM medium was added to the wells of the 384-well plate at a ratio of 5 μL/well. After the medium was further incubated in the conditions of 37° C. and 5% $CO_2$ for 24 hours, the plate was taken out and allowed to stand still at room temperature for 10 minutes. Thereafter, chemiluminescence was measured using Nano-Glo Luciferase Assay System (Promega, #N1120) and EnVision 2104 (PerkinElmer) plate reader. A dose-response curve was prepared for each test sample and the $EC_{50}$ value was obtained as a concentration at 50% of the maximum signal. The $EC_{50}$ values of individual compounds are listed in the following table. In the table, hTLR7 represents human TLR7 and hTLR8 represents human TLR8; and mTLR7 represents mouse TLR7. A data item attached with an asterisk (*) indicates the result of 7 hour-incubation and other data items are the results of 24-hour incubation.

TABLE 2

| NUM | hTLR7 $EC_{50}$ (nM) | mTLR7 $EC_{50}$ (nM) | hTLR8 $EC_{50}$ (μM) |
| --- | --- | --- | --- |
| Ex1 | 1.12 | 2.92 | 0.22 |
| Ex2 | 1.77 | 5.36 | 1.97 |
| Ex3 | 3.47 | 6.17 | 2.16 |
| Ex4 | 54.2 | 39.9 | 2.48 |
| Ex5 | 45 | 26.7 | 11.7 |
| Ex6 | 3.22 | 10.1 | 0.964 |
| Ex7 | 8.1 | 21.5 | 2 |
| Ex8 | 11.3 | 23.5 | 2.11 |
| Ex9 | 2.78 | 4.81 | 1.18 |
| Ex10 | 2.74 | 8.75 | 0.716 |
| Ex11 | 17.8 | 9.2 | 13.3 |
| Ex12 | 1.87 | 3.58 | 0.685* |
| Ex13 | 23.3 | 17.4 | 6.22 |
| Ex14 | 28.8 | 27.3 | 6.594 |
| Ex15 | 138 | 111 | 4.88 |
| Ex17 | 2.52 | 7.11 | 3.74 |
| Ex18 | 6.57 | 13.9 | 3.63 |

As the result of the above test, it was confirmed that the compounds of formula (II) or salts thereof have a TLR7/8 dual agonist action.

Experimental Example 2: Evaluation of Binding Activity to Human CLDN6 by Flow Cytometry The cells of human gastric cancer cell line NUGC-3 (JCRB cell bank) expressing CLDN6 were suspended with PBS (Wako, #045-29795) containing 5% FBS so as to have a concentration of 1×10⁶ cells/mL. The suspension was seeded (added) in the wells of a 96-well V-bottom microplate at a rate of 100 μL/well. After centrifugation, the supernatant was removed. AbM: antibody comprising a heavy chain, aCLDN6-VH—$CH_1$—$CH_2$—$CH_3$ and a light chain, aCLDN6-VL-CL, disclosed in International Publication No. WO2022/058298. Ab0, Ab1 and Ab2 were suspended with 5% FBS-containing PBS such that the concentrations fall in the range of 1 ng/mL to 25 μg/mL (12 dilution series were prepared by serial dilution at a 2.5-fold dilution rate from 25 μg/mL to 1 ng/mL). The suspensions were added at a rate of 100 μL/well and allowed to stand still at 4° C. for one hour. PE-F(ab')₂ Goat anti-human IgG (JACKSON, #109-006-098 were diluted 100-fold with 5% FBS-containing PBS. The diluted solution was used to dilute Zombie NIR Fixable Viability Kit (Biolegend, #423106) 200-fold to prepare a secondary-antibody solution. Washing was carried out twice with 5% FBS-containing PBS and the secondary-antibody solution prepared was added at a rate of 100 μL/well and allowed to stand still at 4° C. for one hour. After washing was carried out twice with 5% FBS-containing PBS, resuspension was carried out with 5% FBS-containing PBS. Detection was carried out by CytoFlex S (Beckman Coulter, Inc.). Data analysis was made by Flowjo (company: Treestar). A histogram of PE (phycoerythrin) fluorescence intensity of viable cell fractions was prepared and geometric mean fluorescence intensity (gMFI) was calculated. gMFI values were plotted to make a graph by GraphPad Prism (company: GraphPad Software). As a result of the above test, it was confirmed that Ab0, Ab1 and Ab2 bind to human CLDN6. FIG. 1 shows the binding activities of Ab0, Ab1 and Ab2 to human CLDN6.

Experimental Example 3: Evaluation of TNF-α and INF-γ Productions (1. Preparation of Effector Cells)

Human peripheral blood mononuclear cells (PBMCs), which were collected from blood of a healthy person by Ficoll-Paque PLUS (company: GE Healthcare Bioscience) in accordance with a method commonly used, were suspended in 10% FBS-containing RPMI1640 Medium (Thermo Fisher Scientific, #11875-093). After viable cell count was obtained by the trypan blue dye exclusion test, a suspension was prepared so as to contain 1×10⁷ cells/mL. The cells were used as effector cells.

(2. Collection of Culture Supernatant)

NUGC-3 cells were suspended with 10% FBS-containing RPMI1640 Medium such that the suspension contains the cells at a density of 7.5×10⁶ cells/mL. The suspension was seeded (added) in the wells of a 96-well microplate at a ratio of 25 μL/well. PBMCs prepared in step 1 in the above, were seeded at a ratio of 50 μL/well. ExL1A1 and ExL1A2 were suspended in 10% FBS-containing RPMI1640 Medium so as to have a final concentration within the range of 5.5 μM to 0.97 μM (12 dilution series were prepared by serial dilution at a 3-fold dilution rate from 0.97 μM to 5.5 μM), each were added at a rate of 25 μL/well. The cells were cultured in the conditions of 37° C. and 5% $CO_2$ for 24 hours. The supernatant was collected.

(3. Measurement of TNF-α and INF-γ Productions)

Using the supernatant collected in step 2 in the above, TNF-α and INF-γ productions were measured by TNFα (human) AlphaLISA Detection Kit (Perkin Elmer, #AL208C) and IFN-γ (human) AlphaLISA Detection Kit (Perkin Elmer, #AL217F) in accordance with a method commonly used. Measurement was carried out by use of EnVision 2104 plate reader. A graph was drawn by GraphPad Prism (company: GraphPad Software).

Figure 2:
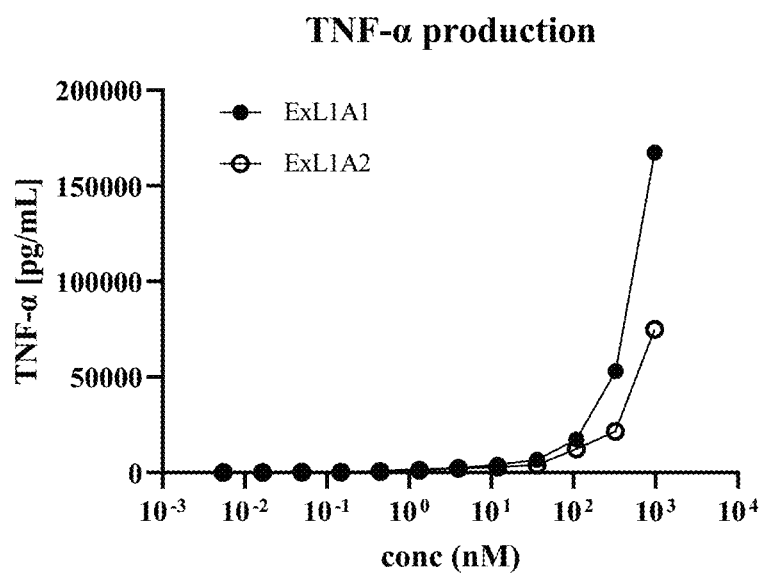
FIG. 2 shows the measurement results on the amounts of cytokines produced respectively by antibody-drug conjugates ExL1A1 and ExL1A2. The vertical axis depicts the production (pg/mL) of TNF-α or INF-γ cytokine and the horizontal axis depicts antibody concentration (nM).
Figure 2:
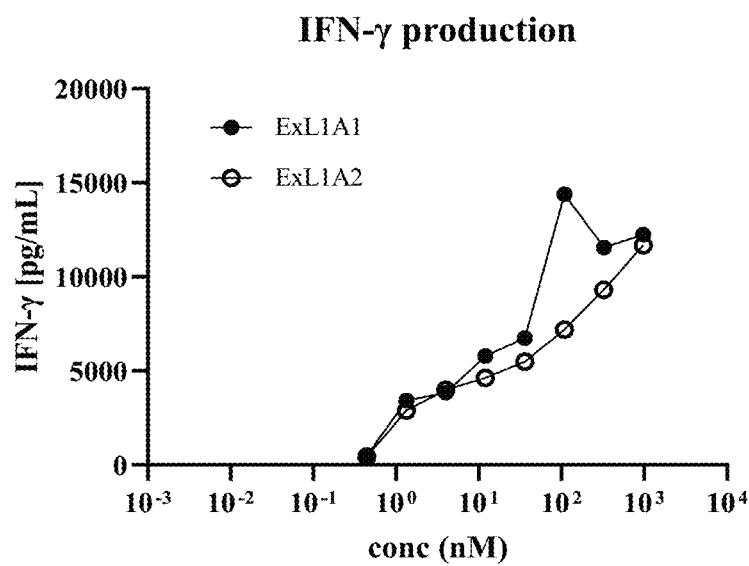

FIG. 2 shows the measurement results of cytokine amounts produced by ExL1A1 and ExL1A2.

As a result of the above test, it was confirmed that antibody-drug conjugates (I) or salts thereof listed in the above table produce cytokines.

Experimental Example 4: Evaluation of In-Vivo Activity in Xenograft Model

NUGC-3 cells ($5\times10^6$ cells) were suspended with 100 µL of Corning matrigel basal membrane matrix phenol red free (Corning, #356237) and subcutaneously transplanted into SCID mice (CB17/Icr-Prkdcscid/CrlCrlj, purchased from Charles River Laboratories Japan, Inc.) at the lateral region at a ratio of 100 µL/head. Day 7 and Day 14 after transplantation, PBS or a test antibody or a test antibody-drug conjugate (3 mg/kg) was administered through the tail vein of the tumor-bearing mice (n=6 or 9). As test antibodies, Ab0 and Ab1 were used. As test antibody-drug conjugates, ExL1A1, ExL5A1, ExL7A1, ExL1-Isotype, ExL5-Isotype and ExL7-Isotype were used. ExL1-Isotype is an antibody using an anti-KLH antibody (International Publication No. WO2013/094723) in place of Ab1 of ExL1A1. ExL5-Isotype and ExL7-Isotype were prepared in the same manner as in ExL1-Isotype. The major axis and minor axis of a transplanted tumor were measured by an electronic digital caliper (made by Mitutoyo Corporation) twice per week. A tumor volume was calculated in accordance with the following formula:

Tumor volume $(mm^3) = 1/2 \times$ minor diameter (mm) $\times$ minor diameter (mm) $\times$ major diameter (mm)

Figure 3:
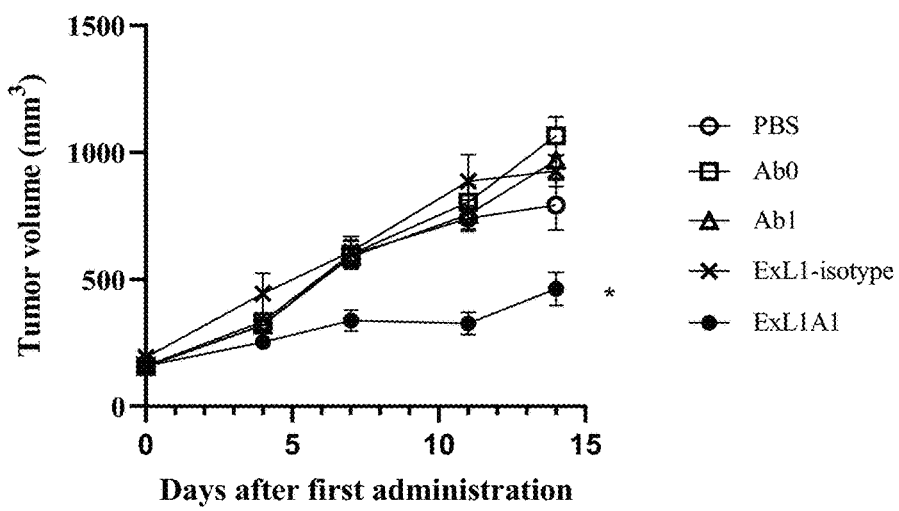
FIG. 3 shows evaluation results on in-vivo activities of antibody-drug conjugates ExL1A1, ExL5A1 and ExL7A1 in xenograft models. The vertical axis depicts tumor volume (mm$^3$) and the horizontal axis depicts the number of days after the first administration of an antibody. A significance probability P value was obtained by comparing the tumor volume of a PBS administration group and the tumor volume of ExL1A1, ExL5A1, and ExL7A1 administration groups after 14 days in accordance with the unpaired t-test (*: P<0.05, **: P<0.01).
Figure 3:
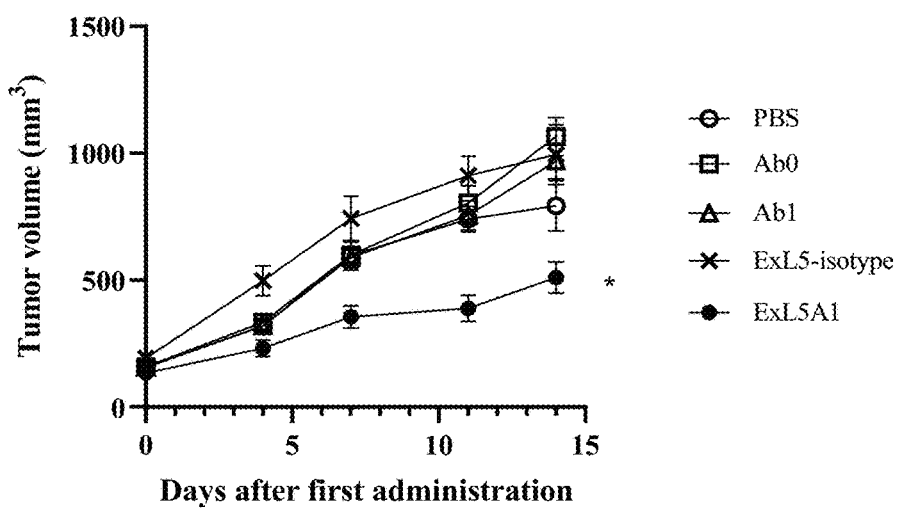
Figure 3:
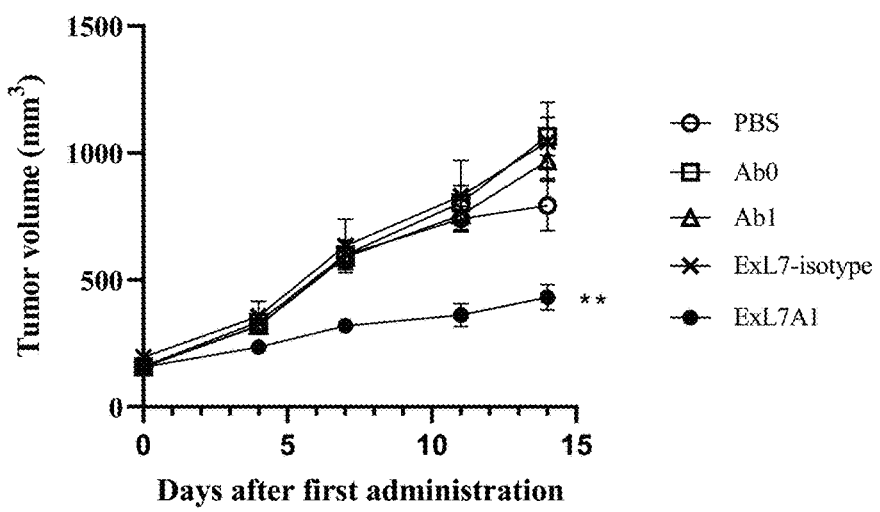

As a result of the above test, it was confirmed that none of the antitumor effects of Ab0, Ab1 and ExL1-Isotype, ExL5-Isotype and ExL7-Isotype have an antitumor effect, but that ExL1A1, ExL5A1 and ExL7A1 have a significant antitumor effect (FIG. 3). From the results, it was demonstrated that some of anti-CLDN6 antibody-drug conjugates containing a TLR7/8 dual agonist compound have been confirmed to have antitumor effects on cancer expressing CLDN6. The antibody-drug conjugates of the present invention containing a TLR7/8 dual agonist compound can be expected for use in prevention or treatment of the cancer expressing CLDN6. Furthermore, an anti-TAA antibody-drug conjugate containing a TLR7/8 dual agonist compound can be expected for use in prevention or treatment of cancer expressing the TAA.

Experimental Example 5: Evaluation of INF-γ Productions when TLR8 and TLR7/8 Dual Inhibitors were Added The human ovarian cancer cell line OVCAR-3 (ATCC, #HTB-161) expressing CLDN6 and having GFP introduced therein was suspended with 10% FBS-containing RPMI1640 Medium so as to have a concentration of $2\times10^6$ cells/mL and seeded (added) in the wells of a 96-well microplate at a rate of 25 µL/well. PBMCs prepared so as to have a concentration of $1.25\times10^7$ cells/mL in accordance with Experimental Example 3 (1. Preparation of effector cells) were seeded at a rate of 40 µL/well. TLR8 inhibitor CU-CPT9a (InvivoGen, #inh-cc9a) or TLR7/8 dual inhibitor Enpatoran (MedChemExpress, #HY-134581) prepared with 10% FBS-containing RPMI1640 Medium to have a final concentration of 10 µM, or 10% FBS-containing RPMI1640 Medium was added at a rate of 10 µL/well. Culture was carried out in the conditions of 37° C. and 5% $CO_2$ for 3 hours. Thereafter, ExL1A1 was suspended with 10% FBS-containing RPMI1640 Medium so as to have a final concentration of 23 µM to 1.8 µM (8 dilution series were prepared by serial dilution at 5-fold dilution rate from 1.8 µM to 23 µM) and added at a rate of 25 µL/well. Culture was carried out in the conditions of 37° C. and 5% $CO_2$ for 70 hours. The supernatant was collected. Using the supernatant collected, INF-γ production was measured in the same manner as in Experimental Example 3 (3. Measurement of TNF-α and INF-γ productions). A graph was formed by GraphPad Prism (company: GraphPad Software).

Figure 4:
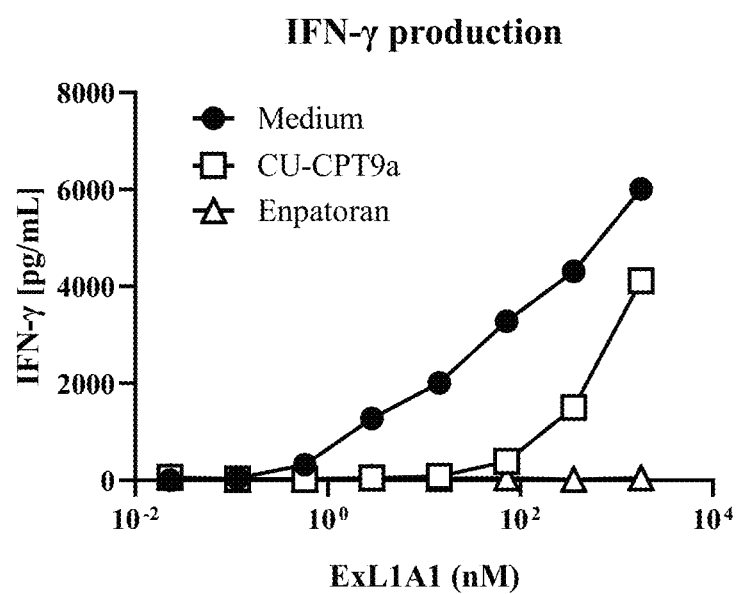
FIG. 4 shows the measurement results of cytokine productions by an antibody-drug conjugate ExL1A1 in a culture medium, the medium containing a TLR8 inhibitor U-CPT9a and the medium containing a TLR7/8 inhibitor Enpatoran. The vertical axis depicts the production (pg/mL) of INF-γ cytokine and the horizontal axis depicts the concentration of the antibody (nM).

FIG. 4 shows the measurement results of INF-γ productions by ExL1A1 in a culture medium, a medium containing CU-CPT9a, and a medium containing Enpatoran.

As the results of the above test, it was found that the addition of a TLR8 inhibitor to the antibody-drug conjugate of the present invention partly suppressed cytokine production, and the addition of a TLR7/8 dual inhibitor completely suppressed cytokine production. From this, it was confirmed that TLR8 agonistic action in addition to the TLR7 agonistic action in the drug-antibody conjugate of the present invention contributes to an increase of cytokine production.

A pharmaceutical composition containing one or two or more antibody-drug conjugates of formula (I) or salts thereof as an active ingredient can be prepared by using an excipient commonly used in the technical field, i.e., a pharmaceutical excipient or pharmaceutical carrier in accordance with a method commonly used.

Dosage form may be any one of non-oral dosage forms such as injections including an intra-articular injection, an intravenous injection and an intramuscular injection, an infusion agent, a suppository, an eye drop, an eye ointment, a transdermal liquid, an ointment, a transdermal patch, a transmucosal liquid, a transmucosal patch and an inhaler. The injection and infusion agent can be administered by an appropriate method such as intravenous administration, subcutaneous administration, intraperitoneal administration and intratumoral administration.

An injection for parenteral administration contains an aseptic aqueous or non-aqueous solution agent, a suspending agent or an emulsifier. Examples of the aqueous solvent include distilled water for injection and physiological saline. Examples of the non-aqueous solvent include an alcohol such as ethanol. Such a composition may further contain a tonicity agent, a preservative, a wetting agent, an emulsifier, a dispersant, a stabilizer or a solubilizer. These agents are sterilized, for example, by filtration through a bacteria-trapping filter, blending a disinfectant or irradiation. As these injections, solid compositions are aseptically prepared (in advance) and dissolved or suspended in aseptic water or an aseptic solvent for injection (just) before use and put in use.

Examples of the external agent include an ointment, a plaster, a cream agent, a jelly, a poultice, a spray agent, a lotion, an eye drop and an eye ointment. The external agent contains an ointment base, a lotion base, an aqueous or non-aqueous liquid, a suspending agent and an emulsifying agent generally used are contained.

As a transmucosal agent such as an inhaler and a nasal agent, a solid, a liquid or a semi-solid agent is used and can be produced in accordance with a method commonly known in the technical field. For example, an excipient known in the technical field, further, a pH adjuster, a preservative, a surfactant, a lubricant, a stabilizer and a thickener may be appropriately added. Administration can be made by an appropriate device for inhalation or blowing. For example, a device or sprayer commonly known, such as a metered dose inhalation device may be used. A compound can be administered alone or in the form of a powder composition, or a solution or suspension of a compound in combination with a pharmaceutically acceptable carrier. A dry powder inhaler may be a device for single or multiple dosing. Dry powder or a capsule containing powder can be used. Alternatively, a pressurized aerosol spray using an appropriate ejection agent, for example, an appropriate gas such as chlorofluoroalkane or carbon dioxide may be used.

Usually, the dose per day is properly about 0.001 to 100 mg/kg per body-weight, preferably 0.1 to 30 mg/kg, and further preferably 0.1 to 10 mg/kg. The dose is administered once or in divided 2 to 4 portions. In the case of intravenous administration, the dose per day is properly about 0.0001 to 10 mg/kg per body-weight and administered once or in divided portions. In the case of a transmucosal agent, the dose per body-weight is about 0.001 to 100 mg/kg and administered once per day or in divided portions. The dose is appropriately determined in consideration of individual factors such as the symptom, age and sex.

The pharmaceutical composition of the present invention according to an embodiment contains one or more types of antibody-drug conjugate of formula (I) or a salt thereof serving as an active ingredient in a ratio of 0.01 to 100 wt % or 0.01 to 50 wt % but the content of the active ingredient varies depending on the administration route, dosage form, administration site, the types of excipient and additives.

The antibody-drug conjugate of formula (I) can be used in combination with various therapeutic agents or prophylactic agents for a disease on which the antibody-drug conjugate of formula (I) is presumed to be effective. The concomitant drug may be administered simultaneously with the antibody-drug conjugate, separately but continuously, or at desired time intervals. The concomitant drug may be blended with the antibody-drug conjugate or provided as a separate preparation. The concomitant drug is, for example, a therapeutic agent for use in treating a target disease.

EXAMPLES

Now, a process for an antibody-drug conjugate of formula (I) will be further detailed based on Examples. Note that, the present invention is not limited by the compounds set forth below. Processes for starting compounds will be set forth in Production Examples and processes for compounds commonly known are disclosed in Reference Examples. A process for an antibody-drug conjugate of formula (I) is not limited to those detailed in Examples. The antibody-drug conjugate of formula (I) can be produced by a combination of the processes detailed in Examples or methods known to those skilled in the art.

The following brevity codes may be used in the specification, Examples, Production Examples and Tables.

Anti-CLDN6 antibody: anti-claudin 6 antibody, TLR7/8 dual agonist: Toll-like receptor 7/Toll-like receptor 8 dual agonist, DAST: N,N-diethylaminosulfur trifluoride, DEAD: diethyl azodicarboxylate, DCM: dichloromethane, DIAD: diisopropyl azodicarboxylate, DIPEA: N,N-Diisopropylethylamine, DMF: dimethylformamide, DMP: Dess-Martin Periodinane, DMSO: dimethyl sulfoxide, D-PBS: Dulbecco's phosphate buffered saline, EtOAc: ethyl acetate, FA: formic acid, HATU: 2-(7-aza-1H-benzotriazol-1-yl)-1,1,3,3-tetramethyluronium hexafluorophosphate, LAH: lithium aluminum hydride, MeCN: acetonitrile, MsCl: methanesulfonyl chloride, NAC: N-acetyl-L-cysteine, NMP: N-methyl-2-pyrrolidone, PE: petroleum ether, PBS6.2/EDTA: phosphate buffer containing ethylenediaminetetraacetic acid (EDTA, 5 mM) (adjusted to pH 6.2 with 10 mM and 1 M hydrochloric acid), $PdCl_2$ $(dppf)\_CH_2Cl_2$: dichloromethane complex of [1,1'-bis(diphenylphosphino)ferrocene] dichloropalladium (II), Palau'Chlor: 2-chloro-1,3-bis(methoxycarbonyl)guanidine, prep-HPLC: preparative High Performance Liquid Chromatography, SEC: size exclusion chromatography, TBAI: tetrabutylammonium iodide, TEA: triethylamine, TCEP: tris(2-carboxyethyl)phosphine hydrochloride, TFA: trifluoro acetate, THF: tetrahydrofuran, MWCO: molecular weight cut-off (for example, 10000 MWCO means that a substance having a molecular weight of 10000 or less can be removed by a filter), nPn: n-pentyl, Me: methyl, Et: ethyl, tBu: tert-butyl, DAR: the compound-to-antibody ratio in an antibody-drug conjugate (more specifically, an average number of compounds bound to a single antibody), NUM: Example No. or Production Example No. (/HCl means that the substance listed in this Example or Production Example is hydrochloride; /TFA means that the substance listed in this Example or Production Example is trifluoro acetate), PEx: Production Example No., Ex: Example No., REF: production method (the specified substance was produced in the same process as in the substance specified by Example No. or Production Example No. in the column. For example, Ex1 in the column "REF" of PEx2-2 means that PEx2-2 of Production Examples was produced in the same manner as in the process set forth in Example Ex1. A plurality of numbers listed in the column "REF" means that production was made by performing the steps (represented by the numbers) sequentially in the order listed therein. For example, PEx4-1 and Ex2 listed in Ex11 mean that production was made with reference to the specified steps sequentially in the order listed), STR: chemical structure, DAT: physicochemical data, ESI+: m/z value in ESI-MS+(the case where data are not particularly listed means [M+H]+), a typical signal is listed as the NMR signal, s: single line, d: double line, t: triple line, q: quadruple line, m: multiple line, br: broad (line), $[\alpha]_D^{20}$: specific rotation at 20° C., and c: concentration (g/100 mL) when specific rotation was measured and the solvent used in measurement is listed together. Note that, in the specification, some of the compounds are designated by using naming software such as ACD/Name (registered trademark, Advanced Chemistry Development, Inc.). For convenience's sake, concentrations are indicated by M in place of mol/L. For example, a 1 M sodium hydroxide solution means that a 1 mol/L sodium hydroxide solution.

PRODUCTION EXAMPLES AND EXAMPLES (Production of Antibody)

Examples AB-1: Construction of Expression Vector for Humanized Anti-CLDN6 Antibody For a humanized anti-CLDN6 antibody, a sequence for humanizing a mouse anti-CLDN6 antibody was designed based on the sequences of a heavy chain variable region and light chain variable region of each of mouse anti-CLDN6 antibodies GT512muMAB 64A and GT512muMAB 61D disclosed in International Publication No. WO 2011/057788, in accordance with the method disclosed in the document (Front Biosci., 2008, Vol. 13, p. 1619-1633). A model structure was constructed and analyzed by Integrated Computational Chemistry System, MOE (provided by MOLSIS Inc.) and a back mutation was introduced within the framework region. The two types of humanized anti-CLDN6 antibodies are designated as Ab1 and Ab2, respectively. Ab1 is an antibody comprising a heavy chain consisting of the amino acid sequence of SEQ ID NO: 2 and a light chain consisting of the amino acid sequence of SEQ ID NO: 4. Ab2 is an antibody comprising a heavy chain consisting of the amino acid sequence of SEQ ID NO: 6 and a heavy chain consisting of the amino acid sequence of SEQ ID NO: 8. Polynucleotides encoding the amino acid sequences of Ab1 and Ab2 designed were integrated into pcDNA3.4 TOPO vector (Thermo Fisher Scientific). The vectors prepared are called an Ab1 expression vector and an Ab2 expression vector, respectively.

Example AB: Preparation of Humanized Anti-CLDN6 Antibody

Each of the Ab1 expression vector and Ab2 expression vector (prepared in Production Examples AB-1) was introduced into ExpiCHO-S cells by use of ExpiFectamine CHO Transfection Kit (Thermo Fisher Scientific, #A29129). The cells were cultured for several days. From the culture supernatants, Ab1 and Ab2 were purified by an affinity purification method using MabSelect SuRe pcc (company: GE Healthcare Bioscience, #27-5438-02).
(Production of Drug)

Production Examples 1-1

To a solution of tert-butyl (3S)-3-(hydroxymethyl)piperazine-1-carboxylate (3 g) in DMF (30 mL), DIPEA (4.72 mL) was added at 20° C. After the reaction solution was stirred at 20° C. for 30 minutes, methyl 4-(bromomethyl)-2-methoxybenzoate (3.59 g) was added to the reaction solution. The reaction solution was stirred at 20° C. for 12 hours, concentrated under reduced pressure. The resultant oily compound was purified by silica gel column chromatography (PE:EtOAc=50/50-0/100) to obtain tert-butyl (3S)-3-(hydroxymethyl)-4-{[3-methoxy-4-(methoxycarbonyl)phenyl]methyl}piperazine-1-carboxylate (5.12 g) as an oily substance.

Production Examples 1-2

To a solution of tert-butyl (3S)-3-(hydroxymethyl)-4-{[3-methoxy-4-(methoxycarbonyl)phenyl]methyl}piperazine-1-carboxylate (4.62 g) in chloroform (40 mL), a solution of DAST (9.94 g) in chloroform (10 mL) was added at 0° C. The reaction solution was stirred at 20° C. for 3 hours. A sodium hydrogen carbonate aqueous solution was added to the reaction solution to adjust pH to 8. The reaction solution was extracted twice with DCM (100 mL). The organic layers were combined and concentrated under reduced pressure. The resultant residue was purified by prep-HPLC (column: Xtimate C18 150×40 mm×10 μm, water (0.225% FA)/MeCN=70/30-40/60) to obtain tert-butyl (3S)-3-(fluoromethyl)-4-{[3-methoxy-4-(methoxycarbonyl)phenyl]methyl}piperazine-1-carboxylate (2.01 g) as an oily substance.

Production Examples 1-3

To a solution of tert-butyl (3S)-3-(fluoromethyl)-4-{[3-methoxy-4-(methoxycarbonyl)phenyl]methyl}piperazine-1-carboxylate (2.01 g) in THF (35 mL), LAH (192.43 mg) was added at 0° C. The reaction solution was stirred at 20° C. for one hour. After sodium sulfate decahydrate (0.3 g) was added to the reaction solution, the reaction solution was concentrated under reduced pressure. The residue obtained was purified by silica gel column chromatography (PE/EtOAc=50/50-20/80) to obtain tert-butyl (3S)-3-(fluoromethyl)-4-{[4-(hydroxymethyl)-3-methoxyphenyl]methyl}piperazine-1-carboxylate (1.71 g) as an oily compound.

Production Examples 1-4

To a solution of tert-butyl (3S)-3-(fluoromethyl)-4-{[4-(hydroxymethyl)-3-methoxyphenyl]methyl}piperazine-1-carboxylate (1.71 g) in DCM (35 mL), DIPEA (1.62 mL) was added at 0° C. After the reaction mixture was stirred at 20° C. for 30 minutes, MsCl (956.97 mg) was added at 0° C. The reaction mixture was stirred at 20° C. for 12 hours and concentrated under reduced pressure to obtain tert-butyl (3S)-4-{[4-(chloromethyl)-3-methoxyphenyl]methyl}-3-(fluoromethyl)piperazine-1-carboxylate (1.8 g) as an oily crude product.

Production Examples 1-5

To a solution of 4-chloro-5H-pyrrolo[3,2-d]pyrimidin-2-amine (0.5 g) in DMF (20 mL), cesium carbonate (2.90 g) was added at 20° C. After the reaction mixture was stirred at the same temperature for 30 minutes, tert-butyl (3S)-4-{[4-(chloromethyl)-3-methoxyphenyl]methyl}-3-(fluoromethyl)piperazine-1-carboxylate (1.03 g) was added thereto. The reaction mixture was stirred at the same temperature for 12 hours and filtered. After water (100 mL) was added to the filtrate, the filtrate was extracted three times with ethyl acetate (150 mL). The organic layers were combined and concentrated under reduced pressure. The residue obtained was purified by silica gel column chromatography (PE:EtOAc=0:100) to obtain tert-butyl (3S)-4-({4-[(2-amino-4-chloro-5H-pyrrolo[3,2-d]pyrimidin-5-yl)methyl]-3-methoxyphenyl}methyl)-3-(fluoromethyl)piperazine-1-carboxylate (1.03 g) as a solid substance.

Production Examples 1-6

To a solution of tert-butyl (3S)-4-({4-[(2-amino-4-chloro-5H-pyrrolo[3,2-d]pyrimidin-5-yl)methyl]-3-methoxyphenyl}methyl)-3-(fluoromethyl)piperazine-1-carboxylate (0.93 g) in DMSO (20 mL), DIPEA (936.34 μL) and pentan-1-amine (312.37 mg) were added at 20° C. The reaction mixture was stirred at 80° C. for 12 hours. After water (50 mL) was added to the reaction mixture, the reaction mixture was extracted three times with ethyl acetate (100 mL). The organic layers were combined and concentrated under reduced pressure. The residue obtained was purified by silica gel column chromatography (DCM/methanol=10/1) to obtain tert-butyl (3S)-4-[(4-{[2-amino-4-(pentylamino)-5H-pyrrolo[3,2-d]pyrimidin-5-yl]methyl}-3-methoxyphenyl)methyl]-3-(fluoromethyl)piperazine-1-carboxylate (0.9 g) as a solid substance.

Example 1

To a solution of tert-butyl (3S)-4-[(4-{[2-amino-4-(pentylamino)-5H-pyrrolo[3,2-d]pyrimidin-5-yl]methyl}-3-methoxyphenyl)methyl]-3-(fluoromethyl)piperazine-1-carboxylate (0.9 g) in DCM (5 mL), HCl/dioxane (4 M, 12 mL) was added at 20° C. The reaction mixture was stirred at the same temperature for one hour. The reaction mixture was concentrated under reduced pressure. The residue obtained was purified by prep-HPLC (column: Xtimate C18 150×40 mm×10 μm, water (0.05% NH$_3$/H$_2$O)/MeCN=90/10-40/60) to obtain 5-[(4-{[(2S)-2-(fluoromethyl)piperazin-1-yl]methyl}-2-methoxyphenyl)methyl]-N$^4$-pentyl-5H-pyrrolo[3,2-d]pyrimidine-2,4-diamine (474 mg) as a solid substance.

Production Examples 2-1

To a solution of tert-butyl (2R)-2-(hydroxymethyl)piperazine-1-carboxylate (1.00 g) in DMF (15 mL), DIPEA (1.61 mL) was added at 20° C. After the reaction mixture was stirred at the same temperature for 30 minutes, methyl 4-(bromomethyl)-2-methoxybenzoate (1.2 g) was added to this. The reaction mixture was stirred at 20° C. for 12 hours and concentrated under reduced pressure. The oily substance obtained was purified by silica gel column chromatography (PE:EtOAc=50/50-0/100) to obtain tert-butyl (2R)-2-(hydroxymethyl)-4-{[3-methoxy-4-(methoxycarbonyl)phenyl]methyl}piperazine-1-carboxylate (1.83 g) as an oily substance.

Production Examples 2-2

To a solution of tert-butyl (2R)-2-(hydroxymethyl)-4-{[3-methoxy-4-(methoxycarbonyl)phenyl]methyl}piperazine-1-carboxylate (1.83 g) in DCM (3 mL), HCl/MeOH (4 M, 30 mL) was added at 0° C. The reaction mixture was stirred at 20° C. for 12 hours and concentrated under reduced pressure. After a sodium hydrogen carbonate aqueous solution (150 mL) was added, the reaction mixture was extracted three times with DCM (150 mL). The organic layers were combined and concentrated under reduced pressure to obtain methyl 4-{[(3R)-3-(hydroxymethyl)piperazin-1-yl]methyl}-2-methoxybenzoate (1.22 g) as an oily substance.

Production Examples 2-3

To a solution of methyl 4-{[(3R)-3-(hydroxymethyl)piperazin-1-yl]methyl}-2-methoxybenzoate (1.22 g) in DCM (20 mL), 2,4-dimethoxybenzaldehyde (688.75 mg) was added at 20° C. After the reaction mixture was stirred at 20° C. for 4 hours, sodium triacetoxyborohydride (1.14 g) was added thereto. The reaction mixture was stirred at 20° C. for 12 hours and a sodium hydrogen carbonate aqueous solution (50 mL) was added thereto. The reaction mixture was extracted twice with DCM (100 mL). The organic layers were combined and concentrated under reduced pressure. The residue obtained was purified by silica gel column chromatography (DCM/methanol=20/1) to obtain methyl 4-{[(3R)-4-[(2,4-dimethoxyphenyl)methyl]-3-(hydroxymethyl)piperazin-1-yl]methyl}-2-methoxybenzoate (1.47 g) as an oily substance.

Production Examples 2-4

Using methyl 4-{[(3R)-4-[(2,4-dimethoxyphenyl)methyl]-3-(hydroxymethyl)piperazin-1-yl]methyl}-2-methoxybenzoate (1.47 g) in the same manner as in Production Examples 1-2 to Production Examples 1-6, 5-[(4-{[(3R)-4-[(2,4-dimethoxyphenyl)methyl]-3-(fluoromethyl)piperazin-1-yl]methyl}-2-methoxyphenyl)methyl]-N$^4$-pentyl-5H-pyrrolo[3,2-d]pyrimidine-2,4-diamine (544.55 mg) was obtained as a solid crude product.

Example 2

To a solution of 5-[(4-{[(3R)-4-[(2,4-dimethoxyphenyl)methyl]-3-(fluoromethyl)piperazin-1-yl]methyl}-2-methoxyphenyl)methyl]-N$^4$-pentyl-5H-pyrrolo[3,2-d]pyrimidine-2,4-diamine (544.55 mg) in DCM (5 mL), TFA (5 mL) was added at 0° C. in a nitrogen atmosphere. The reaction mixture was stirred at 20° C. for one hour and concentrated under reduced pressure. The crude product obtained was purified by prep-HPLC (column: Boston Green ODS 150×30 mm×5 μm, water (TFA)/MeCN=94/6-54/46) to obtain 5-[(4-{[(3R)-3-(fluoromethyl)piperazin-1-yl]methyl}-2-methoxyphenyl)methyl]-N$^4$-pentyl-5H-pyrrolo[3,2-d]pyrimidine-2,4-diamine (trifluoroacetic acid) salt (240 mg) as a solid substance.

Production Examples 3-1

To a solution of {4-[(2-amino-4-chloro-5H-pyrrolo[3,2-d]pyrimidin-5-yl)methyl]-3-methoxyphenyl}methanol (1 g) in DMSO (5 mL), DIPEA (4.2 mL) and pentan-1-amine (1.6 mL) were added. The reaction mixture was stirred at 100° C. for 2 days and allowed to cool to room temperature. Thereafter, water and chloroform were added. The reaction mixture was extracted with chloroform by use of a phase separator. The extract was concentrated under reduced pressure. The residue obtained was purified by silica gel column chromatography (chloroform/methanol/28% ammonia water=100/0/0-90/9/1) to obtain (4-{[2-amino-4-(pentylamino)-5H-pyrrolo[3,2-d]pyrimidin-5-yl]methyl}-3-methoxyphenyl)methanol (807 mg) as a solid substance.

Production Examples 3-2

To a mixture of (4-{[2-amino-4-(pentylamino)-5H-pyrrolo[3,2-d]pyrimidin-5-yl]methyl}-3-methoxyphenyl)methanol (50 mg) and DCM (2 mL), DMP (90 mg) was added under ice-cooling. The reaction mixture was stirred at room temperature for 2 hours. To the reaction mixture, a 10% aqueous sodium sulfite solution, a saturated sodium hydrogen carbonate aqueous solution and a mixed solvent (chloroform/methanol=5/1) were added.

The reaction mixture was extracted with a mixed solvent (chloroform/methanol=5/1) by use of a phase separator. The extract was concentrated under reduced pressure. The residue obtained was purified by silica gel column chromatography (chloroform/methanol=100/0-80/20) to obtain 4-{[2-amino-4-(pentylamino)-5H-pyrrolo[3,2-d]pyrimidin-5-yl]methyl}-3-methoxybenzaldehyde (34 mg) as a solid substance.

Example 3

To a mixture of 4-{[2-amino-4-(pentylamino)-5H-pyrrolo[3,2-d]pyrimidin-5-yl]methyl}-3-methoxybenzaldehyde (31 mg), cyclopropanamine (0.012 mL) and TEA (0.024 mL) in DCM (1.2 mL), sodium triacetoxyborohydride (36 mg) was added. The reaction mixture was stirred at room temperature for 2 hours. To the mixture, cyclopropanamine (0.012 mL) and sodium triacetoxyborohydride (36 mg) were added. The resultant reaction mixture was stirred at room temperature overnight. To the mixture, cyclopropanamine (0.012 mL), sodium triacetoxyborohydride (36 mg) and DCM (1.2 mL) were added. The reaction mixture was stirred at 40° C. for 2 hours and then allowed to cool up to room temperature. Cyclopropanamine (0.012 mL) and sodium triacetoxyborohydride (36 mg) were added to the mixture. The reaction mixture was stirred at 40° C. for 8 hours and allowed to cool to room temperature. To the reaction mixture, a saturated sodium hydrogen carbonate aqueous solution and chloroform were added. The reaction mixture was extracted with chloroform by use of a phase separator. The extract was concentrated under reduced pressure. The residue obtained was purified by silica gel column chromatography (chloroform/methanol/28% ammonia water=100/0/0-90/9/1) to obtain 5-({4-[(cyclopropylamino)methyl]-2-methoxyphenyl}methyl)-$N^4$-pentyl-5H-pyrrolo[3,2-d]pyrimidine-2,4-diamine (23 mg) as a solid substance.

Production Examples 4-1

To a solution of {4-[(-2-amino-4-chloro-5H-pyrrolo[3,2-d]pyrimidin-5-yl)methyl]-3-methoxyphenyl}methanol (200 mg) in DMSO (2 mL), DIPEA (0.162 mL) and pentane-1-thiol (0.094 mL) were added. The reaction mixture was stirred at 80° C. for 2 hours and allowed to cool to room temperature. Thereafter, DIPEA (0.162 mL) and pentane-1-thiol (0.094 mL) were added to the reaction mixture, which was stirred at 100° C. overnight. After the reaction mixture was allowed to cool to room temperature, DIPEA (0.162 mL) and pentane-1-thiol (0.094 mL) were added. The reaction mixture was stirred at 100° C. for 3 days and allowed to cool to room temperature, water and a mixed solvent (chloroform/methanol) were added. The reaction mixture was extracted with a mixed solvent (chloroform/methanol) by use of a phase separator. The extract was concentrated under reduced pressure. The residue obtained was purified by silica gel column chromatography (chloroform/methanol=100/0-90/10) followed by silica gel column chromatography (hexane/ethyl acetate=98/2-0/100) to obtain (4-{[2-amino-4-(pentylsulfanyl)-5H-pyrrolo[3,2-d]pyrimidin-5-yl]methyl}-3-methoxyphenyl)methanol (48 mg) as a solid substance.

Example 4

To a solution of (4-{[2-amino-4-(pentylsulfanyl)-5H-pyrrolo[3,2-d]pyrimidin-5-yl]methyl}-3-methoxyphenyl)methanol (35 mg) in DCM (2 mL), thionyl chloride was added under ice-cooling (0.066 mL). The reaction mixture was stirred at room temperature for one hour and concentrated under reduced pressure. To the residue obtained, NMP (1 mL), DIPEA (0.078 mL), piperazine (40 mg) and potassium iodide (16 mg) were added. The reaction mixture was stirred at 80° C. for one hour and allowed to cool to room temperature, water and a mixed solvent (chloroform/methanol=5/1) were added to this. The mixture was extracted with a mixed solvent (chloroform/methanol=5/1) by use of a phase separator. The extract was concentrated under reduced pressure. The residue obtained was purified by silica gel column chromatography (chloroform/methanol/28% ammonia water=100/0/0-90/9/1) to obtain 5-({2-methoxy-4-[(piperazin-1-yl)methyl]phenyl}methyl)-4-(pentylsulfanyl)-5H-pyrrolo[3,2-d]pyrimidin-2-amine (33.9 mg) as a solid substance.

Production Examples 5-1

To a solution of 4-chloro-5-{[4-(chloromethyl)-2-methoxyphenyl]methyl}-5H-pyrrolo[3,2-d]pyrimidin-2-amine (200 mg) in MeCN (3 mL), DIPEA (0.08 mL) and [(2S)-pyrrolidin-2-yl]methanol (0.035 mL) were added at room temperature. The reaction solution was stirred at the same temperature for 18 hours, added in water (15 mL) and extracted twice with ethyl acetate (50 mL). The organic layers were combined and anhydrous sodium sulfate was added to this, filtered, and concentrated under reduced pressure to obtain [(2S)-1-({4-[(2-amino-4-chloro-5H-pyrrolo[3,2-d]pyrimidin-5-yl)methyl]-3-methoxyphenyl}methyl)pyrrolidin-2-yl]methanol (72 mg) as an oily substance.

Example 5

[(2S)-1-({4-[(2-Amino-4-chloro-5H-pyrrolo[3,2-d]pyrimidin-5-yl)methyl]-3-methoxyphenyl}methyl)pyrrolidin-2-yl]methanol (70 mg), DMSO (1 mL), DIPEA (0.16 mL) and pentane-1-thiol (0.1 mL) were added in a microwave vial and stirred under microwave irradiation at 100° C. for 6 hours. The reaction solution was allowed to cool to room temperature, added in water (20 mL) and extracted three times with ethyl acetate (20 mL). The organic layers were combined, washed with water and saturated saline, dried over anhydrous MgSO$_4$ and concentrated under reduced pressure. The residue obtained was purified by silica gel column chromatography (amino silica gel, ethyl acetate/hexane=50/50-100/0) to obtain {(2S)-1-[(4-{[2-amino-4-(pentylsulfanyl)-5H-pyrrolo[3,2-d]pyrimidin-5-yl]methyl}-3-methoxyphenyl)methyl]pyrrolidin-2-yl}methanol (35 mg) as an oily substance.

Production Examples 6-1

To a solution of 5-{[4-(chloromethyl)-2-methoxyphenyl]methyl}-$N^4$-pentyl-5H-pyrrolo[3,2-d]pyrimidine-2,4-diamine hydrochloride (0.1 g) in MeCN (3 mL), Palau'Chlor (registered trademark) (65 mg) was added at room temperature. The reaction mixture was stirred at the same temperature overnight and concentrated under reduced pressure. The residue was purified by silica gel column chromatography (DCM/methanol=9/1) to obtain 7-chloro-5-{[4-(chloromethyl)-2-methoxyphenyl]methyl}-$N^4$-pentyl-5H-pyrrolo[3,2-d]pyrimidine-2,4-diamine hydrochloride (60 mg) as a solid substance.

Example 6

To a solution of 7-chloro-5-{[4-(chloromethyl)-2-methoxyphenyl]methyl}-$N^4$-pentyl-5H-pyrrolo[3,2-d]pyrimidine-2,4-diamine hydrochloride (60 mg) in DMF (3 mL), DIPEA (0.061 mL) and [(2S)-pyrrolidin-2-yl]methanol (0.024 mL) were added at room temperature. The reaction mixture was stirred at the same temperature overnight and concentrated under reduced pressure. The crude product was purified by silica gel column chromatography (amino silica gel, methanol/ethyl acetate=1/99) to obtain {(2S)-1-[(4-{[2-amino-7-chloro-4-(pentylamino)-5H-pyrrolo[3,2-d]pyrimidin-5-yl]methyl}-3-methoxyphenyl)methyl]pyrrolidin-2-yl}methanol (33 mg) as a solid substance.

Production Examples 7-1

To a solution of 7-bromo-4-chloro-5H-pyrrolo[3,2-d]pyrimidin-2-amine (2.68 g) and cesium carbonate (1.78 g) in DMF (40 mL), methyl 4-(bromomethyl)-3-methoxybenzoate (1.42 g) was added under ice-cooling. The reaction mixture was stirred at room temperature for 4 hours. After the reaction mixture was diluted by adding a saturated ammonium chloride aqueous solution (200 mL) thereto under ice-cooling, the mixture was poured into ice water (600 mL). The solid generated was separated by filtration and washed with ethyl acetate/hexane (1/4, 500 mL) to obtain methyl 4-[(2-amino-7-bromo-4-chloro-5H-pyrrolo[3,2-d]pyrimidin-5-yl)methyl]-3-methoxybenzoate (4.44 g) as a solid substance.

Production Examples 7-2

To a suspension of LAH (288 mg) in THF (60 mL), 4-[(2-amino-7-bromo-4-chloro-5H-pyrrolo[3,2-d]pyrimidin-5-yl)methyl]-3-methoxybenzoate (4.4 g) was added under ice-cooling. The reaction mixture was stirred at the same temperature for 15 minutes and sodium sulfate decahydrate (15 g) was added to the mixture under ice-cooling. The suspension was stirred at room temperature for 5 hours and filtered to remove solid substances. The filtrate obtained was concentrated under reduced pressure and the crude product was dissolved in DMSO (30 mL). To the solution, DIPEA (4 mL) and pentan-1-amine (2 mL) were added.

The reaction mixture was stirred at 110° C. overnight and allowed to cool to room temperature. To the reaction mixture, a saturated ammonium chloride aqueous solution (40 mL) and ethyl acetate (100 mL) were added. The organic layer was washed three times with water (100 mL), once with saturated saline (100 mL), dried over anhydrous MgSO$_4$ and concentrated under reduced pressure. The crude product was purified by silica gel column chromatography (amino silica gel, ethyl acetate/hexane=50/50) to obtain (4-{[2-amino-7-bromo-4-(pentylamino)-5H-pyrrolo[3,2-d]pyrimidin-5-yl]methyl}-3-methoxyphenyl)methanol (1.4 g) as a solid substance.

Production Examples 7-3

To a solution of (4-{[2-amino-7-bromo-4-(pentylamino)-5H-pyrrolo[3,2-d]pyrimidin-5-yl]methyl}-3-methoxyphenyl)methanol (0.4 g) in THF (30 mL), thionyl chloride (0.13 mL) was added at 40° C. The reaction mixture was stirred at the same temperature for 2 hours and concentrated under reduced pressure. The residue obtained was diluted with MeCN (20 mL). The resultant solution was again concentrated under reduced pressure to obtain 7-bromo-5-{[4-(chloromethyl)-2-methoxyphenyl]methyl}-N$^4$-pentyl-5H-pyrrolo[3,2-d]pyrimidine-2,4-diamine hydrochloride (438 mg) as a solid substance.

Example 7

To a solution of [(2S)-pyrrolidin-2-yl]methanol (0.02 mL), DIPEA (0.1 mL) and TBAI (5 mg) in MeCN (3 mL), 7-bromo-5-{[4-(chloromethyl)-2-methoxyphenyl]methyl}-N$^4$-pentyl-5H-pyrrolo[3,2-d]pyrimidine-2,4-diamine hydrochloride (80 mg) was added at room temperature. The reaction mixture was stirred at 50° C. for 16 hours and concentrated under reduced pressure. The residue was purified by silica gel column chromatography (amino silica gel, methanol/chloroform=5/95) to obtain {(2S)-1-[(4-{[2-amino-7-bromo-4-(pentylamino)-5H-pyrrolo[3,2-d]pyrimidin-5-yl]methyl}-3-methoxyphenyl)methyl]pyrrolidin-2-yl}methanol (65 mg) as a solid substance.

Production Examples 8-1 tert-Butyl 4-{[4-(hydroxymethyl)-3-methoxyphenyl]methyl}piperazine-1-carboxylate (2.6 g) was obtained from methyl 4-(bromomethyl)-2-methoxybenzoate (5 g) in the same manner as in Production Examples 1-1 and 1-3, as an oily substance.

Production Examples 8-2

To a solution of methyl (6-methyl-4-oxo-4,5-dihydro-3H-pyrrolo[3,2-d]pyrimidin-2-yl)carbamate (1 g) in MeCN (20 mL), phosphorus oxychloride (892.86 μL) and DIPEA (1.57 mL) were added. The reaction mixture was stirred at 70° C. for one hour, allowed to cool to room temperature and poured in water (80 mL) in which sodium acetate (960 mg) was dissolved. The organic layer was concentrated under reduced pressure. The residue mixture was cooled to 0° C., filtered and washed with MeCN (40 mL). The residue mixture was cooled to 0° C., filtrated and washed with acetonitrile (40 mL). The solid substance obtained was dried under reduced pressure and purified by silica gel column chromatography (methanol/DCM=0/100-5/95) to obtain methyl (4-chloro-6-methyl-5H-pyrrolo[3,2-d]pyrimidin-2-yl)carbamate (300 mg) as a solid substance.

Production Examples 8-3

To a mixture of methyl (4-chloro-6-methyl-5H-pyrrolo[3,2-d]pyrimidin-2-yl)carbamate (300 mg), tert-butyl 4-{[4-(hydroxymethyl)-3-methoxyphenyl]methyl}piperazine-1-carboxylate (503.28 mg) and THF (10 mL), triphenylphosphine (980.93 mg) and DIAD (484.77 μL) were added. The reaction mixture was stirred at 25° C. for one hour. To the mixture, water (20 mL) was added, and thereafter, the resultant mixture was extracted three times with DCM (10 mL). The organic layers were combined, washed three times with saturated saline (5 mL), dried over anhydrous sodium sulfate, and concentrated under reduced pressure. The residue obtained was purified by silica gel column chromatography (methanol/DCM=0/100-5/95) to obtain tert-butyl 4-{[4-({4-chloro-2-[(methoxycarbonyl)amino]-6-methyl-5H-pyrrolo[3,2-d]pyrimidin-5-yl}methyl)-3-methoxyphenyl]methyl}piperazine-1-carboxylate (500 mg) as an oily substance.

Production Examples 8-4

To a solution of tert-butyl 4-{[4-({4-chloro-2-[(methoxycarbonyl)amino]-6-methyl-5H-pyrrolo[3,2-d]pyrimidin-5-yl}methyl)-3-methoxyphenyl]methyl}piperazine-1-carboxylate (500 mg) in 1,4-dioxane (6 mL), an aqueous sodium hydroxide solution (2 M, 2.73 mL) was added. The reaction mixture was stirred at 80° C. for 2 hours. To the reaction mixture, water (10 mL) was added. The mixture was extracted three times with DCM (10 mL). The organic layers were combined, washed three times with saturated saline (5 mL), dried over anhydrous sodium sulfate and concentrated under reduced pressure to obtain tert-butyl 4-({4-[(2-amino-4-chloro-6-methyl-5H-pyrrolo[3,2-d]pyrimidin-5-yl)methyl]-3-methoxyphenyl}methyl)piperazine-1-carboxylate (360 mg) as a solid substance.

Example 8

Using tert-butyl 4-({4-[(2-amino-4-chloro-6-methyl-5H-pyrrolo[3,2-d]pyrimidin-5-yl)methyl]-3-methoxyphenyl}methyl)piperazine-1-carboxylate (360 mg) in the same manner as in Production Example 1-6 and Example 2, 5-({2-methoxy-4-[(piperazin-1-yl)methyl]phenyl}methyl)-6-methyl-N$^4$-pentyl-5H-pyrrolo[3,2-d]pyrimidine-2,4-diamine hydrochloride (33.5 mg) was obtained as a solid substance.

Production Examples 9-1

To a solution of (4-{[2-amino-4-(pentylamino)-5H-pyrrolo[3,2-d]pyrimidin-5-yl]methyl}-3-methoxyphenyl)methanol (200 mg) in DCM (4 mL), thionyl chloride (0.4 mL) was added under ice-cooling. The reaction solution was stirred at room temperature for 2 hours and concentrated under reduced pressure. To the residue obtained, a saturated sodium hydrogen carbonate aqueous solution and DCM were added. The mixture was extracted with DCM by use of a phase separator. The extract was concentrated under reduced pressure. To the residue obtained, tert-butyl 4-(4,4,5,5-tetramethyl-1,3,2-dioxaborolan-2-yl)-3,6-dihydropyridine-1(2H)-carboxylate (168 mg), $PdCl_2$ (dppf)_$CH_2Cl_2$ (24 mg), potassium carbonate (150 mg), 1,4-dioxane (2 mL) and water (0.4 mL) were added. The resultant mixture was stirred under an argon atmosphere at 100° C. overnight and allowed to cool up to room temperature. To the mixture, water and chloroform were added. The mixture was extracted with chloroform by use of a phase separator. The extract was concentrated under reduced pressure. The residue obtained was purified by silica gel column chromatography (amino silica gel, chloroform/methanol=100/0-90/10) and silica gel column chromatography (chloroform/methanol=100/0-80/20) to obtain a solid substance (109.3 mg). To a solution of the solid substance (76 mg) in EtOAc (3 mL), 5% platinum-loaded carbon (about 50% water content, 38 mg) was added under an argon atmosphere. The mixture was stirred at room temperature for 2 days under a hydrogen atmosphere. The mixture was filtered with Celite (registered trademark) and concentrated under reduced pressure. The residue obtained was purified by silica gel column chromatography (chloroform/methanol=100/0-80/20) to obtain tert-butyl 4-[(4-{[2-amino-4-(pentylamino)-5H-pyrrolo[3,2-d]pyrimidin-5-yl]methyl}-3-methoxyphenyl)methyl]piperidine-1-carboxilate (65.2 mg) as a solid substance.

Example 9

To a solution of tert-butyl 4-[(4-{[2-amino-4-(pentylamino)-5H-pyrrolo[3,2-d]pyrimidin-5-yl]methyl}-3-methoxyphenyl)methyl]piperidine-1-carboxilate (62 mg) in DCM (2 mL), 4 M HCl/dioxane (0.6 mL) was added under ice-cooling. The reaction solution was stirred at room temperature overnight, and concentrated under reduced pressure. To the residue obtained, a mixed solvent (chloroform/methanol=5/1) and amino silica gel were added. The mixture was concentrated under reduced pressure. The residue obtained was purified by silica gel column chromatography (amino silica gel, chloroform/methanol=100/0-80/20) to obtain 5-({2-methoxy-4-[(piperidin-4-yl)methyl]phenyl}methyl)-$N^4$-pentyl-5H-pyrrolo[3,2-d]pyrimidine-2,4-diamine (41.9 mg) as a solid substance.

Example 10

A mixture of tert-butyl (3R)-4-[(4-{[2-amino-4-(pentylamino)-5H-pyrrolo[3,2-d]pyrimidin-5-yl]methyl}-3-methoxyphenyl)methyl]-3-(fluoromethyl)piperazine-1-carboxylate (460 mg) and 4 M HCl/dioxane (6 mL) in DCM (2 mL) were stirred at 20° C. for one hour. The mixture was concentrated under reduced pressure and the residue was purified by prep-HPLC (column: Xtimate C18 150×40 mm×10 μm, water (0.05% $NH_3/H_2O$)/MeCN=90/10-40/60) to obtain 5-[(4-{[(2R)-2-(fluoromethyl)piperazin-1-yl]methyl}-2-methoxyphenyl)methyl]-$N^4$-pentyl-5H-pyrrolo[3,2-d]pyrimidine-2,4-diamine (230 mg) as a solid substance.
(Production of Drug-Linker Conjugate)

Example L1

To a solution of 5-[(4-{[(2S)-2-(fluoromethyl)piperazin-1-yl]methyl}-2-methoxyphenyl)methyl]-$N^4$-pentyl-5H-pyrrolo[3,2-d]pyrimidine-2,4-diamine (0.18 g) in DMF (5 mL), 3-(2,5-dioxo-2,5-dihydro-1H-pyrrol-1-yl)propanoic acid (64.83 mg), HATU (291.49 mg) and DIPEA (0.2 mL) were added at 20° C. The reaction solution was stirred at the same temperature for 12 hours. To the reaction solution, water (50 mL) was added. The reaction solution was extracted three times with ethyl acetate (100 mL). The organic layers were combined and concentrated under reduced pressure. The residue was purified by prep-HPLC (column: Phenomenex Gemini-NX C18 75×30 mm×3 μm, water (0.1% TFA)-MeCN=100/0-60/40) to obtain 1-{3-[(3S)-4-[(4-{[2-amino-4-(pentylamino)-5H-pyrrolo[3,2-d]pyrimidin-5-yl]methyl}-3-methoxyphenyl)methyl]-3-(fluoromethyl)piperazin-1-yl]-3-oxopropyl}-1H-pyrrole-2,5-dione (trifluoroacetic acid) salt (108.5 mg) as a solid substance.

Example L3

To a mixture of 31-(2,5-dioxo-2,5-dihydro-1H-pyrrol-1-yl)-29-oxo-4,7,10,13,16,19,22,25-octaoxa-28-azahene 2,5-dioxopyrrolidin-1-yl triacontane-1-acid 2,5-dioxopyrrolidin-1-yl (24 mg), DIPEA (15 μL) and NMP (1 mL), 5-[(4-{[(2S)-2-(fluoromethyl)piperazin-1-yl]methyl}-2-methoxyphenyl)methyl]-$N^4$-pentyl-5H-pyrrolo[3,2-d]pyrimidine-2,4-diamine (15 mg) was added under ice-cooling and stirred at room temperature for one hour. The reaction mixture was purified by reversed-phase silica gel column chromatography (ODS, water (0.1% TFA)/MeCN (0.1% TFA)=100/0-50/50) and lyophilized to obtain N-{27-[(3S)-4-[(4-{[2-amino-4-(pentylamino)-5H-pyrrolo[3,2-d]pyrimidin-5-yl]methyl}-3-methoxyphenyl)methyl]-3-(fluoromethyl)piperazin-1-yl]-27-oxo-3,6,9,12,15,18,21,24-octaoxaheptacosan-1-yl}-3-(2,5-dioxo-2,5-dihydro-1H-pyrrol-1-yl)propanamide trifluoroacetate (25 mg) as a solid substance.

Example L4

To a solution of 1-(2-hydroxyethyl)-1H-pyrrole-2,5-dione (38 mg) in DCM (1 mL), DMP (112 mg) was added. The reaction mixture was stirred at room temperature overnight. To the reaction mixture, DCM (2 mL) and DMP (112 mg) were added. The reaction mixture was stirred at room temperature overnight. To the reaction mixture, a 10% sodium sulfite aqueous solution, a saturated sodium hydrogen carbonate aqueous solution and chloroform were added under ice-cooling. The reaction mixture was extracted with chloroform by use of a phase separator. The extract was concentrated under reduced pressure. To the residue obtained, 5-({2-methoxy-4-[(piperazin-1-yl)methyl]phenyl}methyl)-4-(pentylsulfanyl)-5H-pyrrolo[3,2-d]pyrimidin-2-amine (30 mg), THF (2 mL), acetic acid (0.01 mL) and sodium triacetoxyborohydride (70 mg) were added. The reaction mixture was stirred at room temperature overnight. To the reaction mixture, water and a saturated sodium hydrogen carbonate aqueous solution were added under ice-cooling. The reaction mixture was extracted with a mixed solvent (chloroform/MeCN=5/1). The organic layer was dried over anhydrous $MgSO_4$ and concentrated under reduced pressure. The residue obtained was purified by reversed-phase silica gel column chromatography (ODS, water (0.1% TFA)/MeCN (0.1% TFA)=100/0-0/100) to obtain 1-(2-{4-[(4-{[2-amino-4-(pentylsulfanyl)-5H-pyrrolo[3,2-d]pyrimidin-5-yl]methyl}-3-methoxyphenyl)methyl]piperazin-1-yl}ethyl)-1H-pyrrole-2,5-dione(trifluoroacetic acid) salt (13.2 mg) as a solid substance.

Production Examples L5-1

To a mixed solution of benzyl (2S)-2-(hydroxymethyl)pyrrolidine-1-carboxylate (0.94 g), DCM (6 mL) and DIPEA (2 mL), a solution of triphosgene (593 mg) in DCM (4 mL) was added under ice-cooling. The reaction mixture was stirred at the same temperature for 3 hours. Thereafter, tert-butyl (2-aminoethyl)carbamate (704 mg) was added to the reaction mixture at 0° C. The reaction mixture was stirred at room temperature overnight. To the reaction solution, a saturated ammonium chloride aqueous solution (10 mL) was added. The reaction solution was extracted twice with DCM (10 mL). The organic layers were combined, dried over anhydrous $MgSO_4$ and concentrated under reduced pressure. The residue obtained was purified by silica gel column chromatography (ethyl acetate/hexane=5/95-80/20) to obtain benzyl (2S)-2-(10,10-dimethyl-3,8-dioxo-2,9-dioxa-4,7-diazaundecane-1-yl)pyrrolidine-1-carboxylate (1.07 g) as an oily substance.

Production Examples L5-2

A solution of 10% palladium-supported carbon (50% water content, 50 mg) and benzyl (2S)-2-(10,10-dimethyl-3,8-dioxo-2,9-dioxa-4,7-diazaundecane-1-yl)pyrrolidine-1-carboxylate (1.05 g) in methanol (30 mL) was stirred at room temperature under a hydrogen atmosphere for 20 hours and filtered by Celite (registered trademark). After Celite (registered trademark) was washed with methanol, the filtrate was concentrated under reduced pressure and dried to obtain tert-butyl [(2S)-pyrrolidin-2-yl]methyl ethane-1,2-diylbiscarbamate (710 mg) as an oily substance.

Production Examples L5-3

To a solution of tert-butyl [(2S)-pyrrolidin-2-yl]methyl ethane-1,2-diylbiscarbamate (84 mg) and DIPEA (0.15 mL) in DMF (5 mL), 7-chloro-5-{[4-(chloromethyl)-2-methoxyphenyl]methyl}-$N^4$-pentyl-5H-pyrrolo[3,2-d]pyrimidine-2,4-diamine hydrochloride (110 mg) was added. The reaction mixture was stirred at room temperature for 16 hours and concentrated under reduced pressure. The residue was purified by silica gel column chromatography (amino silica gel, methanol/chloroform=3/97) to obtain {(2S)-1-[(4-{[2-amino-7-chloro-4-(pentylamino)-5H-pyrrolo[3,2-d]pyrimidin-5-yl]methyl}-3-methoxyphenyl)methyl]pyrrolidin-2-yl}methyl tert-butyl ethane-1,2-diylbiscarbamate (87 mg) as a solid substance.

Example L5

To a solution of {(2S)-1-[(4-{[2-amino-7-chloro-4-(pentylamino)-5H-pyrrolo[3,2-d]pyrimidin-5-yl]methyl}-3-methoxyphenyl)methyl]pyrrolidin-2-yl}methyl tert-butyl ethane-1,2-diylbiscarbamate (84 mg) in ethyl acetate (2 mL), 4 M HCl/EtOAc (2 mL) was added. The reaction mixture was stirred at room temperature for 4 hours. After concentration under reduced pressure, the crude product was dissolved in THF (2 mL) and a sodium hydrogen carbonate aqueous solution (1 mL) was added, and then, methyl 2,5-dioxo-2,5-dihydro-1H-pyrrole-1-carboxylate (70 mg) was added. After the mixture was stirred at room temperature for 4 hours, the reaction solution was directly purified by reversed-phase silica gel column chromatography (ODS, MeCN/water=0/100-100/0). Fractions containing a desired product were collected and purified again by silica gel column chromatography (methanol/chloroform=0/100-10/90) to obtain [2-(2,5-dioxo-2,5-dihydro-1H-pyrrol-1-yl)ethyl]carbamate{(2S)-1-[(4-{[2-amino-7-chloro-4-(pentylamino)-5H-pyrrolo[3,2-d]pyrimidin-5-yl]methyl}-3-methoxyphenyl)methyl]pyrrolidin-2-yl}methyl (6 mg) as a solid substance.

Production Examples L6-1

To a solution of LAH (535 mg) in THF (50 mL), tert-butyl (2S)-2-[(2-tert-butoxy-2-oxoethoxy)methyl]pyrrolidine-1-carboxylate (2.95 g) was slowly added under ice-cooling. The reaction solution was stirred at room temperature for 30 minutes and cooled on ice. To the reaction solution, water (0.5 mL) was added, and then, a 1 M sodium hydroxide aqueous solution (0.5 mL) and an anhydrous $MgSO_4$ were added. The reaction solution was stirred for 30 minutes and filtered. The filtrate was concentrated under reduced pressure to obtain tert-butyl (2S)-2-[(2-hydroxyethoxy)methyl]pyrrolidine-1-carboxylate (1.41 g) as an oily substance.

Production Examples L6-2

To a solution of tert-butyl (2S)-2-[(2-hydroxyethoxy)methyl]pyrrolidine-1-carboxylate (630 mg), triphenylphosphine (1.35 g) and phthalimide (755 mg) in THF (10 mL), DEAD (2.2 mol/L, 2.4 mL) was added dropwise over 5 to 10 minutes. The reaction mixture was stirred for 16 hours and the precipitate was filtered. The filtrate was concentrated under reduced pressure and the crude product was purified by silica gel column chromatography (ethyl acetate/hexane=20/80) to obtain tert-butyl (2S)-2-{[2-(1,3-dioxo-1,3-dihydro-2H-isoindol-2-yl)ethoxy]methyl}pyrrolidine-1-carboxylate (911 mg) as a solid substance.

Production Examples L6-3

To a solution of tert-butyl (2S)-2-{[2-(1,3-dioxo-1,3-dihydro-2H-isoindol-2-yl)ethoxy]methyl}pyrrolidine-1-carboxylate (911 mg) in ethyl acetate (20 mL), 4M HCl/EtOAc was added under ice-cooling, (4 mL) in a nitrogen atmosphere. The reaction mixture was stirred at room temperature for 16 hours. The solid substance generated was separated by filtration to obtain 2-(2-{[(2S)-pyrrolidin-2-yl]methoxy}ethyl)-1H-isoindole-1,3(2H)-dione hydrochloride (751 mg) a solid substance.

Production Examples L6-4

To a solution of 2-(2-{[(2S)-pyrrolidin-2-yl]methoxy}ethyl)-1H-isoindole-1,3(2H)-dione hydrochloride (100 mg) in DMF (5 mL), DIPEA (0.22 mL), TBAI (6 mg) and 7-chloro-5-{[4-(chloromethyl)-2-methoxyphenyl]methyl}-$N^4$-pentyl-5H-pyrrolo[3,2-d]pyrimidine-2,4-diamine hydrochloride (148 mg) were added. The reaction mixture was stirred at room temperature overnight and concentrated under reduced pressure. The crude product obtained was dissolved in ethanol (3 mL), and then, hydrazine monohydrate (35 mg) was added at 60° C. The reaction mixture was stirred at the same temperature for 5 hours. A solid substance was separated by Celite (registered trademark) filtration. After ethanol (50 mL) washing, the filtrate was concentrated under reduced pressure. The crude product obtained was purified by silica gel column chromatography (amino silica gel, chloroform/methanol=98:2) to obtain 5-{[4-({(2S)-2-[(2-aminoethoxy)methyl]pyrrolidin-1- yl}methyl)-2-methoxyphenyl]methyl}-7-chloro-$N^4$-pentyl-5H-pyrrolo[3,2-d]pyrimidine-2,4-diamine (145 mg) as a solid substance.

Example L6

To a solution of 5-{[4-({(2S)-2-[(2-aminoethoxy)methyl]pyrrolidin-1-yl}methyl)-2-methoxyphenyl]methyl}-7-chloro-$N^4$-pentyl-5H-pyrrolo[3,2-d]pyrimidine-2,4-diamine (140 mg) in 1,4-dioxane (2 mL), a 0.85 M sodium hydrogen carbonate aqueous solution (1.5 mL) and methyl 2,5-dioxo-2,5-dihydro-1H-pyrrole-1-carboxylate (30 mg) were added at room temperature. The reaction mixture was stirred at the same temperature for 30 minutes. To the reaction mixture, water (10 mL) was added. The reaction mixture was extracted twice with chloroform/methanol (4:1, 10 mL). The organic layers were combined, dried over anhydrous MgSO$_4$ and concentrated under reduced pressure. The residue was purified by silica gel column chromatography (methanol/chloroform=0/100-10/90) to obtain 1-[2-({(2S)-1-[(4-{[2-amino-7-chloro-4-(pentylamino)-5H-pyrrolo[3,2-d]pyrimidin-5-yl]methyl}-3-methoxyphenyl)methyl]pyrrolidin-2-yl}methoxy)ethyl]-1H-pyrrole-2,5-dione (96 mg) as an oily substance.

Example LA: Production of Antibody-Drug Conjugate

Common Operation A: Washing and Concentration of Antibody-Drug Conjugate Aqueous Solution An antibody-drug conjugate solution was put in a container, Amicon ultra-15 (10,000 MWCO, Millipore Co.), and D-PBS phosphate buffered saline was added such that the volume of the solution became 15 mL. The mixture was washed and concentrated by a centrifugal operation (3,000 G for 15 to 90 minutes) using a centrifuge to wash and concentrate an antibody-drug conjugate solution.

Common Operation B: Purification of Antibody-Drug Conjugate

One to three PD-10 columns were equilibrated with commercially available D-PBS (Cat. No. 045-29795, Fujifilm Wako). On each of the PD-10 columns, a solution for an antibody-drug conjugate reaction (about 300 µL to 2.5 mL) was placed. Elution was carried out with about 5 mL of D-PBS and an eluted fraction was separately taken in a unit of 500 µL. The fractions containing an antibody were washed and concentrated by repeating common operation A once or twice. The solution collected were filtered by a membrane filter to obtain an antibody-drug conjugate.

Common Operation C: Determination of Drug Concentration of Antibody-Drug Conjugate The concentration of a drug in an antibody-drug conjugate was calculated in accordance with the BCA method using, e.g., Thermo Scientific Pierce™ BCA Protein Assay Kit. A calibration curve was prepared based on 562 nm-absorbance of an anti-human CLDN6 (hCLDN6) antibody to which a (drug) compound was not bound. Based on the absorbance of an anti-hCLDN6-TLR7/8 dual agonist antibody-drug conjugate sample at 562 nm, the concentration of the drug was calculated.

Common Operation D: Determination of the DAR in Anti-hCLDN6 Antibody-Drug Conjugate Containing TLR7/8 Dual Agonist The DAR of an anti-hCLDN6-TLR7/8 dual agonist antibody-drug conjugate was calculated based on the deconvolution mass spectrum obtained by SEC-MS measurement. To LC/MS, such as Waters Xevo G2-XS, to which Waters ACQUITY UPLC I-Class system was connected, a deglycosylated antibody-drug conjugate sample was injected. Measurement data were analyzed by Waters UNIFI. From the deconvolution mass spectrum obtained by the analysis, the spectral intensity values of MS peaks of antibody-TLR7/8 dual agonist antibody-drug conjugates were obtained. An average DAR was calculated.

Common Operation E: Measurement of Monomer Purity of Anti-hCLDN6 Antibody-Drug Conjugate Containing TLR7/8 Dual Agonist The monomer purity of an anti-hCLDN6-TLR7/8 dual agonist antibody-drug conjugate was calculated based on a chromatograph obtained by SEC measurement. Using a YMC-SEC MAB column, 100 mM potassium phosphate and 200 mM sodium chloride buffer (pH 7.0)/2-propanol (85:15) was fed at a flow rate of 0.165 mL/minute to elute an anti-hCLDN6-TLR7/8 dual agonist antibody-drug conjugate. The absorbance of the eluted fraction at UV 280 nm was detected. The value of integral of each peak was obtained and a monomer purity was calculated.

Example L1A1

A 13.57 mg/mL Ab1 antibody solution (147 µL) was put in a 1.5 mL Eppendorf tube and the concentration of an antibody was adjusted to 2 mg/mL with PBS6.2/EDTA (853 µL). Two antibody solutions in total were prepared in the same manner. To each of the solutions, a 0.2 M disodium hydrogen phosphate aqueous solution (51.5 µL) and a 2 mM TCEP aqueous solution (31.9 µL) were added. The reaction solutions were incubated at 37° C. for one hour. Subsequently, a 2 mM DMSO solution (63.8 µL) of 1-{3-[(3S)-4-[(4-{[2-amino-4-(pentylamino)-5H-pyrrolo[3,2-d]pyrimidin-5-yl]methyl}-3-methoxyphenyl)methyl]-3-(fluoromethyl)piperazin-1-yl]-3-oxopropyl}-1H-pyrrole-2,5-dione (trifluoroacetic acid) salt was added to each of the reaction solutions. The reaction solutions were allowed to stand still at room temperature for 40 minutes. Subsequently, a 20 mM NAC aqueous solution (12.3 µL) was added to the reaction solutions, which were allowed to stand still at room temperature for 20 minutes, to terminate a reaction of a drug linker. The (total) two reaction solutions were subjected to purification according to common operation B to obtain solutions containing an antibody-drug conjugate.

Separately, a 13.57 mg/mL Ab1 antibody solution (147 µL) was put in a 1.5 mL Eppendorf tube and the concentration of the antibody was adjusted with a PBS6.2/EDTA (853 µL) to 2 mg/mL. Three antibody solutions in total were prepared in the same manner. To each of the solutions, a 0.2 M disodium hydrogen phosphate aqueous solution (51.5 µL) and a 2 mM TCEP aqueous solution (31.9 µL) were added. The reaction solutions were incubated at 37° C. for one hour. Subsequently, a 2 mM DMSO solution (63.8 µL) of 1-{3-[(3S)-4-[(4-{[2-amino-4-(pentylamino)-5H-pyrrolo[3,2-d]pyrimidin-5-yl]methyl}-3-methoxyphenyl)methyl]-3-(fluoromethyl)piperazin-1-yl]-3-oxopropyl}-1H-pyrrole-2,5-dione (trifluoroacetic acid) salt was added to each of the three solutions. The reaction solutions were allowed to stand still at room temperature for 40 minutes. Subsequently, a 20 mM NAC aqueous solution (12.3 µL) was added to the reaction solutions, which were allowed to stand still at room temperature for 20 minutes, to terminate a reaction of a drug linker. The three reaction solutions were subjected to purification according to common operation B to obtain solutions containing an antibody-drug conjugate.

The two types of solutions each containing an antibody-drug conjugate were mixed and subjected twice to common operation A to perform washing and concentration. The solution was recovered and filtered by a membrane filter. The filtrate was diluted with D-PBS up to a volume of 1.8 mL. It was confirmed by common operations C and D that the solution is a 3.88 mg/mL solution containing the title antibody-drug conjugate (DAR 3.44).

Example L1A2

A 14.72 mg/mL Ab2 antibody solution (135.9 μL) was put in a 1.5 mL Eppendorf tube and the concentration of an antibody was adjusted to 2 mg/mL with PBS6.2/EDTA (864.1 μL). Three antibody solutions in total were prepared in the same manner. To each of the solutions, a 0.2 M disodium hydrogen phosphate aqueous solution (51.5 μL) and a 2 mM TCEP aqueous solution (31.9 μL) were added. The reaction solutions were incubated at 37° C. for one hour. Subsequently, a 2 mM DMSO solution (63.8 μL) of 1-{3-[(3S)-4-[(4-{[2-amino-4-(pentylamino)-5H-pyrrolo[3,2-d]pyrimidin-5-yl]methyl}-3-methoxyphenyl)methyl]-3-(fluoromethyl)piperazin-1-yl]-3-oxopropyl}-1H-pyrrole-2,5-dione (trifluoroacetic acid) salt was added to each of the reaction solutions. The reaction solutions were allowed to stand still at room temperature for 40 minutes. Subsequently, a 20 mM NAC aqueous solution (12.3 μL) was added to the reaction solutions, which were allowed to stand still at room temperature for 20 minutes, to terminate a reaction of a drug linker. The three reaction solutions were subjected to purification according to common operation B to obtain 1.25 mL of solutions containing an antibody-drug conjugate. It was confirmed by common operations C and D that the solution is a 4.61 mg/mL solution containing title antibody-drug conjugate (DAR 4.02).

Example L5A1

A 13.57 mg/mL Ab1 antibody solution (147 μL) was put in a 1.5 mL Eppendorf tube and the concentration of an antibody was adjusted to 2 mg/mL with PBS6.2/EDTA (853 μL). Five antibody solutions in total were prepared in the same manner. To each of the solutions, 0.2 M disodium hydrogen phosphate aqueous solution (51.5 μL) and a 2 mM TCEP aqueous solution (31.9 μL) were added. The reaction solutions were incubated at 37° C. for one hour. Subsequently, a 2 mM DMSO solution (63.8 μL) of {(2S)-1-[(4-{[2-amino-7-chloro-4-(pentylamino)-5H-pyrrolo[3,2-d]pyrimidin-5-yl]methyl}-3-methoxyphenyl)methyl]pyrrolidin-2-yl}methyl[2-(2,5-dioxo-2,5-dihydro-1H-pyrrol-1-yl)ethyl]carbamate was added to each of the reaction solutions. The reaction solutions were allowed to stand still at room temperature for 40 minutes. Subsequently, a 20 mM NAC aqueous solution (12.3 μL) was added to the reaction solutions, which were allowed to stand still at room temperature for 20 minutes, to terminate a reaction of a drug linker. The five reaction solutions were subjected to purification according to common operation B to obtain 1.85 mL of solutions containing an antibody-drug conjugate. It was confirmed by common operations C and D that the solution is a 4.55 mg/mL solution containing the title antibody-drug conjugate (DAR 2.95).

Example L7A1

A 13.57 mg/mL Ab1 antibody solution (147 μL) was put in a 1.5 mL Eppendorf tube and the concentration of an antibody was adjusted to 2 mg/mL with PBS6.2/EDTA (853 μL). Two antibody solutions in total were prepared in the same manner. To each of the solutions, a 0.2 M disodium hydrogen phosphate aqueous solution (51.5 μL) and a 2 mM TCEP aqueous solution (31.9 μL) were added. The reaction solution was incubated at 37° C. for one hour. Subsequently, a 2 mM DMSO solution (63.8 μL) of N-[(4-{[2-amino-4-(pentylamino)-5H-pyrrolo[3,2-d]pyrimidin-5-yl]methyl}-3-methoxyphenyl)methyl]-N-cyclopropyl-3-(2,5-dioxo-2,5-dihydro-1H-pyrrol-1-yl)propanamide (trifluoroacetic acid) salt was added to each of the reaction solutions. The reaction solutions were allowed to stand still at room temperature for 40 minutes. Subsequently, a 20 mM NAC aqueous solution (12.3 μL) was added to the reaction solutions, which were allowed to stand still at room temperature for 20 minutes, to terminate a reaction of a drug linker. The two reaction solutions were subjected to purification according to common operation B to obtain solutions containing an antibody-drug conjugate.

Separately, a 13.57 mg/mL Ab1 antibody solution (147 μL) was put in a 1.5 mL Eppendorf tube and the concentration of the antibody was adjusted with a PBS6.2/EDTA (853 μL) to 2 mg/mL. Three antibody solutions in total were prepared in the same manner. To each of the solutions, a 0.2 M disodium hydrogen phosphate aqueous solution (51.5 μL) and a 2 mM TCEP aqueous solution (31.9 μL) were added. The reaction solution was incubated at 37° C. for one hour. Subsequently, a 2 mM DMSO solution (63.8 μL) of N-[(4-{[2-amino-4-(pentylamino)-5H-pyrrolo[3,2-d]pyrimidin-5-yl]methyl}-3-methoxyphenyl)methyl]-N-cyclopropyl-3-(2,5-dioxo-2,5-dihydro-1H-pyrrol-1-yl)propanamide (trifluoroacetic acid) salt was added to each of the three solutions. The reaction solutions were allowed to stand still at room temperature for 40 minutes. Subsequently, a 20 mM NAC aqueous solution (12.3 μL) was added to the reaction solutions, which were allowed to stand still at room temperature for 20 minutes, to terminate a reaction of a drug linker. The three reaction solutions were subjected to purification according to common operation B to obtain solutions containing an antibody-drug conjugate.

The two types of solutions containing an antibody-drug conjugate were mixed and subjected twice to common operation A to perform washing and concentration. The solution was recovered, and filtered by a membrane filter. The filtrate was diluted with D-PBS up to a volume of 1.8 mL. It was confirmed by common operations C and D that the solution is a 4.52 mg/mL solution containing the title antibody-drug conjugate (DAR 3.28).

The compounds or salts thereof or antibody-drug conjugates or salts thereof (set forth in Production Examples and Examples and listed in the following tables) were produced in accordance with or in the same manner as in the methods described in the above Production Examples and Examples.

TABLE 3-1
| NUM | STR |
|---|---|
| PEx1-1 | 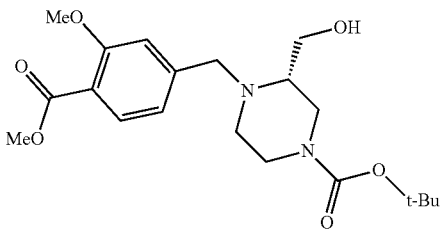 |
| PEx1-2 | 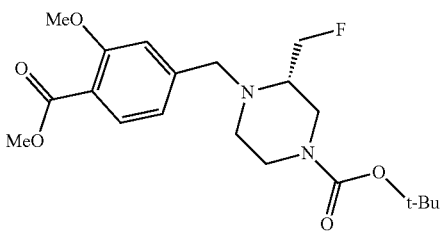 |
| PEx1-3 | 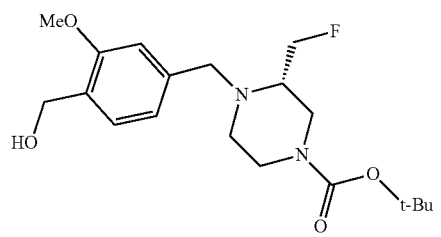 |
| PEx1-4 | 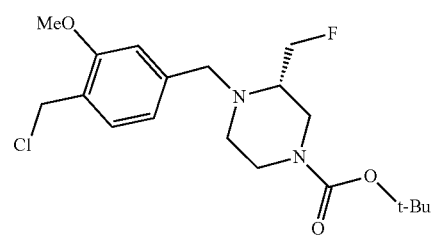 |
| PEx1-5 | 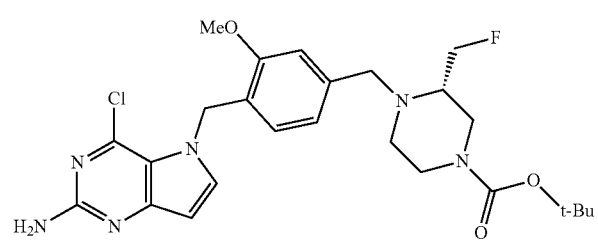 |
| PEx1-6 | 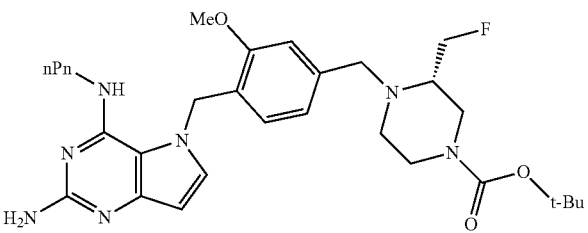 |

TABLE 3-1-continued

| NUM | STR |
|---|---|
| Ex1 | (structure) |
| PEx2-1 | (structure) |
| PEx2-2 | (structure) |
| PEx2-3 | (structure) |
| PEx2-4 | (structure) |
| Ex2/ TFA | (structure) |

TABLE 3-1-continued
| NUM | STR |
|---|---|
| PEx3-1 | 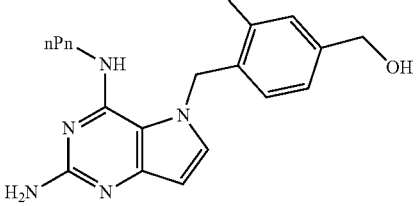 |
| PEx3-2 | 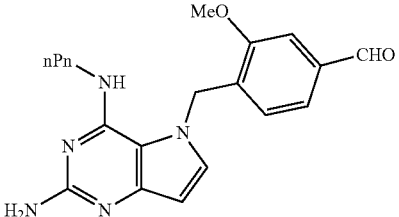 |
TABLE 3-2
| NUM | STR |
|---|---|
| Ex3 | 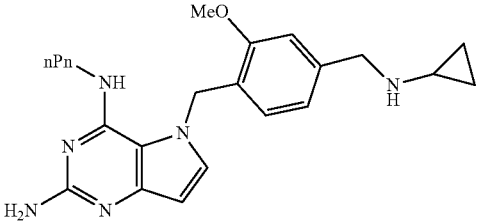 |
| PEx4-1 | 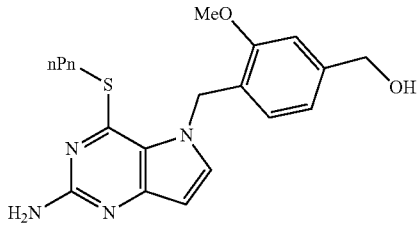 |
| Ex4 | 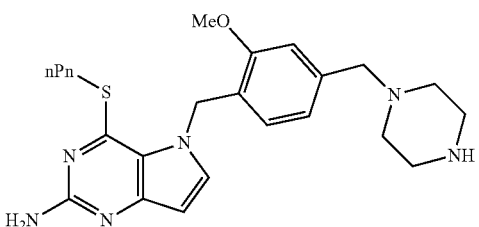 |

TABLE 3-2-continued

| NUM | STR |
|---|---|
| PEx5-1 | |
| Ex5 | |
| PEx6-1/ HCl | |
| Ex6 | |
| PEx7-1 | |

TABLE 3-2-continued

| NUM | STR |
|---|---|
| PEx7-2 | 2-amino-7-bromo-5-[[4-(hydroxymethyl)-2-methoxy-phenyl]methyl]-N-pentyl-pyrrolo[3,2-d]pyrimidin-4-amine |
| PEx7-3/HCl | 2-amino-7-bromo-5-[[4-(chloromethyl)-2-methoxy-phenyl]methyl]-N-pentyl-pyrrolo[3,2-d]pyrimidin-4-amine |
| Ex7 | 2-amino-7-bromo-5-[[4-[[(2S)-2-(hydroxymethyl)pyrrolidin-1-yl]methyl]-2-methoxy-phenyl]methyl]-N-pentyl-pyrrolo[3,2-d]pyrimidin-4-amine |
| PEx8-1 | tert-butyl 4-[[4-(hydroxymethyl)-3-methoxy-phenyl]methyl]piperazine-1-carboxylate |
| PEx8-2 | methyl N-(4-chloro-6-methyl-5H-pyrrolo[3,2-d]pyrimidin-2-yl)carbamate |
| PEx8-3 | tert-butyl 4-[[4-[[4-chloro-2-(methoxycarbonylamino)-6-methyl-pyrrolo[3,2-d]pyrimidin-5-yl]methyl]-3-methoxy-phenyl]methyl]piperazine-1-carboxylate |

TABLE 3-3

| NOM | STR |
|---|---|
| PEx8-4 | (structure) |
| Ex8/HCl | (structure) |
| PEx9-1 | (structure) |
| Ex9 | (structure) |
| PEx10-1 | (structure) |
| PEx10-2 | (structure) |

TABLE 3-3-continued
| NOM | STR |
|---|---|
| PEx10-3 | 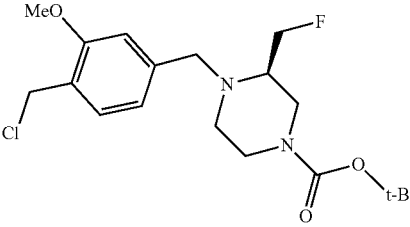 |
| PEx10-4 | 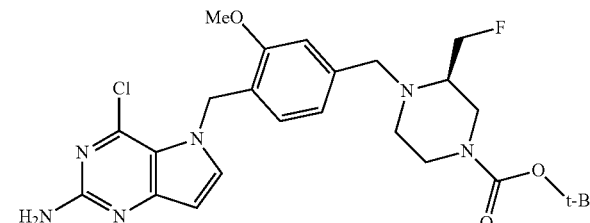 |
| PEx10-5 | 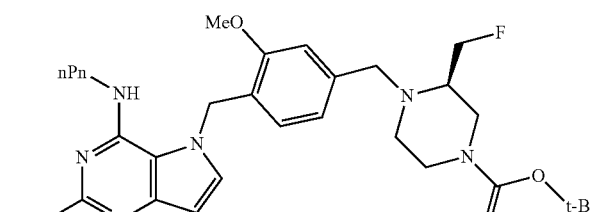 |
| Ex 10 | 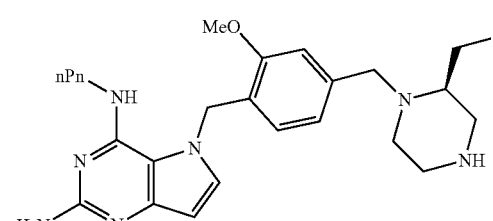 |
| Ex11 | 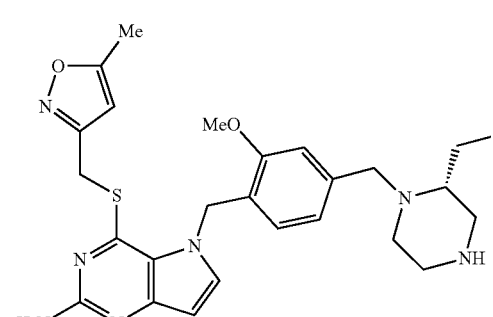 |
| Ex12 | 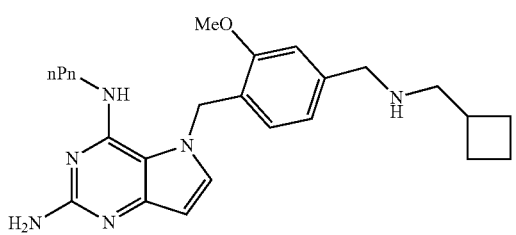 |

TABLE 3-3-continued
| NOM | STR |
|---|---|
| Ex13 | 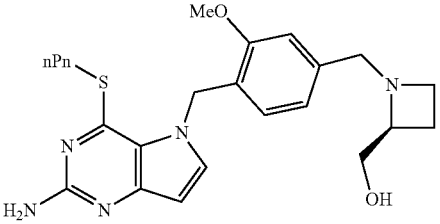 |
| Ex 14 | 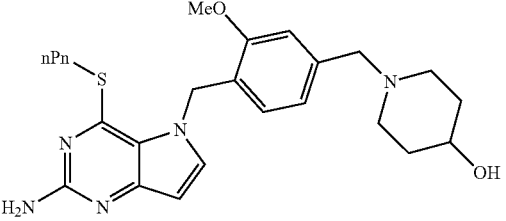 |
TABLE 3-4
| NUM | STR |
|---|---|
| Ex15 | 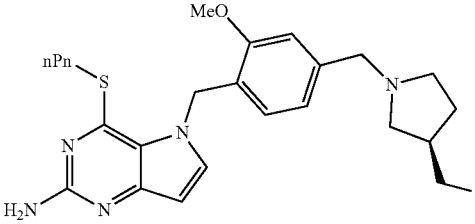 |
| Ex17 | 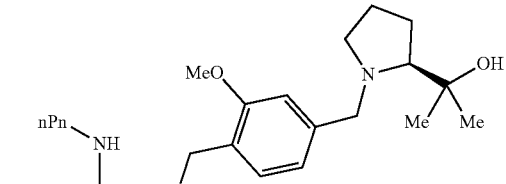 |
TABLE 3-4-continued
| NUM | STR |
|---|---|
| Ex18/ TFA | 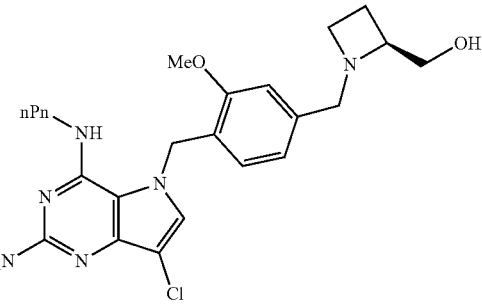 |
TABLE 4-1
| NUSS | STR |
|---|---|
| ExL1/ TFA | 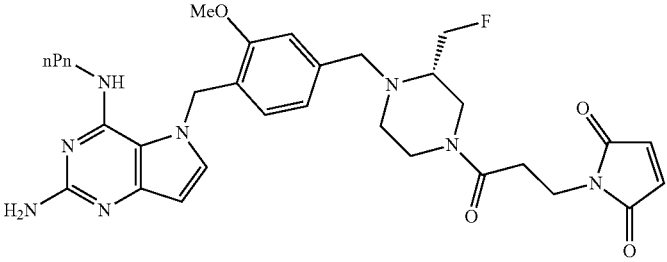 |

TABLE 4-1-continued
| NUSS | STR |
|---|---|
| ExL3/TFA | 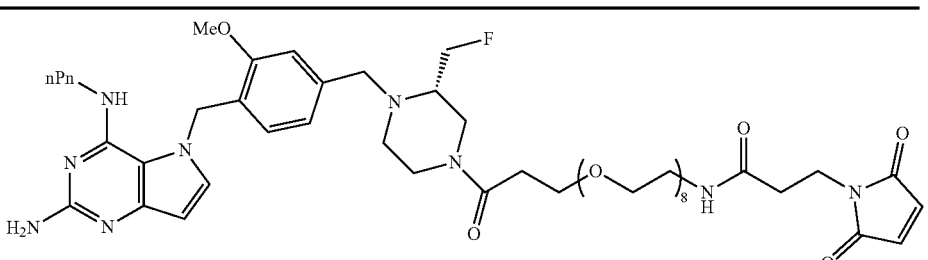 |
| ExL4/TFA | 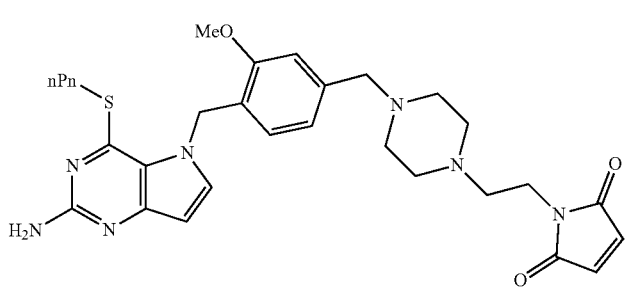 |
| PEXL5-1 | 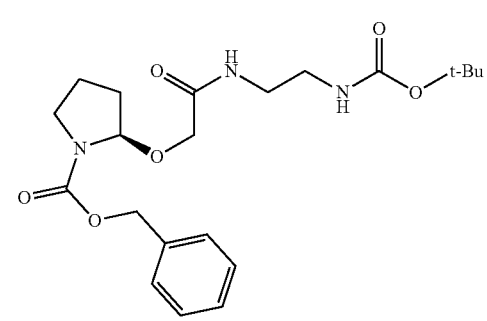 |
| PERL5-2 | 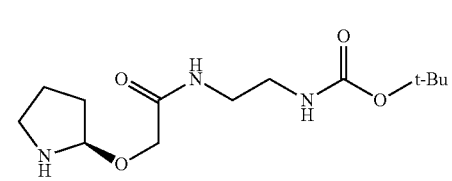 |
TABLE 4-2
| NUM | STR |
|---|---|
| PExLS-3 | 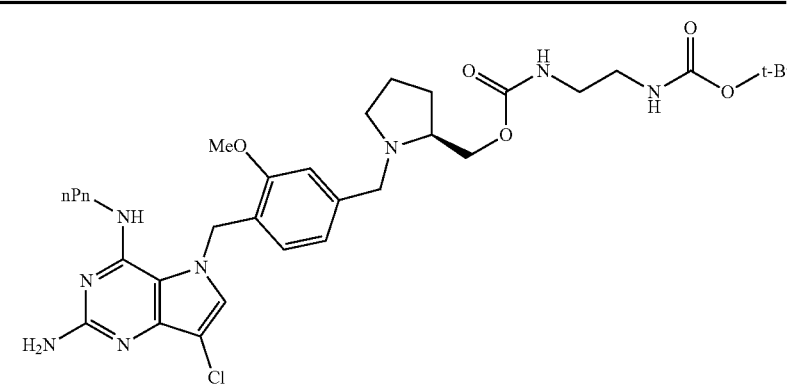 |

TABLE 4-2-continued
| NUM | STR |
|---|---|
| ExL5 | 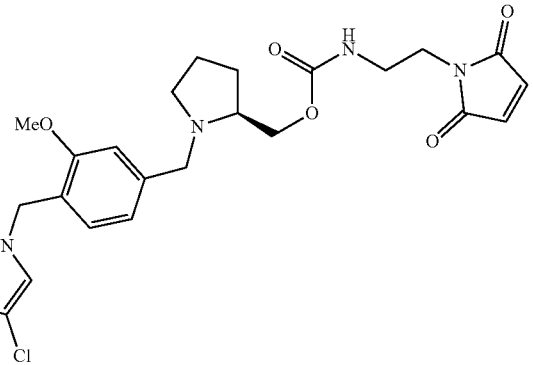 |
| PExL6-1 | 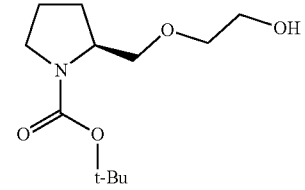 |
| PExL6-2 | 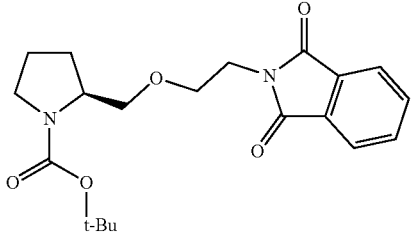 |
| PEXL6-3/ HCl | 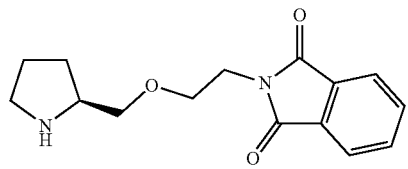 |
| PExL6-4 | 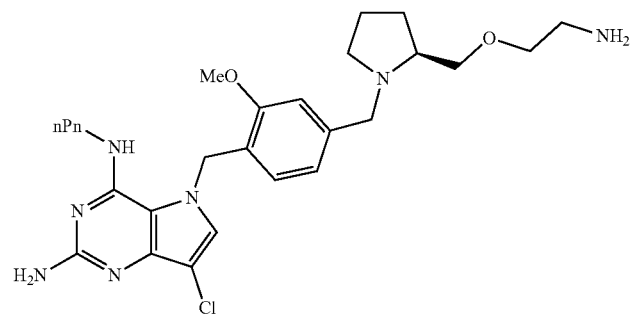 |

Table 4-3

| NUM | STR |
|---|---|
| ExL6 | (structure) |
| ExL7/ TFA | (structure) |
| ExL8/ TFA | (structure) |
| ExL9/ TFA | (structure) |
| ExL10/ TFA | (structure) |

TABLE 5
| NUM | STR |
|---|---|
| ExL1A1 | 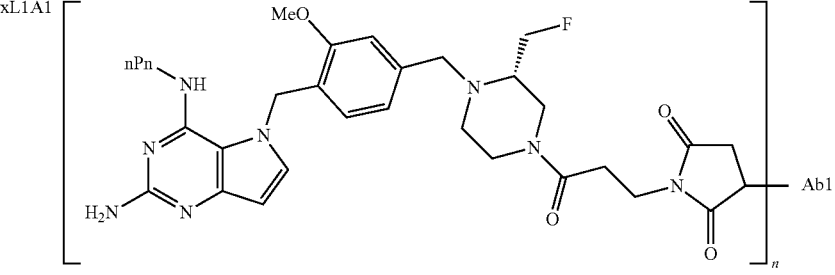 |
| ExL1A2 | 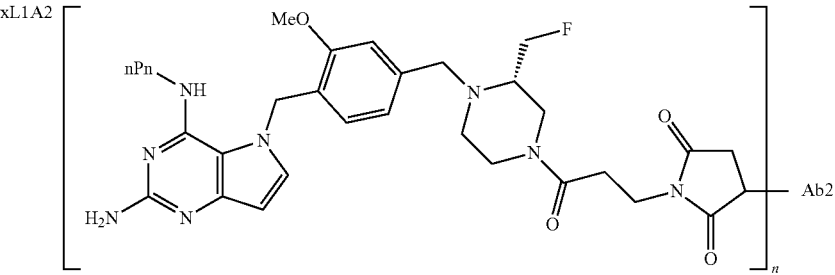 |
| ExL5A1 | 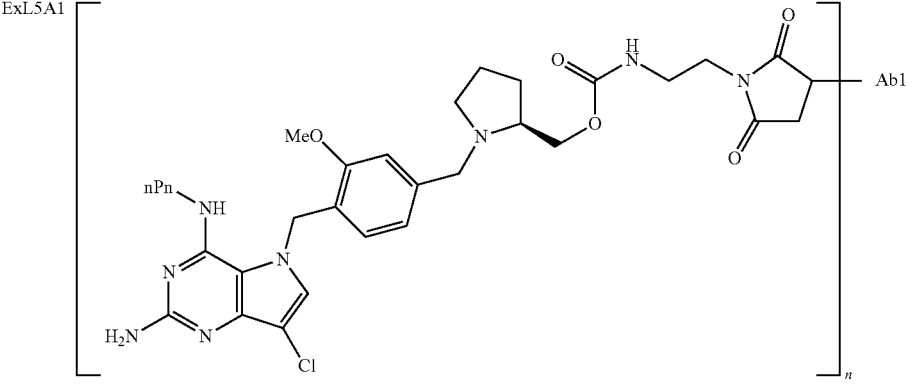 |
| ExL7A1 | 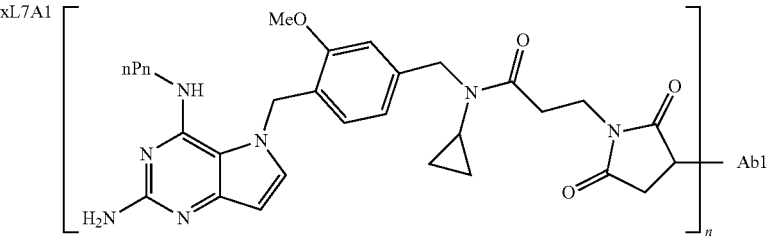 |
| ExL9A1 | 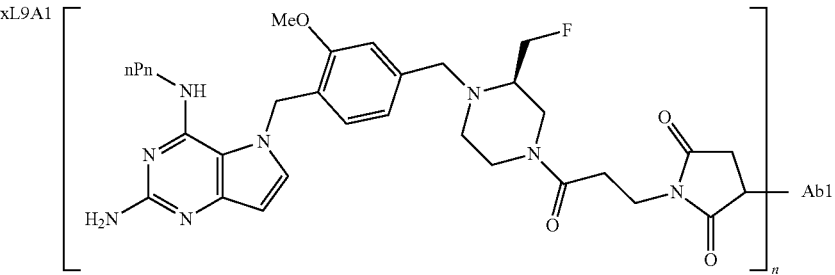 |

TABLE 6-1

| NUM | REF | DAT |
|---|---|---|
| PEx1-1 | PEx1-1 | ESI+: 395.3 |
| PEx1-2 | PEx1-2 | ESI+: 397.3 |
| PEx1-3 | PEx1-3 | ESI+: 369.2 |
| PEx1-4 | PEx1-4 | ESI+: 387.1 |
| PEx1-5 | PEx1-5 | ESI+: 519.2 |
| PEx1-6 | PEx1-6 | ESI+: 570.3 |
| Ex1 | Ex1 | ESI+: 470.5<br>$^1$HNMR(400 MHz, DMSO-d$_6$)δppm7.22(d, J = 2.88 Hz, 1H), 6.99(s, 1H), 6.77(d, J = 7.76 Hz, 1H), 6.38(d, J = 7.76 Hz,1H), 5.96(d, J = 2.88 Hz, 1H), 5.57(t, J = 5.20 Hz, 1H), 5.37(s, 2H), 5.30(s, 2H), 4.42-4.76(m, 2H), 3.88(brd, J = 14.00 Hz, 1H), 3.85(s, 3H), 3.22-3.31(m, 4H), 2.83(brd, J = 9.12 Hz, 1H), 2.51-2.70(m, 5H), 2.01-2.10(m, 1H), 1.30-1.40(m, 2H), 1.13-1.25(m, 2H), 0.99-1.11(m, 2H), 0.80(t, J = 7.24 Hz, 3H)<br>[σ]$_o^{20}$ − 17.8(c 0.1, CHCl$_3$) |
| PEx2-1 | PEx2-1 | ESI+: 395.6 |
| PEx2-2 | PEx2-2 | ESI+: 295.3 |
| PEx2-3 | PEx2-3 | ESI+: 445.2 |
| PEx2-4 | PEx2-4 | ESI+: 620.3 |
| Ex2 | Ex2 | ESI+: 470.4<br>$^1$HNMR(400 MHz, DMSO-d$_6$)δppm12.6(s, 1H), 9.20(brs, 1H), 7.50(s, 2H), 7.41(d, J = 2.8 Hz, 1H), 7.40(t, J = 5.2 Hz, 1H), 7.06(s, 1H), 6.86(d, J = 7.6 Hz, 1H), 6.56(d, J = 7.6 Hz, 1H), 6.20(d, J = 2.8 Hz, 1H), 5.54(s, 2H), 4.75-4.65(m, 1H), 4.60-4.55(m, 1H), 3.84(s, 3H), 3.70(s, 2H), 3.70-3.60(m, 1H), 3.50-3.45(m, 2H), 3.42-3.32(m, 1H), 3.20-3.10(m, 1H), 3.10-2.90(m, 1H), 2.50-2.40(m, 2H), 1.50-1.42(m, 2H), 1.25-1.18(m, 2H), 1.15-1.05(m, 2H), 0.81(t, J = 7.2 Hz, 3H) |
| PEx3-1 | PEx3-1 | ESI+: 370.3 |
| PEx3-2 | PEx3-2 | ESI+: 368.2 |
| Ex3 | Ex3 | ESI+: 409.3 |
| PEx4-1 | PEx4-1 | ESI+: 387.2 |
| Ex4 | Ex4 | ESI+: 455.3 |
| PEx5-1 | PEx5-1 | ESI+: 402.2 |
| Ex5 | Ex5 | ESI+: 470.3 |
| PEx6-1 | PEx6-1 | ESI+: 422.2 |

TABLE 6-2

| NUM | REF | DAT |
|---|---|---|
| Ex6 | Ex6 | ESI+: 487.4<br>$^1$HNMR(500 MHz, DMSO-d$_6$)δppm7.36(s, 1H), 6.99(d, J = 1.07 Hz, 1H), 6.79(dd, J = 1.03, 7.73, 1H), 6.47(d, J = 7.65 Hz, 1H), 5.75(t, J = 5.51 Hz, 1H), 5.56(s, 2H), 5.35(s, 2H), 4.36(t, J = 5.43, 1H), 3.99(d, J = 13.46 Hz, 1H), 3.84(s, 3H), 3.39-3.45(m, 1H), 3.24-3.30(m, 4H), 2.73-2.78(m, 1H), 2.52-2.56(m, 1H), 2.07-2.15(m, 1H), 1.77-1.86(m, 1H), 1.50-1.61(m, 3H), 1.37(quintet, J = 7.31 Hz, 2H), 1.15-1.26(m, 2H), 1.04-1.11(m, 2H), 0.81(t, J = 7.34 Hz, 3H) |
| PEx7-1 | PEx7-1 | ESI+: 425.1, 427.1 |
| PEx7-2 | PEx7-2 | ESI+: 450.5 |
| PEx7-3 | PEx7-3 | ESI+: 466.4, 468.4 |
| Ex7 | Ex7 | ESI+: 533.5 |
| PEx8-1 | PEx8-1 | ESI+: 337.3 |
| PEx8-2 | PEx8-2 | ESI+: 241.0 |
| PEx8-3 | PEx8-3 | ESI+: 559.3 |
| PEx8-4 | PEx8-4 | ESI+: 501.3 |
| Ex8 | Ex8 | ESI+: 452.3 |
| PEx9-1 | PEx9-1 | ESI+: 537.5 |
| Ex9 | Ex9 | ESI+: 437.4 |
| PEx10-1 | PEx1-1 | ESI+: 397.2 |
| PEx10-2 | PEx1-3 | ESI+: 369.2 |
| PEx10-3 | PEx1-4 | ESI+: 387.2 |
| PEx10-4 | PEx1-5 | ESI+: 519.2 |
| PEx10-5 | PEx1-6 | ESI+: 570.3 |
| Ex10 | Ex10 | ESI+: 470.5<br>$^1$HNMR(400 MHz, DMSO-d$_6$): δppm7.25(d, J = 3.00 Hz, 1H), 7.00(s, 1H), 6.78(d, J = 7.76 Hz, 1H), 6.41(d, J = 7.64 Hz, 1H), 6.00(d, J = 3.00 Hz, 1H), 5.85(brt, J = 5.20 Hz, 1H), 5.62(brs, 2H), 5.39(s, 2H), 4.49-4.73(m, 2H), 3.90(brd, J = 13.88 Hz, 1H), |

TABLE 6-2-continued

| NUM | REF | DAT |
|---|---|---|
| | | 3.84(s, 3H), 3.26-3.36(m, 3H), 2.86-2.96(m, 1H), 2.51-2.77(m, 6H), 2.06-2.18(m, 1H), 1.30-1.45(m, 2H), 1.15-1.25(m, 2H), 1.02-1.11(m, 2H), 0.80(t, J = 7.24 Hz, 3H) [$\sigma$]$_o^{20}$ + 26.85(c 0.1, CHCl$_3$) |
| Ex11 | PEx4-1, Ex2 | ESI+: 512.3 |
| Ex12 | PEx2-3 | ESI+: 437.4 |
| Ex13 | Ex4 | ESI+: 456.3 |
| Ex14 | Ex4 | ESI+: 470.3 |
| Ex15 | Ex4, Ex1 | ESI+: 469.4 |

TABLE 6-3

| NUM | REF | DAT |
|---|---|---|
| Ex17 | PEx1-1 | ESI+: 473.4 |
| Ex18 | PEx1-1 | ESI+: 515.4 |
| ExL1 | ExL1 | ESI+: 621.6<br>$^1$HNMR(400 MHz, DMSO-d$_6$)δppm12.29(brs, 1H), 7.38-7.48 (m, 3H), 7.35(brs, 1H), 7.11(brs, 1H), 7.03(d, J = 3.12 Hz, 2H), 6.89(brd J = 7.00 Hz, 1H), 6.54(brd, J = 7.76 Hz, 1H), 6.22(d, J = 2.88 Hz, 1H), 5.55(s, 2H), 4.58-4.90(m, 2H), 3.85(s, 3H), 3.49-3.64(m, 8H), 3.39-3.49(m, 2H), 3.25-3.35(m, 2H , 2.70-2.85(m, 1H),2.56-2.64(m, 2H), 1.40-1.50(m, 2H), 1.17-1.26 (m, 2H), 1.04-1.13(m, 2H), 0.81(t, J = 7.24 Hz, 3H) [$\sigma$]$_o^{20}$ − 13.0(c 0.065, MeCN) |
| ExL3 | ExL3 | ESI+: 1044.6 |
| ExL4 | ExL4 | ESI+: 578.3 |
| PExL5-1 | PExL5-1 | ESI+: 422.4 |
| PExL5-2 | PExL5-2 | ESI+: 288.2 |
| PExL5-3 | PExL5-3 | ESI+: 673.5 |
| ExL5 | ExL5 | ESI+: 653.5 |
| PExL6-1 | PExL6-1 | ESI+: 246.2 |
| PExL6-2 | PExL6-2 | ESI+: 397.3[M + Na]$^+$ |
| PExL6-3 | PExL6-3 | ESI+: 275.2 |
| PExL6-4 | PExL6-4 | ESI+: 530.4 |
| ExL6 | ExL6 | ESI+: 610.5 |
| ExL7 | ExL1 | ESI+: 560.3 |
| ExL8 | ExL1 | ESI+: 606.3 |
| ExL9 | ExL1 | ESI+: 621.5<br>$^1$HNMR(400 MHz, DMSO-d$_6$)δppm12.21(brs, 1H), 7.32-7.44 (m, 4H), 7.09(s, 1H), 7.02(d, J = 3.20 Hz, 2H), 6.88(brd, J = 7.20 Hz, 1H), 6.54(d, J = 7.20 Hz, 1H), 6.22(d, J = 3.20 Hz, 1H), 5.54(s, 2H), 4.80-4.95(m, 2H), 3.95-4.40(m, 1H), 3.84(s, 3H), 3.55-3.65 (m, 2H), 3.33-3.56(m, 7H), 2.85-2.95(m, 1H), 2.70-2.80(m, 1H), 2.55-2.62(m, 1H), 2.52-2.53(m, 2H), 1.40-1.50(m, 2H), 1.15-1.25(m, 2H), 1.05-1.15(m, 2H), 0.81(t, J = 7.24 Hz, 3H) [$\sigma$]$_o^{20}$ + 11.1(c 0.065, MeCN) |
| ExL10 | ExL3 | ESI+: 868.6 |
| ExL1A1 | ExL1A1 | DAR: n = 3.44, SEC analysis: 100% monomer |
| ExL1A2 | ExL1A2 | DAR: n = 4.02, SEC analysis: 99.5% monomer |
| ExL5A1 | ExL5A1 | DAR: n = 2.95, SEC analysis: 99.1% monomer |
| ExL7A1 | ExL7A1 | DAR: n = 3.28, SEC analysis: 100% monomer |
| ExL9A1 | ExL5A1 | DAR: n = 3.58, SEC analysis: 99.4% monomer |

INDUSTRIAL APPLICABILITY

An antibody-drug conjugate of formula (I) or a salt thereof has excellent TLR7/8 dual agonistic action, effects on production of TNF-α and INF-γ and an in-vivo antitumor effect. Because of this, it is expected that the antibody-drug conjugate or a salt thereof is useful for prevention and/or treatment for various cancers such as ovarian cancer, testicular cancer, cervical cancer, and lung cancer. The anti-CLDN6 antibody found in the present invention has a binding activity to human CLDN6. Because of this, it is expected that the anti-CLDN6 antibody is used in an antibody-drug conjugate or a salt thereof for use in preparing a prophylactic and/or therapeutic agent for cancer.

SEQUENCE LISTING FREE TEXT

SEQ ID NO: 2 represents the amino acid sequence of a heavy chain of humanized anti-CLDN6 antibody Ab1 and the nucleotide sequence represented by SEQ ID NO: 1 encodes the amino acid sequence represented by SEQ ID NO: 2. SEQ ID NO: 4 represents the amino acid sequence of a light chain of humanized anti-CLDN6 antibody Ab1 and the nucleotide sequence represented by SEQ ID NO: 3 encodes the amino acid sequence represented by SEQ ID NO: 4. SEQ ID NO: 6 represents the amino acid sequence of a heavy chain of humanized anti-CLDN6 antibody Ab2 and the nucleotide sequence represented by SEQ ID NO: 5 encodes the amino acid sequence represented by SEQ ID NO: 6. SEQ ID NO: 8 represents the amino acid sequence of a light chain of humanized anti-CLDN6 antibody Ab2 and the nucleotide sequence represented by SEQ ID NO: 7 encodes the amino acid sequence represented by SEQ ID NO: 8

Sequence Listing

The invention claimed is:

1. An antibody-drug conjugate of formula (I) or salt thereof:

$(D_L\text{-})_n\text{-Ab}$ (I), wherein $D_L$ is a drug-linker of the antibody-drug conjugate, Ab is an anti-CLDN6 antibody or an antigen-binding fragment thereof, and n is in a range of from 1 to 16, and wherein the antibody-drug conjugate of formula (I) is selected from the group consisting of an antibody-drug conjugate consisting of Ab bound to 1-{3-[(3S)-4-[(4-{[2-amino-4-(pentylamino)-5H-pyrrolo[3,2-d]pyrimidin-5-yl]methyl}-3-methoxyphenyl)methyl]-3-(fluoromethyl)piperazin-1-yl]-3-oxopropyl}-1H-pyrrole-2,5-dione, an antibody-drug conjugate consisting of Ab bound to {(2S)-1-[(4-{[2-amino-7-chloro-4-(pentylamino)-5H-pyrrolo[3,2-d]pyrimidin-5-yl]methyl}-3-methoxyphenyl)methyl]pyrrolidin-2-yl}methyl[2-(2,5-dioxo-2,5-dihydro-1H-pyrrol-1-yl)ethyl]carbamate, an antibody-drug conjugate consisting of Ab bound to N-[(4-{[2-amino-4-(pentylamino)-5H-pyrrolo[3,2-d]pyrimidin-5-yl]methyl}-3-methoxyphenyl)methyl]-N-cyclopropyl-3-(2,5-dioxo-2,5-dihydro-1H-pyrrol-1-yl)propenamide, and an antibody-drug conjugate consisting of Ab bound to 1-{3-[(3R)-4-[(4-{[2-amino-4-(pentylamino)-5H-pyrrolo[3,2-d]pyrimidin-5-yl]methyl}-3-methoxyphenyl)methyl]-3-(fluoromethyl)piperazin-1-yl]-3-oxopropyl}-1H-pyrrole-2,5-dione.

2. The antibody-drug conjugate or salt of claim 1, wherein Ab is an anti-CLDN6 antibody or an antigen-binding fragment thereof selected from the group consisting of Ab-A and Ab-B, wherein Ab-A is an anti-CLDN6 antibody or an antigen-binding fragment thereof comprising a heavy chain variable region comprising CDR1 consisting of amino acid sequence of amino acid Nos. 31 to 35 of SEQ ID NO: 2, CDR2 consisting of the amino acid sequence of amino acid Nos. 50 to 65 of SEQ ID NO: 2, and CDR3 consisting of the amino acid sequence of amino acid Nos. 95 to 102 of SEQ ID NO: 2; and a light chain variable region comprising CDR1 consisting of the amino acid sequence of amino acid Nos. 24 to 34 of SEQ ID NO: 4, CDR2 consisting of the amino acid sequence of amino acid Nos. 50 to 56 of SEQ ID NO: 4, and CDR3 consisting of the amino acid sequence of amino acid Nos. 89 to 97 of SEQ ID NO: 4, and wherein Ab-B is an anti-CLDN6 antibody or an antigen-binding fragment thereof comprising a heavy chain variable region comprising CDR1 consisting of the amino acid sequence of amino acid Nos. 31 to 35 of SEQ ID NO: 6, CDR2 consisting of the amino acid sequence of amino acid Nos. 50 to 65 of SEQ ID NO: 6, and CDR3 consisting of the amino acid sequence of amino acid Nos. 95 to 102 of SEQ ID NO: 6; and a light chain variable region comprising CDR1 consisting of the amino acid sequence of amino acid Nos. 24 to 34 of SEQ ID NO: 8, CDR2 consisting of the amino acid sequence of amino acid Nos. 50 to 56 of SEQ ID NO: 8, and CDR3 consisting of the amino acid sequence of amino acid Nos. 89 to 97 of SEQ ID NO: 8.

3. The antibody-drug conjugate or salt of claim 1, wherein Ab is an anti-CLDN6 antibody or an antigen-binding fragment thereof selected from the group consisting of Ab-C and Ab-D, wherein Ab-C is an anti-CLDN6 antibody or an antigen-binding fragment thereof comprising a heavy chain variable region consisting of the amino acid sequence of amino acid Nos. 1 to 117 of SEQ ID NO: 2 and a light chain variable region consisting of the amino acid sequence of the amino acid Nos. 1 to 108 of SEQ ID NO: 4, and wherein Ab-D is an anti-CLDN6 antibody or an antigen-binding fragment thereof comprising a heavy chain variable region consisting of the amino acid sequence of amino acid Nos. 1 to 117 of SEQ ID NO: 6 and a light chain variable region consisting of the amino acid sequence of amino acid Nos. 1 to 108 of SEQ ID NO: 8.

4. The antibody-drug conjugate or salt of claim 2, wherein Ab is Ab1 or Ab2, and wherein Ab1 is an anti-CLDN6 antibody comprising a heavy chain consisting of the amino acid sequence of SEQ ID NO: 2 and a light chain consisting of the amino acid sequence of SEQ ID NO: 4, and wherein Ab2 is an anti-CLDN6 antibody comprising a heavy chain consisting of the amino acid sequence of SEQ ID NO: 6 and a light chain consisting of the amino acid sequence of SEQ ID NO: 8.

5. The antibody-drug conjugate or salt of claim 1, wherein Ab is Ab1 or Ab2, wherein the antibody-drug conjugate is selected from the group consisting of an antibody-drug conjugate consisting of Ab1 bound to 1-{3-[(3S)-4-[(4-{[2-amino-4-(pentylamino)-5H-pyrrolo[3,2-d]pyrimidin-5-yl]methyl}-3-methoxyphenyl)methyl]-3-(fluoromethyl)piperazin-1-yl]-3-oxopropyl}-1H-pyrrole-2,5-dione, an antibody-drug conjugate consisting of Ab2 bound to 1-{3-[(3S)-4-[(4-{([2-amino-4-(pentylamino)-5H-pyrrolo[3,2-d]pyrimidin-5-yl]methyl}-3-methoxyphenyl)methyl]-3-(fluoromethyl)piperazin-1-yl]-3-oxopropyl}-1H-pyrrole-2,5-dione, an antibody-drug conjugate consisting of Ab1 bound to {(2S)-1-[(4-{[2-amino-7-chloro-4-(pentylamino)-5H-pyrrolo[3,2-d]pyrimidin-5-yl]methyl}-3-methoxyphenyl)methyl]pyrrolidin-2-yl}methyl[2-(2,5-dioxo-2,5-dihydro-1H-pyrrol-1-yl)ethyl]carbamate, an antibody-drug conjugate consisting of Ab1 bound to N-[(4-{[2-amino-4-(pentylamino)-5H-pyrrolo[3,2-d]pyrimidin-5-yl]methyl}-3-methoxyphenyl)methyl]-N-cyclopropyl-3-(2,5-dioxo-2,5-dihydro-1H-pyrrol-1-yl)propenamide, and an antibody-drug conjugate consisting of Ab1 bound to 1-{3-[(3R)-4-[(4-{[2-amino-4-(pentylamino)-5H-pyrrolo[3,2-d]pyrimidin-5-yl]methyl}-3-methoxyphenyl)methyl]-3-(fluoromethyl)piperazin-1-yl]-3-oxopropyl}-1H-pyrrole-2,5-dione, and wherein Ab1 is an antibody comprising a heavy chain consisting of the amino acid sequence of SEQ ID NO: 2 and a light chain consisting of the amino acid sequence of SEQ ID NO: 4, Ab2 is an antibody comprising a heavy chain consisting of the amino acid sequence of SEQ ID NO: 6 and a light chain consisting of the amino acid sequence of SEQ ID NO: 8.

6. The antibody-drug conjugate or salt of claim 1, wherein the antibody-drug conjugate is

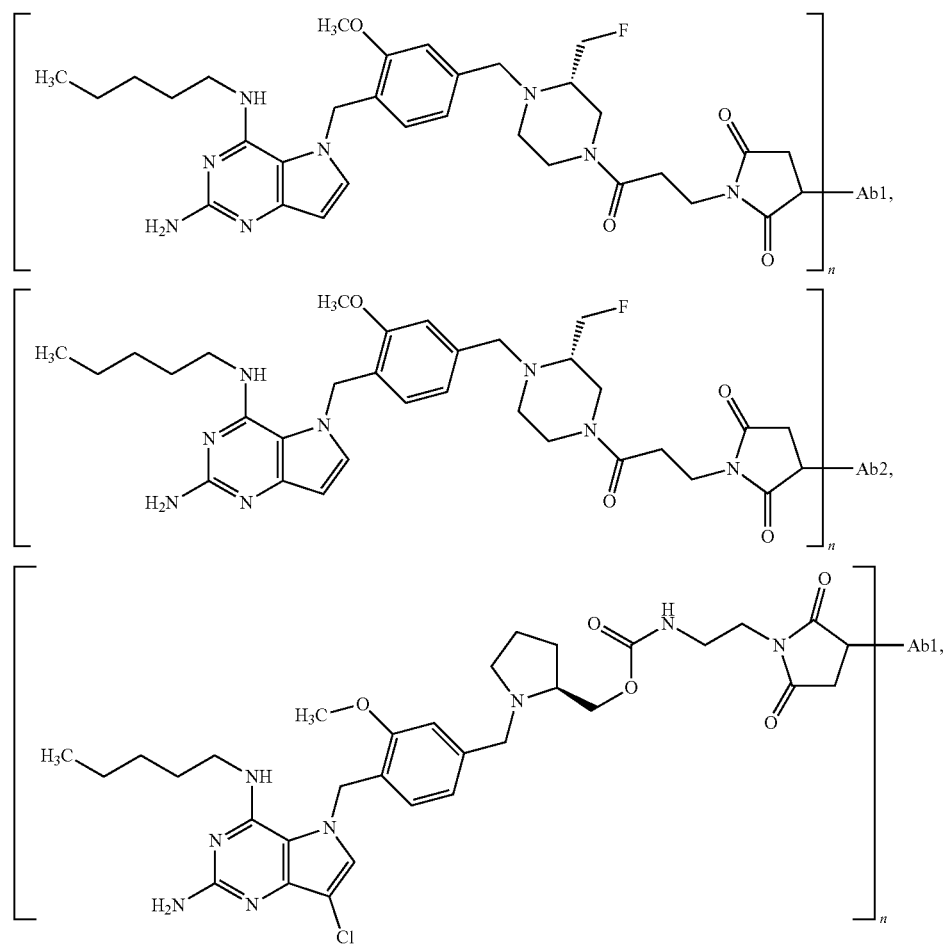

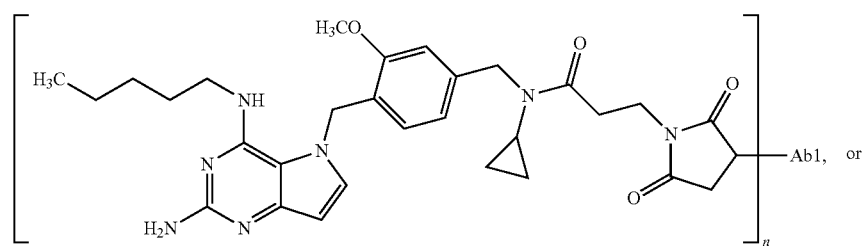

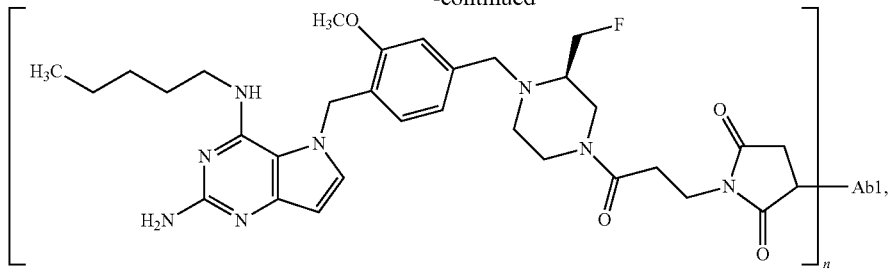

and

Ab1 is an antibody comprising a heavy chain consisting of the amino acid sequence of SEQ ID NO: 2 and a light chain consisting of the amino acid sequence of SEQ ID NO: 4, Ab2 is an antibody comprising a heavy chain consisting of the amino acid sequence of SEQ ID NO: 6 and a light chain consisting of the amino acid sequence of SEQ ID NO: 8, and n is 1 to 16.

7. The antibody-drug conjugate or salt of claim 6, wherein the antibody-drug conjugate is

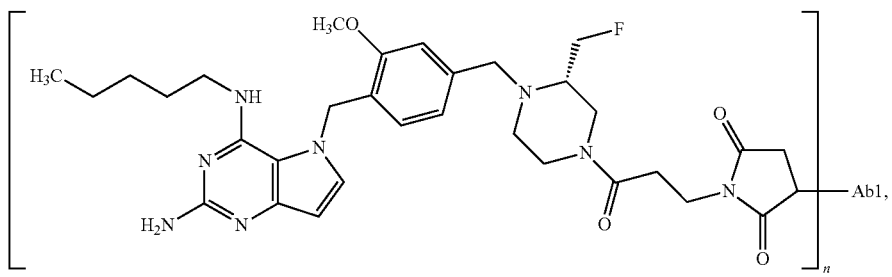

8. The antibody-drug conjugate or salt of claim 6, wherein the antibody-drug conjugate is

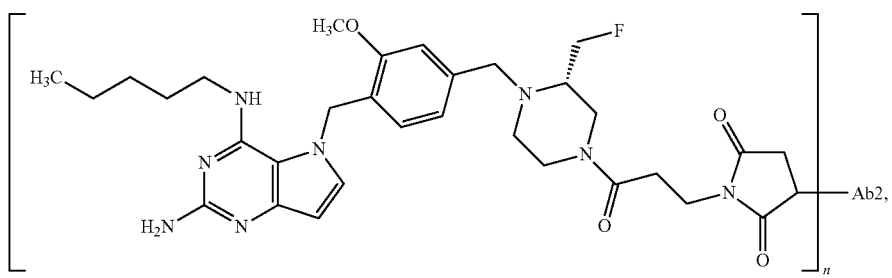

9. The antibody-drug conjugate or salt of claim 6, wherein the antibody-drug conjugate is
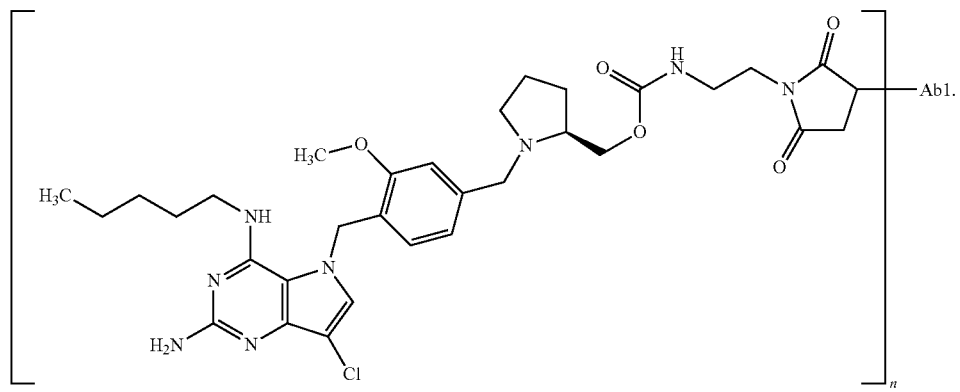
10. The antibody-drug conjugate or salt of claim 6, wherein the antibody-drug conjugate is
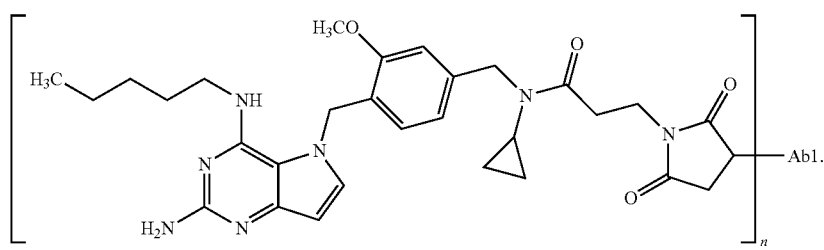
11. The antibody-drug conjugate or salt of claim 6, wherein the antibody-drug conjugate is
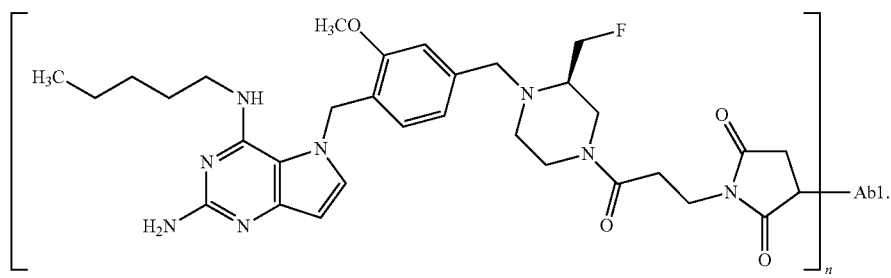
12. The antibody-drug conjugate or salt of claim 6, wherein the antibody-drug conjugate is
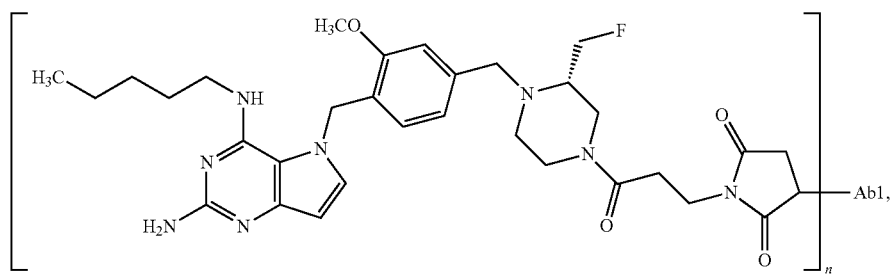

and
wherein n is in a range of from 1 to 8.

13. A pharmaceutical composition, comprising:
the antibody-drug conjugate or salt of claim 1; and
a pharmaceutically acceptable excipient.

14. The composition of claim 13, which is a cancer-treating formulation,
wherein a cancer treated by the cancer-treating formulation comprises ovarian cancer, non-small-cell lung cancer, or uterine cancer.

15. A method for treating cancer, comprising:
administering to a subject in need thereof an effective amount of the antibody-drug conjugate or salt of claim 1 to the subject,
wherein the cancer comprises ovarian cancer, non-small-cell lung cancer, or uterine cancer.

16. A method for treating cancer, comprising:
administering to a subject in need thereof an effective amount of the antibody-drug conjugate or salt of claim 1 to the subject.

17. A pharmaceutical composition, comprising:
the antibody-drug conjugate or salt of claim 7; and
a pharmaceutically acceptable excipient.

18. A pharmaceutical composition, comprising:
the antibody-drug conjugate or salt of claim 8; and
a pharmaceutically acceptable excipient.

19. A pharmaceutical composition, comprising:
the antibody-drug conjugate or salt of claim 9; and
a pharmaceutically acceptable excipient.

20. A pharmaceutical composition, comprising:
the antibody-drug conjugate or salt of claim 10; and
a pharmaceutically acceptable excipient.

21. A pharmaceutical composition, comprising:
the antibody-drug conjugate or salt of claim 11; and
a pharmaceutically acceptable excipient.

22. A pharmaceutical composition, comprising:
the antibody-drug conjugate or salt of claim 12; and
a pharmaceutically acceptable excipient.

* * * * *

```
                           SEQUENCE LISTING

Sequence total quantity: 8
SEQ ID NO: 1            moltype = DNA   length = 1341
FEATURE                 Location/Qualifiers
source                  1..1341
                        mol_type = other DNA
                        organism = synthetic construct
SEQUENCE: 1
caggtgcagc tggtggaatc tggtggcgga gttgttcagc ctggcggctc tctgagactg   60
tcctgcaagg cttccggcta ctccttcacc ggctacacca tgaactgggt ccgacaggct  120
cctggcaaag gcctggaatg ggtcggactg atcaaccct ataacggcgg caccatctac   180
aaccagaagt tcaagggcag attcaccctg tccgtggaca agtccaagtc caccgcctac  240
ctgcagatga actccctgag agccgaggac accgccgtgt actactgcgc tagagactac  300
ggcttcgtgc tggactattg gggcagaggc acactggtca ccgtgtcctc tgctagcaca  360
aagggaccta gcgtatttcc attggctcct agcagcaaat ccacaagtgg tggaactgct  420
gcactgggtt gtctggttaa ggattatttc ccagagccag tcacagtttc ctggaactct  480
ggggcactga cctccggagt gcacacattc ccagccgtac ttcaatccag tggtctctac  540
agcctttctt cagtagtaac cgttccatct tctagcctcg gaacccaaac ttatatttgc  600
aatgtgaatc acaagccttc taacactaag gttgataaac gagtcgaacc aaaatcctgc  660
gataagaccc acacttgccc accttgcccc gcaccagaat tgttgggtgg accctctgtg  720
ttcctctttc cacctaaacc taaggacact cttatgatct cacgcactcc tgaagtaacc  780
tgtgtagtag tagacgtaag ccatgaagac cccgaagtga agttcaactg gtatgttgat  840
ggtgtcgaag tgcataatgc caagactaaa ccccgagaag aacagtataa ttctacttat  900
agagtggtgt cagtgttgac agttctgcac caagattggc tcaatggtaa ggagtacaaa  960
tgcaaggtgt caaacaaggc actgccagcc cctattgaaa agaccatcag caaggccaag 1020
ggccaacctc gagagccaca agtctacact ctccctcctt cacgtgagga tgactaag   1080
aatcaggttt ctctgacatg tttggtaaag ggtttctacc caagcgacat agctgtggag 1140
tgggaatcta atggtcaacc agagaacaat tacaaaacca ccccaccgt tctcgactct  1200
gacggcagtt tcttcctgta tagcaaactt actgtggata aatcccgatg gcaacaaggc 1260
aacgtctttt cttgttccgt gatgcatgag gcacttcata accactatac acaaaagagt 1320
ttgtctttgt ctccaggaaa a                                          1341

SEQ ID NO: 2            moltype = AA   length = 447
FEATURE                 Location/Qualifiers
source                  1..447
                        mol_type = protein
                        organism = synthetic construct
SEQUENCE: 2
QVQLVESGGG VVQPGGSLRL SCKASGYSFT GYTMNWVRQA PGKGLEWVGL INPYNGGTIY   60
NQKFKGRFTL SVDKSKSTAY LQMNSLRAED TAVYYCARDY GFVLDYWGRG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKRVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSREEMTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                     447

SEQ ID NO: 3            moltype = DNA   length = 642
FEATURE                 Location/Qualifiers
source                  1..642
                        mol_type = other DNA
                        organism = synthetic construct
SEQUENCE: 3
gacatccagc tgacccagtc tccatcctct ctgtctgcct ctgtgggcga cagagtgaca   60
attacctgct ccgcctcctc ctccgtgtcc tacctgcatt ggttccagca gaagcctggc  120
aaggccccta agctgctggt gtactccacc tccaatctgc cttccggcgt gccctctaga  180
ttctccggat ctggctctgg caccgactat accctgacaa tctccagcct gcagcctgag  240
gacttcgcca cctactactg ccagcagcgg tctatctacc ctccttggac ctttggccag  300
ggcaccaagc tggaaatcaa gcgtacggtg gccgctcctc ccgtgttcat cttcccacct  360
tccgacgagc agctgaagtc cggcacagct tctgtcgtgt gcctgctgaa caacttctac  420
cctcgggaag ccaaggtgca gtggaaggtg gacaatgccc tgcagtccgg caactccaa  480
gagtctgtga ccgagcagga ctccaaggac agcacctaca gcctgtcctc cacactgacc  540
ctgtccaagg ccgactacga aagcacaag gtgtacgcct gcgaagtgac ccatcagggc  600
ctgtctagcc ctgtgaccaa gtctttcaac cggggcgagt gc                    642

SEQ ID NO: 4            moltype = AA   length = 214
FEATURE                 Location/Qualifiers
source                  1..214
                        mol_type = protein
                        organism = synthetic construct
```

```
SEQUENCE: 4
DIQLTQSPSS LSASVGDRVT ITCSASSSVS YLHWFQQKPG KAPKLLVYST SNLPSGVPSR    60
FSGSGSGTDY TLTISSLQPE DFATYYCQQR SIYPPWTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 5            moltype = DNA   length = 1341
FEATURE                 Location/Qualifiers
source                  1..1341
                        mol_type = other DNA
                        organism = synthetic construct
SEQUENCE: 5
caggtgcagc tggtggaatc tggtggcgga gttgttcagc ctggcggctc tctgagactg     60
tcctgcaagg cttccggcta ctccttcacc ggctacacca tgaactgggt ccgacaggct   120
cctggcaaag gcctggaatg ggtcggactg atcaacccct ataacggcgg caccatctac   180
aaccagaagt tcaagggcag attcaccctg tccgtggaca gtccaagtc caccgccctc   240
ctgcagatga actccctgag agccgaggac accgccgtgt actactgcgc tagagactac   300
ggctacgtgc tggactattg gggcagaggc acactggtca ccgtgtcctc tgctagcaca   360
aagggaccta gcgtatttcc attggctcct agcagcaaat ccacaagtgg tggaactgct   420
gcactgggtt gtctggttaa ggattatttc ccagagccag tcacagtttc tggaactct   480
ggggcactga cctccggagt gcacacattc ccagccgtac ttcaatccag tggtctctac   540
agcctttctt cagtagtaac cgttccatct tctagcctcg gaacccaaac ttatatttgc   600
aatgtgaatc acaagccttc taacactaag gttgataaac gagtcgaacc aaaatcctgc   660
gataagaccc acacttgccc accttgcccc gcaccagaat tgttgggtgg accctctgtg   720
ttcctctttc cacctaaacc taaggacact cttatgatct cacgcactcc tgaagtaacc   780
tgtgtagtag tagacgtaag ccatgaagac cccgaagtga agttcaactg gtatgttgat   840
ggtgtcgaag tgcataatgc caagactaaa ccccgagaag aacagtataa ttctacttat   900
agagtggtgt cagtgttgac agttctgcac caagattggc tcaatggtaa ggagtacaaa   960
tgcaaggtgt caaacaaggc actgccagcc cctattgaaa agaccatcag caaggccaag  1020
ggccaacctc gagagccaca agtctacact ctccctcctt cacgtgagga tgactaag   1080
aatcaggttt ctctgacatg tttggtaaag ggtttctacc caagcgacat agctgtggag  1140
tgggaatcta atggtcaacc agagaacaat tacaaaacca ccccaccgt tctcgactct  1200
gacggcagtt tcttcctgta tagcaaactt actgtggata atcccgatg caacaaggc   1260
aacgtctttt cttgttccgt gatgcatgag gcacttcata accactatac acaaaagagt  1320
ttgtctttgt ctccaggaaa a                                             1341

SEQ ID NO: 6            moltype = AA    length = 447
FEATURE                 Location/Qualifiers
source                  1..447
                        mol_type = protein
                        organism = synthetic construct
SEQUENCE: 6
QVQLVESGGG VVQPGGSLRL SCKASGYSFT GYTMNWVRQA PGKGLEWVGL INPYNGGTIY    60
NQKFKGRFTL SVDKSKSTAY LQMNSLRAED TAVYYCARDY GYVLDYWGRG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKRVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                       447

SEQ ID NO: 7            moltype = DNA   length = 642
FEATURE                 Location/Qualifiers
source                  1..642
                        mol_type = other DNA
                        organism = synthetic construct
SEQUENCE: 7
gacatccagc tgacccagtc tccatcctct ctgtctgcct ctgtgggcga cagagtgaca    60
attacctgct ccgcctcctc ctccgtgtcc tacctgcatt ggttccagca gaagcctggc   120
aaggccccta gctgctggt gtactccacc tccaatctgc cttccggcgt gccctctaga   180
ttctccggat ctggctctgg caccgactat accctgacaa tctccagcct gcagcctgag   240
gacttcgcca cctactactg ccagcagcgg tctatctacc ctccttggac ctttggccag   300
ggcaccaagc tggaaatcaa gcgtacggtg gccgctcctt ccgtgttcat cttcccacct   360
tccgacgagc agctgaagtc cggacagct tctgtcgtgt gcctgctgaa caacttctac   420
cctcgggaag ccaaggtgca gtggaaggtg gacaatgccc tgcagtccgg caactcccaa   480
gagtctgtga ccgagcagga ctccaaggac agcacctaca gcctgtcctc cacactgacc   540
ctgtccaagg ccgactacga aaagcacaag gtgtacgcct gcgaagtgac ccatcaggc   600
ctgtctagcc ctgtgaccaa gtcttcaac cggggcgagt gc                       642
```

```
SEQ ID NO: 8          moltype = AA  length = 214
FEATURE               Location/Qualifiers
source                1..214
                      mol_type = protein
                      organism = synthetic construct
SEQUENCE: 8
DIQLTQSPSS LSASVGDRVT ITCSASSSVS YLHWFQQKPG KAPKLLVYST SNLPSGVPSR  60
FSGSGSGTDY TLTISSLQPE DFATYYCQQR SIYPPWTFGQ GTKLEIKRTV AAPSVFIFPP 120
SDEQLKSGTA SVVCLLNNFY PREAKVQWKV DNALQSGNSQ ESVTEQDSKD STYSLSSTLT 180
LSKADYEKHK VYACEVTHQG LSSPVTKSFN RGEC                            214
```